(12) United States Patent
Foong

(10) Patent No.: US 12,263,305 B2
(45) Date of Patent: Apr. 1, 2025

(54) CONDUIT WITH MAGNETIC CONNECTOR

(71) Applicant: ResMed Pty Ltd, Bella Vista (AU)

(72) Inventor: Yi Mei Foong, Singapore (SG)

(73) Assignee: ResMed Pty Ltd, Bella Vista (AU)

( * ) Notice: Subject to any disclaimer, the term of this patent is extended or adjusted under 35 U.S.C. 154(b) by 1081 days.

(21) Appl. No.: 17/177,611

(22) Filed: Feb. 17, 2021

(65) Prior Publication Data

US 2021/0170129 A1 Jun. 10, 2021

Related U.S. Application Data

(63) Continuation of application No. 16/635,267, filed as application No. PCT/IB2019/052395 on Mar. 25, 2019, now Pat. No. 10,953,180.

(60) Provisional application No. 62/649,941, filed on Mar. 29, 2018.

(51) Int. Cl.
*A61M 16/06* (2006.01)
*A61M 16/08* (2006.01)

(52) U.S. Cl.
CPC .... *A61M 16/0622* (2014.02); *A61M 16/0666* (2013.01); *A61M 16/0683* (2013.01); *A61M 16/0816* (2013.01); *A61M 16/0875* (2013.01); *A61M 2205/0272* (2013.01)

(58) Field of Classification Search
CPC .......... A61M 16/0051; A61M 16/0057; A61M 16/0066; A61M 16/021; A61M 16/06; A61M 16/0605; A61M 16/0666; A61M 16/0683; A61M 16/0816; A61M 16/0825; A61M 16/0875; A61M 2039/1027; A61M 2039/1038; A61M 2039/1044; A61M 2205/0222; A61M 2205/0238; A61M 2205/14; A61M 2205/583; A61M 2209/08; A61M 39/1011; A62B 9/04

See application file for complete search history.

(56) References Cited

U.S. PATENT DOCUMENTS

| | | |
|---|---|---|
| 4,782,832 A | 11/1988 | Trimble et al. |
| 4,944,310 A | 7/1990 | Sullivan |
| 6,532,959 B1 | 3/2003 | Berthon-Jones |
| 6,581,594 B1 | 6/2003 | Drew et al. |
| 6,907,882 B2 | 6/2005 | Ging et al. |

(Continued)

FOREIGN PATENT DOCUMENTS

| | | |
|---|---|---|
| WO | WO 98/004310 A1 | 2/1998 |
| WO | WO 98/034665 A1 | 8/1998 |

(Continued)

OTHER PUBLICATIONS

"Respiratory Physiology", by John B. West, Lippincott Williams & Wilkins, 9th edition published 2012 (8 pages).

(Continued)

*Primary Examiner* — Annette Dixon
(74) *Attorney, Agent, or Firm* — Nixon & Vanderhye P.C.

(57) ABSTRACT

A therapy device that includes an air conduit that is configured both to secure the patient interface to the patient as well as provide pressurised air to the patient. The positioning and stabilising structure of the patient interface may include magnets that assist in positioning the positioning and stabilising structure and also assist in positioning the air conduit of the positioning and stabilising structure to interact with the mask assembly.

20 Claims, 34 Drawing Sheets

(56) References Cited

U.S. PATENT DOCUMENTS

| | | |
|---|---|---|
| 7,318,437 B2 | 1/2008 | Gunaratnam et al. |
| 7,793,987 B1 | 9/2010 | Busch et al. |
| 7,866,944 B2 | 1/2011 | Kenyon et al. |
| 7,942,148 B2 | 5/2011 | Davidson et al. |
| 8,042,542 B2 | 10/2011 | Ging et al. |
| 8,387,616 B2 | 3/2013 | Ging |
| 8,573,200 B2 | 11/2013 | Busch et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 8,746,249 B2 | 6/2014 | Matula, Jr. et al. |
| 8,770,190 B2 | 7/2014 | Doherty et al. |
| 8,863,745 B2 | 10/2014 | Ging |
| 9,669,180 B2 | 6/2017 | Ging |
| 10,016,569 B2 | 7/2018 | Flower |
| 10,166,357 B2 | 1/2019 | Veliss et al. |
| 10,206,571 B2 | 2/2019 | Ewers et al. |
| 10,232,137 B2 | 3/2019 | Romagnoli et al. |
| 10,449,317 B2 | 10/2019 | Barlow |
| 10,744,293 B2 | 8/2020 | Romagnoli |
| 10,814,087 B2 | 10/2020 | Ging |
| 10,953,180 B2 * | 3/2021 | Foong ............... A61M 16/0875 |
| 2005/0028822 A1 | 2/2005 | Sleeper et al. |
| 2006/0174892 A1 | 8/2006 | Leksutin et al. |
| 2008/0264413 A1 * | 10/2008 | Doherty ............ A61M 16/0825 128/202.27 |
| 2009/0044808 A1 | 2/2009 | Guney et al. |
| 2009/0050156 A1 | 2/2009 | Ng et al. |
| 2010/0000534 A1 | 1/2010 | Kooij et al. |
| 2010/0018534 A1 | 1/2010 | Veliss et al. |
| 2010/0307497 A1 | 12/2010 | Busch et al. |
| 2011/0315141 A1 | 12/2011 | Lavi et al. |
| 2012/0167892 A1 | 7/2012 | Matula, Jr. |
| 2013/0263858 A1 | 10/2013 | Ho et al. |
| 2015/0250972 A1 | 9/2015 | Haibach et al. |
| 2015/0335846 A1 | 11/2015 | Romagnoli et al. |
| 2015/0352308 A1 | 12/2015 | Cullen et al. |
| 2018/0064899 A1 | 3/2018 | Ewers et al. |
| 2018/0099113 A1 * | 4/2018 | Bell .................. A61M 16/0683 |
| 2018/0250486 A1 | 9/2018 | Amarasinghe |
| 2019/0125998 A1 | 5/2019 | Baiko |
| 2020/0368477 A1 | 11/2020 | Foong |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO 2014/045245 A1 | 3/2014 |
| WO | WO 2016/067152 A1 | 5/2016 |
| WO | WO 2017/215949 A1 | 12/2017 |
| WO | WO 2018/007966 A1 | 1/2018 |

OTHER PUBLICATIONS

International Search Report and Written Opinion mailed Jul. 9, 2019 in International Application No. PCT/IB2019/052395, 16 pages.
Notification Concerning Transmittal of International Preliminary Report on Patentability mailed Oct. 8, 2020 in International Application No. PCT/IB2019/052395, 8 pages.
U.S. Appl. No. 16/635,267, filed Jan. 30, 2020 of Foong, for "Conduit with Magnetic Connector," (parent application).
Extended European Search Report mailed Jun. 24, 2024 in European Application No. 23210412.5, 15 pages.

* cited by examiner

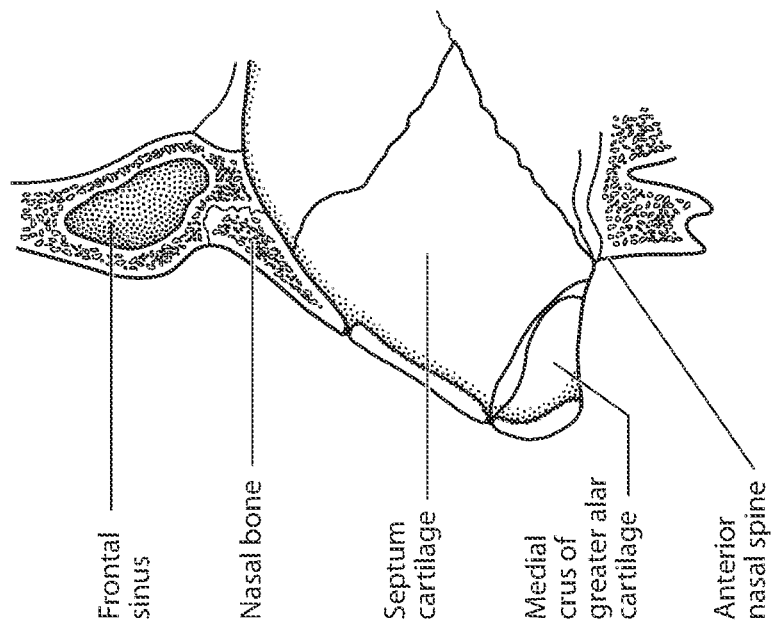
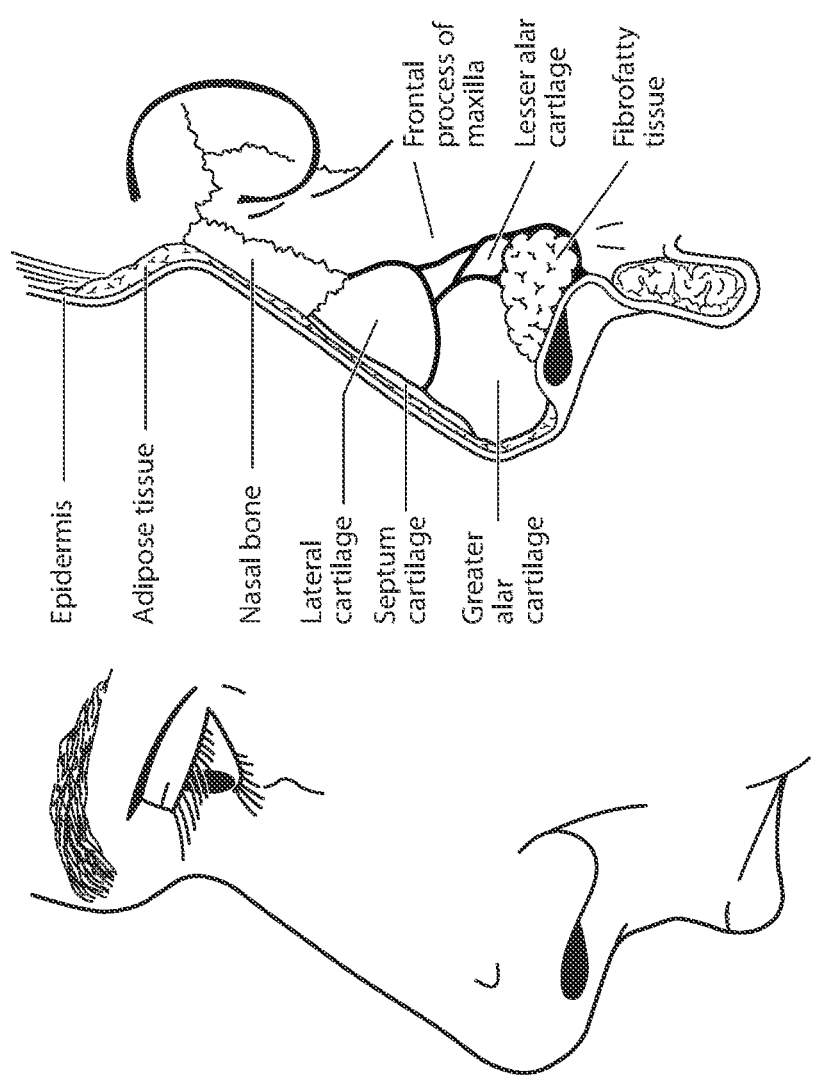
FIG. 2G  FIG. 2H  FIG. 2I

Relatively Large Positive Curvature

Relatively Small Positive Curvature

Zero Curvature

Relatively Small Negative Curvature

Relatively Large Negative Curvature

Left-hand rule  Right-hand rule
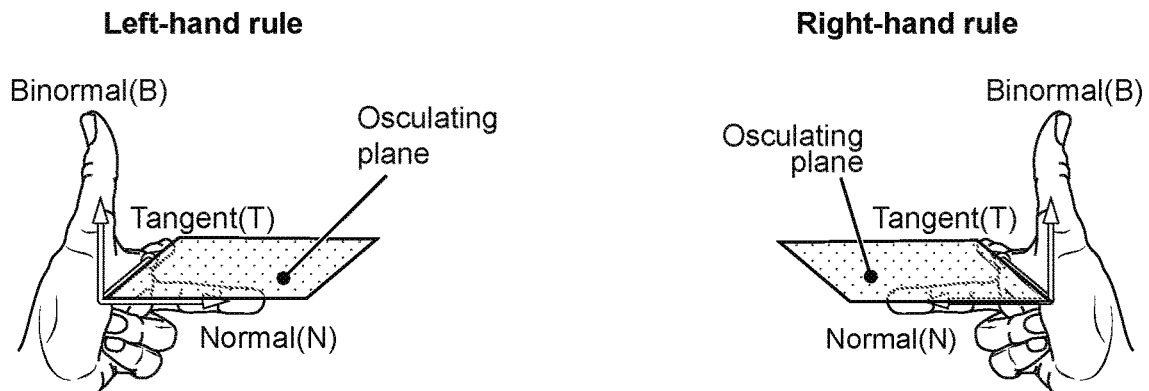
FIG. 3O  FIG. 3P
Left ear helix  Right ear helix
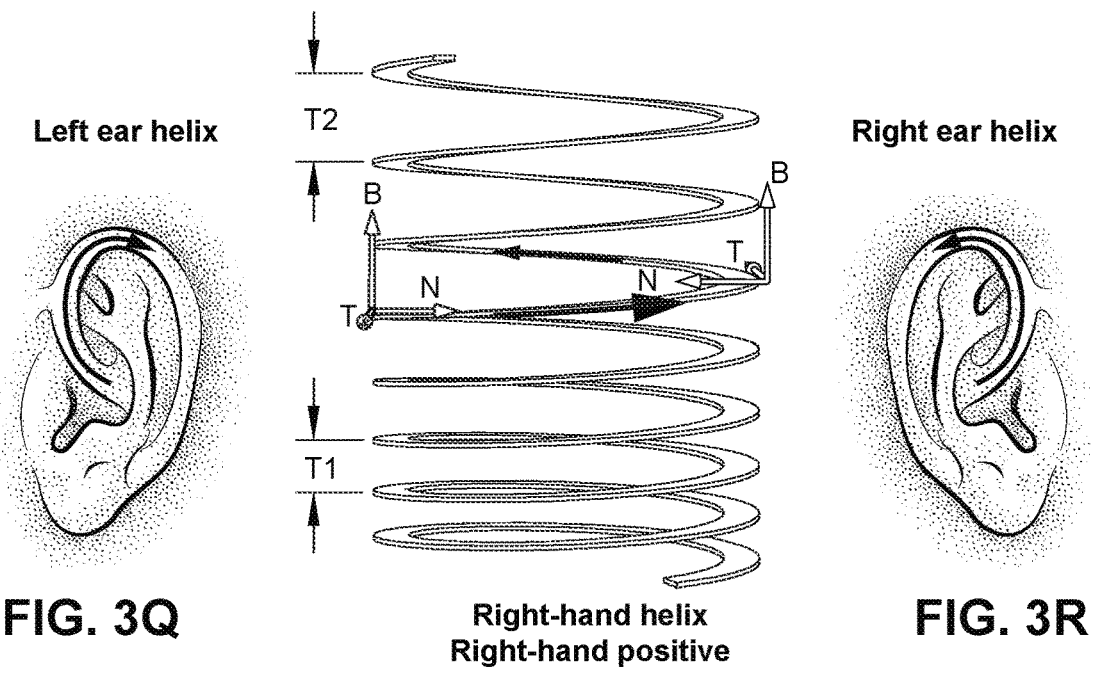
FIG. 3Q  Right-hand helix  FIG. 3R
Right-hand positive
FIG. 3S
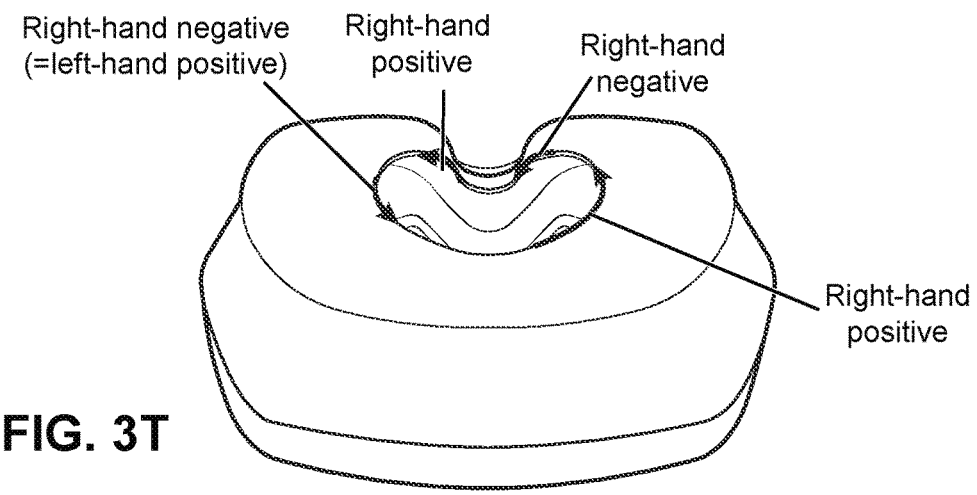
FIG. 3T

CONDUIT WITH MAGNETIC CONNECTOR

1 CROSS-REFERENCE TO RELATED APPLICATIONS

This application is a continuation of U.S. application Ser. No. 16/635,267, filed Jan. 30, 2020, which is the U.S. national phase of International Application No. PCT/IB2019/052395 filed 25 Mar. 2019, which designated the U.S. and claims the benefit of U.S. Provisional Application No. 62/649,941, filed Mar. 29, 2018, the entire contents of each of which are hereby incorporated by reference in their entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY

5.1 Field of the Technology

The present technology relates to one or more of the screening, diagnosis, monitoring, treatment, prevention and amelioration of respiratory-related disorders. The present technology also relates to medical devices or apparatus, and their use.

5.2 Description of the Related Art 5.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See *Respiratory Physiology*, by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

5.2.2 Therapy

Various therapies, such as Continuous Positive Airway Pressure (CPAP) therapy, Non-invasive ventilation (MV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

5.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

5.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

5.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT' nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY" full-face mask); International Patent Application WO 2009/052, 560 (describing amongst other things aspects of the ResMed Limited SWIFT™ FX nasal pillows).

5.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

5.2.3.2 Respiratory Pressure Therapy (RPT) Device

A respiratory pressure therapy (RPT) device may be used individually or as part of a system to implement one or more of a number of therapies described above, such as by operating the device to generate a flow of air for delivery to an interface to the airways. The flow of air may be pressurised. Examples of RPT devices include a CPAP device and a ventilator.

5.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

5.2.3.4 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cmH₂O Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

5.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

6 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a patient interface for delivery of a supply of pressurised breathable gas to an entrance of a patient's airways.

Another aspect of one form of the present technology is a patient interface that is moulded or otherwise constructed with a perimeter shape which is complementary to that of an intended wearer.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of the present technology relates to a patient interface including a mask assembly and a gas conduit to deliver a pressurized flow of air to the mask assembly, and the patient interface includes magnetic connector(s) to connect the conduit to the mask assembly.

An aspect of the present technology relates to a patient interface including a mask assembly and a pressurized gas conduit to at least partially surround the patient's head and deliver a pressurized flow of air to the mask assembly, and the patient interface includes at least one magnetic connector to connect the conduit to the mask assembly and/or headgear.

An aspect of the present technology relates to a patient interface including a mask assembly and a headgear conduit to at least partially support the mask assembly on the patient's head and deliver a pressurized flow of air to the mask assembly, and the patient interface includes magnetic connector(s) to connect the headgear conduit to the mask assembly.

In an example, each magnetic connector may include an opening that forms a channel through which air is directed from the conduit to the mask assembly. In an example, the opening of each magnetic connector may align with a respective opening provided to the plenum chamber of the mask assembly. In an example, each magnetic connector may restrict movement in one or more directions of a single plane. In an example, each magnetic connector may form a sealed connection between the conduit and the mask assembly.

Another aspect of one form of the present technology comprises a patient interface. The patient interface may include plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include a positioning and stabilising structure to provide a force to hold the seal-forming structure in a therapeutically effective position on the patient's head. The positioning and stabilising structure may include a conduit connector assembly configured to deliver the flow of air at the therapeutic pressure. The conduit connector assembly may include a connector opening. The conduit connector assembly may include a connector opening. The conduit connector assembly may form a tie configured to transfer tension force from the position and stabilising structure to the plenum chamber, causing the seal forming structure to press against the face of the patient. The plenum chamber and the conduit connector assembly may be attracted to each other through a magnetic force. A sealed connection may be formed between the plenum chamber and the conduit connector assembly such that air may be configured to pass through the connector opening and the plenum chamber inlet port.

In examples (a) the positioning and stabilising structure may include a second conduit connector assembly with a second connector opening and the plenum chamber includes a second plenum chamber inlet port, wherein the second conduit connector assembly may be configured to engage with the plenum chamber, and wherein air is configured to pass through the second connector opening and the second plenum chamber inlet port, (b) the conduit connector assembly may include a retention member receptor, the retention member receptor includes a groove for receiving a plenum magnet, wherein the plenum magnet is secured between the retention member receptor and a surface of the plenum chamber, (c) the retention member receptor may be formed of elastomeric material, (d) the plenum chamber may include a retention member, wherein the retention member receptor includes an inwardly tapered outer wall, wherein retention member may be inwardly angled so as to lie flush against the inward tapered outer wall of the retention member receptor, (e) in a first orientation the conduit connector assembly may be restricted from movement by the retention member pressing against the retention member receptor in a first direction along a plane, and may be permitted to move in an opposite second direction along the plane in the first orientation, (f) when the conduit connector assembly is engaged with the retention member receptor the conduit connector assembly may be freely rotatable about an axis that extends through the plenum chamber inlet port and the connector opening while maintaining the seal between the plenum chamber and the conduit connector assembly, (g) the plenum chamber may attached to the positioning and stabilising structure only by the conduit connector assembly and a second conduit connector assembly, (h) the patient interface may be configured to allow the patient to breath from ambient through their mouth in the absence of a flow of pressurised air through the plenum chamber inlet port, or the patient interface is configured to leave the patient's mouth uncovered, (i) the plenum chamber and seal-forming structure may be integrally formed, (j) the plenum chamber and the seal-forming structure are formed of the same material, (k) further comprising a seal, wherein the seal may be formed between the retention member and the retention member receptor, (l) the retention member may be separate component from the plenum chamber, (m) the retention member may be integrally formed with the plenum chamber, and (n) the retention member receptor and the retention member may be magnetically attracted to each other.

Another aspect of one form of the present technology comprises a patient interface. The patient interface may include a plenum chamber pressurisable to a therapeutic pressure of at least 6 cmH$_2$O above ambient air pressure, said plenum chamber including a first plenum chamber inlet port and a second plenum chamber inlet port, each being sized and structured to receive a flow of air at the therapeutic pressure for breathing by a patient. The patient interface may include a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include a positioning and stabilising structure to provide a force to hold the seal-forming structure in a therapeutically effective position on the patient's head. The positioning and stabilising structure may comprise a tie. The tie may be constructed and arranged so that at least a portion overlies a region of the patient's head superior to an otobasion superior of the patient's head in use. The first plenum chamber inlet port may include a first plenum chamber magnet with a first polarity and the second plenum chamber inlet port may include a second plenum chamber magnet with a second polarity. The positioning and stabilising structure may include a headgear conduit for directing air to the patient's at the therapeutic pressure. The positioning and stabilising structure may comprise a first conduit connector assembly and a second conduit connector assembly. The first conduit connector assembly may include a first connector magnet with the second polarity and a second connector magnet with the first polarity. The first plenum chamber magnet may be attracted to the first connector magnet and the first plenum chamber magnet may repel the second connector magnet. The second plenum chamber magnet may be attracted to the second connector magnet and the second plenum chamber magnet may repel the first connector magnet. Air may be configured to pass from the first conduit connector assembly through the first plenum chamber inlet port and air may also be configured to pass from the second conduit connector assembly through the second plenum chamber inlet port.

In examples according to the preceding paragraph, (a) the plenum chamber may include a first retention member receptor and a second retention member receptor, the first conduit connector assembly may be configured to engage with the first retention member receptor and the second conduit connector assembly configured to engage with the second retention member receptor, wherein when the first conduit connector assembly is engaged with the first retention member receptor and the second conduit connector assembly is engaged with the second retention member receptor, the plenum chamber is secured by the first conduit connector assembly and the second conduit connector assembly and is configured to receive air through the first conduit connector assembly and the second conduit connector assembly, (b) the first conduit connector assembly may include a retention member, wherein the retention member may be configured to engage with a first retention member receptor of the plenum chamber such that when the retention member is engaged with the first retention member receptor of the plenum chamber the first conduit connector assembly may be restricted from laterally moving in a first direction within a plane and may be permitted to laterally move in an opposite second direction within the plane, (c) the first conduit connector assembly may include a first connector opening, and when the first conduit connector assembly is arranged against the plenum chamber the first conduit connector assembly may be permitted to freely rotate about an axis that extends through the first plenum chamber inlet port and the first connector opening, (d) the first conduit connector assembly may include a first connector opening that is surrounded by the first connector magnet, wherein a magnetic field between the first connector magnet and the first plenum chamber magnet self-aligns the first connector opening with the first plenum chamber inlet port, and (e) a seal forming material may be located between the first plenum chamber magnet and the first connector magnet such that an air-tight seal is formed between the first plenum chamber magnet and the first connector magnet.

Another aspect of one form of the present technology comprises a system. The system may comprise an RPT device and a patient interface, and an air circuit connecting the RPT device to the patient interface. The RPT device may be configured to supply air at positive pressure for respiratory therapy. The air circuit may be connected to the patient interface at a connection port. The patient interface may include a positioning and stabilising structure and a mask assembly, the positioning and stabilising structure including a headgear conduit for receiving a therapeutic pressure of at least 6 cmH$_2$O above ambient air pressure from the air circuit, the headgear conduit extending along a crown of the patient's head from a first parietal bone to a second parietal bone. The headgear conduit may include a first end with a first conduit connector assembly. The mask assembly may be pressurisable to the therapeutic pressure. The mask assembly may include a plenum chamber and a seal forming structure. The plenum chamber may include a plenum chamber opening sized and structured to receive a flow of air at the therapeutic pressure for breathing by a patient. The plenum chamber may include a first plenum chamber receptor assembly. The seal forming structure may be constructed and arranged to form a seal with a region of the patient's face surrounding an entrance to the patient's airways. The seal forming structure may have a hole therein such that the flow of air at said therapeutic pressure is delivered to at least an entrance to the patient's nares. The seal forming structure may be constructed and arranged to maintain said therapeutic pressure in the mask assembly throughout the patient's respiratory cycle in use. The headgear conduit may be configured to deliver air through the first conduit connector assembly and through the first plenum chamber receptor assembly. The first conduit connector assembly may be configured to engage with the first plenum chamber receptor assembly, and be rotatable about an axis that extends through the first plenum chamber receptor assembly. When the first conduit connector assembly is engaged with the first plenum chamber receptor assembly the first conduit connector assembly may be restricted from translating in a first direction perpendicular to the axis, and may be permitted to translate in an opposite second direction.

In examples according to the preceding paragraph, (a) the plenum chamber and the first conduit connector assembly may be attracted to each other through a magnetic force, a seal may be formed between the plenum chamber and the first conduit connector assembly, (b) the first conduit connector assembly may include a connector opening wherein the magnetic force self-aligns the connector opening with the plenum chamber opening, (c) when the patient interface is worn by the patient the first conduit connector assembly is a tie and may provide a posterior force to the mask assembly, (d) the first conduit connector assembly may be configured to be rotatable about the first plenum chamber receptor assembly while maintaining a seal between the first conduit connector assembly and the first plenum chamber receptor assembly, (e) the headgear conduit may further comprise a second end with a second conduit connector assembly and the mask assembly may include a second plenum chamber receptor assembly, wherein the second conduit connector assembly may be configured to engage with the second plenum chamber receptor assembly, wherein air is configured to pass through the second conduit connector assembly and through the second plenum chamber receptor assembly, and (f) the first conduit connector assembly may include a retention member, and wherein the first plenum chamber receptor assembly may include a tapered outer wall, wherein the retention member may be angled to engage with the outer wall of the first plenum chamber receptor assembly, wherein an inner surface of the retention member may be substantially linear and an outer surface of the outer wall is substantially linear.

Another aspect of one form of the present technology comprises a patient interface to provide a flow of air pressurized above ambient to a patient's upper airways sufficient to treat sleep-disordered breathing. The patient interface may include a cushion assembly including a cushion inlet port to receive a flow of air for breathing by the patient. The patient interface may include at least one inlet conduit to at least partially support and position the cushion assembly on the patient's head. The inlet conduit may be configured to deliver the pressurized flow of air to the cushion inlet port. The patient interface may comprise a magnetic connector to magnetically connect the at least one inlet conduit to the cushion assembly. The magnetic connector may comprise an intermediate air flow path that pneumatically connects the at least one inlet conduit to the cushion inlet port.

In examples according to the preceding paragraph, (a) further comprising a retention member that detachably interfaces with the cushion assembly, the retention member may be structured and positioned to at least partially counteract tension forces tending to separate the at least one inlet conduit from the cushion assembly, and (b) further comprising a magnetic retaining member to assist in maintaining a sealing contact between the at least one inlet conduit and the cushion inlet port.

Another aspect of one form of the present technology comprises a patient interface. The patient interface may include a plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include a headgear to provide a force to hold the seal-forming structure in a therapeutically effective position on the patient's head. The patient interface may be configured to allow the patient to breath from ambient through their mouth in the absence of a flow of pressurised air through the plenum chamber inlet port, or the patient interface may be configured to leave the patient's mouth uncovered. The patient interface may comprise a mask assembly. The mask assembly may comprise a shell assembly and the seal forming structure, the plenum chamber inlet port located in the shell assembly adjacent an anchor receptor, the shell assembly being magnetized with a first polarity. The headgear may include a conduit connector assembly. The conduit connector assembly may include a connector opening. The conduit connector assembly may be magnetized with a second polarity. The conduit connector assembly may include an anchor. Tension force may be transferred from the headgear to the conduit connector assembly such that the anchor presses against the anchor receptor, causing the seal forming structure to press against the face of the patient. The shell assembly and the conduit connector assembly may be attracted to each other through a magnetic force forming a seal between the shell assembly and the conduit connector assembly, and wherein air is configured to pass through the connector opening and the plenum chamber inlet port.

In examples, (a) the headgear may include a second conduit connector assembly with a second connector opening and the shell assembly may include a second plenum chamber inlet port and a second anchor receptor, the second conduit connector assembly may be configured to engage with the second anchor receptor, and air may be configured to pass through the second connector opening and the second plenum chamber inlet port, (b) the anchor receptor may include a groove for receiving a shell magnet, wherein the shell magnet may be secured between the anchor receptor and a shell of the shell assembly, (c) the anchor receptor may be formed of rubber material, (d) the anchor receptor may include an inwardly tapered outer wall, wherein anchor may be inwardly angled so as to lie flush against the inward tapered outer wall of the anchor receptor, (e) in a first orientation the conduit connector assembly may be restricted from movement by the anchor pressing against the anchor receptor in a first direction along a plane, and may be permitted to move in an opposite second direction along the plane in the first orientation, (f) the mask assembly may be attached to the headgear only by the conduit connector assembly and a second conduit connector assembly, and (g) when the conduit connector assembly is positioned against the anchor receptor the conduit connector assembly may be freely rotatable about an axis that extends through the plenum chamber inlet port and the connector opening while maintaining the seal between the shell assembly and the conduit connector assembly.

Another aspect of one form of the present technology comprises a patient interface. The patient interface may include a plenum chamber pressurisable to a therapeutic pressure of at least 6 cmH$_2$O above ambient air pressure. The plenum chamber may include a first plenum chamber inlet port and a second plenum chamber inlet port, each being sized and structured to receive a flow of air at the therapeutic pressure for breathing by a patient. The patient interface may include a seal-forming structure constructed and arranged to form a seal with a region of the patient's face surrounding an entrance to the patient's airways. The seal-forming structure may have a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include a headgear to provide a force to hold the seal-forming structure in a therapeutically effective position on the patient's head. The patient interface may be configured to allow the patient to breath from ambient through their mouth in the absence of a flow of pressurised air through the first plenum chamber inlet port or second plenum chamber inlet port, or the patient interface may be configured to leave the patient's mouth uncovered. The first plenum chamber inlet port may include a first shell magnet with a first polarity and the second plenum chamber inlet port may include a second shell magnet with a second polarity. The headgear may include a headgear conduit for directing air to the patient's airways. The headgear may comprise a first conduit connector assembly and a second conduit connector assembly. The first conduit connector assembly may include a first connector magnet with the second polarity and a second connector magnet with the first polarity. The first shell magnet may be attracted to the first connector magnet and the first shell magnet may repel the second connector magnet. The second shell magnet may be attracted to the second connector magnet and the second shell magnet may repel the first connector magnet. Air may be configured to pass from the first conduit connector assembly through the first plenum chamber inlet port and air may also be configured to pass from the second conduit connector assembly through the second plenum chamber inlet port.

In examples, (a) the plenum chamber may include a first anchor receptor and a second anchor receptor, the first conduit connector assembly may be configured to engage with the first anchor receptor and the second conduit connector assembly configured to engage with the second anchor receptor, wherein when the first conduit connector assembly may be engaged with the first anchor receptor and the second conduit connector assembly may be engaged with the second anchor receptor, the plenum chamber is secured by the first conduit connector assembly and the second conduit connector assembly and may be configured to receive air through the first conduit connector assembly and the second conduit connector assembly, (b) the first conduit connector assembly may include an anchor, wherein the anchor is configured to engage with a first anchor receptor of the plenum chamber such that when the anchor is engaged with the first anchor receptor of the plenum chamber the first conduit connector assembly may be restricted from laterally moving in a first direction within a plane and may be permitted to laterally move in an opposite second direction within the plane, (c) the first conduit connector assembly may include a first connector opening, and when the first conduit connector assembly is arranged against the plenum chamber the first conduit connector assembly may be permitted to freely rotate about an axis that extends through the first plenum chamber inlet port and the first connector opening, (d) the first conduit connector assembly may include a first connector opening that is surrounded by the first connector magnet, wherein a magnetic field between the first connector magnet and the first shell magnet may self-align the first connector opening with the first plenum chamber inlet port, and (e) a seal forming material may located between the first shell magnet and the first connector magnet such that an air-tight seal is formed between the first shell magnet and the first connector magnet.

Another aspect of one form of the present technology comprises a system. The system may comprise an RPT device and a patient interface, and an air circuit connecting the RPT device to the patient interface. The RPT device may be configured to supply air at positive pressure for respiratory therapy. The air circuit may be connected to the patient interface at a connection port. The patient interface may include a headgear and a mask assembly. The headgear may include a headgear conduit for receiving air from the air circuit. The headgear conduit may extend along a crown of the patient's head from a first side of the parietal bone to a second side of the parietal bone. The headgear conduit may include a first end with a first conduit connector assembly. The mask assembly may be pressurisable to a therapeutic pressure of at least 6 cmH$_2$O above ambient air pressure. The mask assembly may include a shell assembly and a seal forming structure. The shell assembly may include a shell opening sized and structured to receive a flow of air at the therapeutic pressure for breathing by a patient. The shell assembly may include a first shell receptor assembly. The seal forming structure may be constructed and arranged to form a seal with a region of the patient's face surrounding an entrance to the patient's airways. The seal forming structure may have a hole therein such that the flow of air at said therapeutic pressure is delivered to at least an entrance to the patient's nares. The seal forming structure may be constructed and arranged to maintain said therapeutic pressure in the mask assembly throughout the patient's respiratory cycle in use. The headgear conduit may be configured to deliver air through the first conduit connector assembly and through the first shell receptor assembly. The first conduit connector assembly may be configured to engage with the first shell receptor assembly and may be rotatable about an axis that extends through the shell receptor assembly. When the first conduit connector assembly is engaged with the first shell receptor assembly the first conduit connector assembly may be restricted from translating in a first direction perpendicular to the axis, and may be permitted to translate in an opposite second direction.

In examples according to the preceding paragraph, (a) the shell assembly and the first conduit connector assembly may be attracted to each other through a magnetic force forming a seal between the shell assembly and the first conduit connector assembly, (b) the first conduit connector assembly may include a connector opening wherein the magnetic force self-aligns the connector opening with the shell opening, (c) when the patient interface is worn by the patient the first conduit connector assembly may provide a posterior force to the mask assembly, (d) the first conduit connector assembly may be configured to be rotatable about the first shell receptor assembly while maintaining a seal between the first conduit connector assembly and the first shell receptor assembly, (e) the headgear conduit may further comprise a second end with a second conduit connector assembly and the mask assembly may include a second shell receptor assembly, wherein the second conduit connector assembly may be configured to engage with the second shell receptor assembly, wherein air is configured to pass through the second conduit connector assembly and through the second shell receptor assembly, (f) the first conduit connector assembly may include an anchor, and wherein the first shell receptor assembly includes a tapered outer wall, wherein the anchor is angled to engage with the outer wall of the first shell receptor assembly, wherein an inner surface of the anchor may be substantially linear and an outer surface of the outer wall may be substantially linear.

Another aspect of one form of the present technology comprises a patient interface for providing a flow of air pressurized above ambient to a patient's upper airways sufficient to treat sleep-disordered breathing. The patient interface may comprise a cushion assembly including a cushion inlet port to receive a flow of air for breathing by the patient. The patient interface may comprise least one inlet conduit to at least partially support and position the cushion on the patient's head, the inlet conduit being configured to deliver the pressurized flow of air to the inlet port. The patient interface may comprise a magnetic connector to magnetically connect the at least one inlet conduit to the cushion assembly. The magnetic connector may comprise an intermediate air flow path that pneumatically connects the at least one air inlet conduit to the cushion inlet port.

In examples according to the preceding paragraph, the patient interface may further include (a) an anchor member that detachably interfaces with the cushion assembly, the anchor member may be structured and positioned to at least partially counteract tension forces tending to separate the at least one conduit from the cushion assembly, and/or (b) a magnetic retaining member to assist in maintaining a sealing contact between the at least one inlet conduit and the inlet port.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

7.2 Respiratory System and Facial Anatomy

Figure 2A:
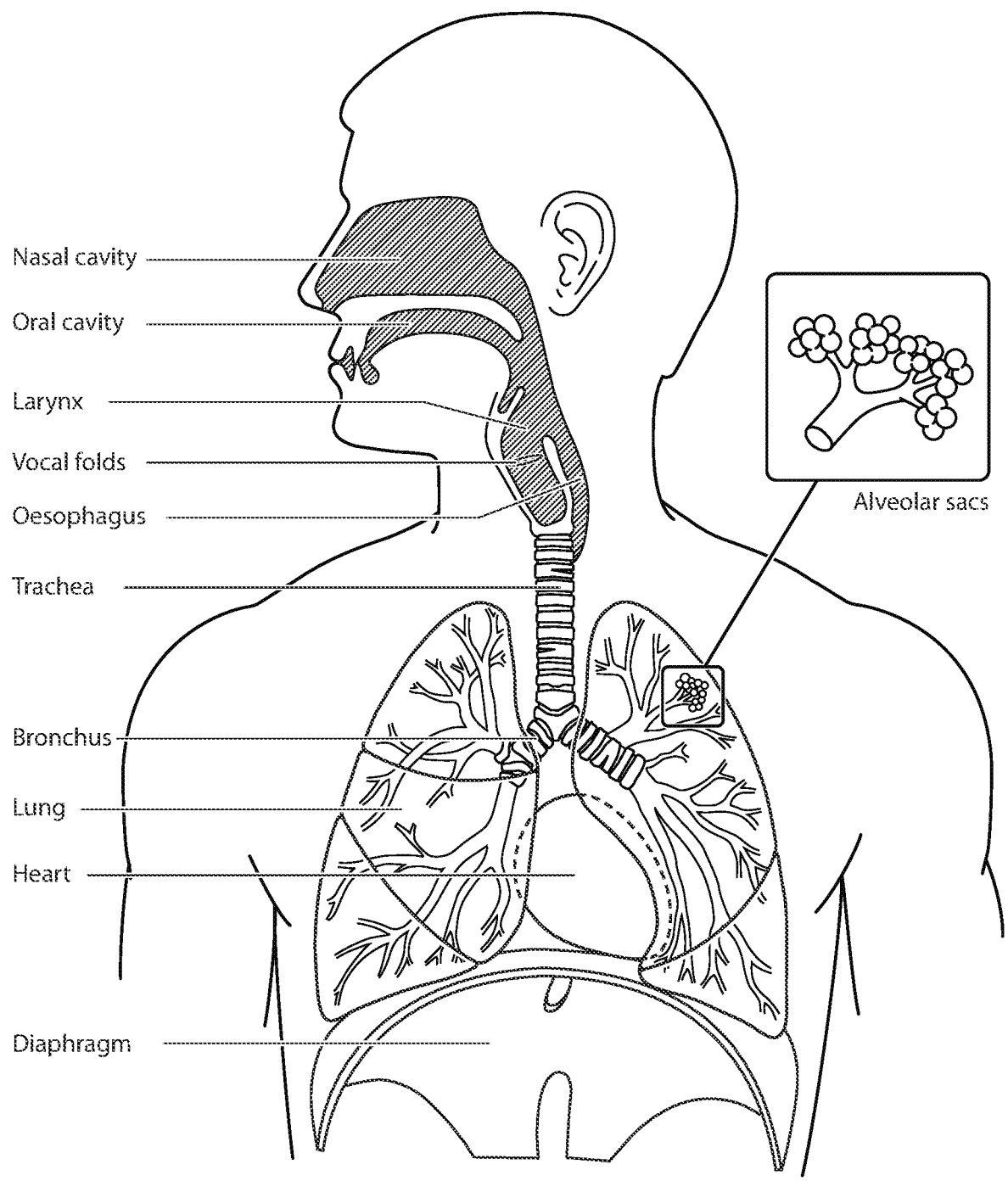
FIG. 2A shows an overview of a human respiratory system including the nasal and oral cavities, the larynx, vocal folds, oesophagus, trachea, bronchus, lung, alveolar sacs, heart and diaphragm.
Figure 2B:
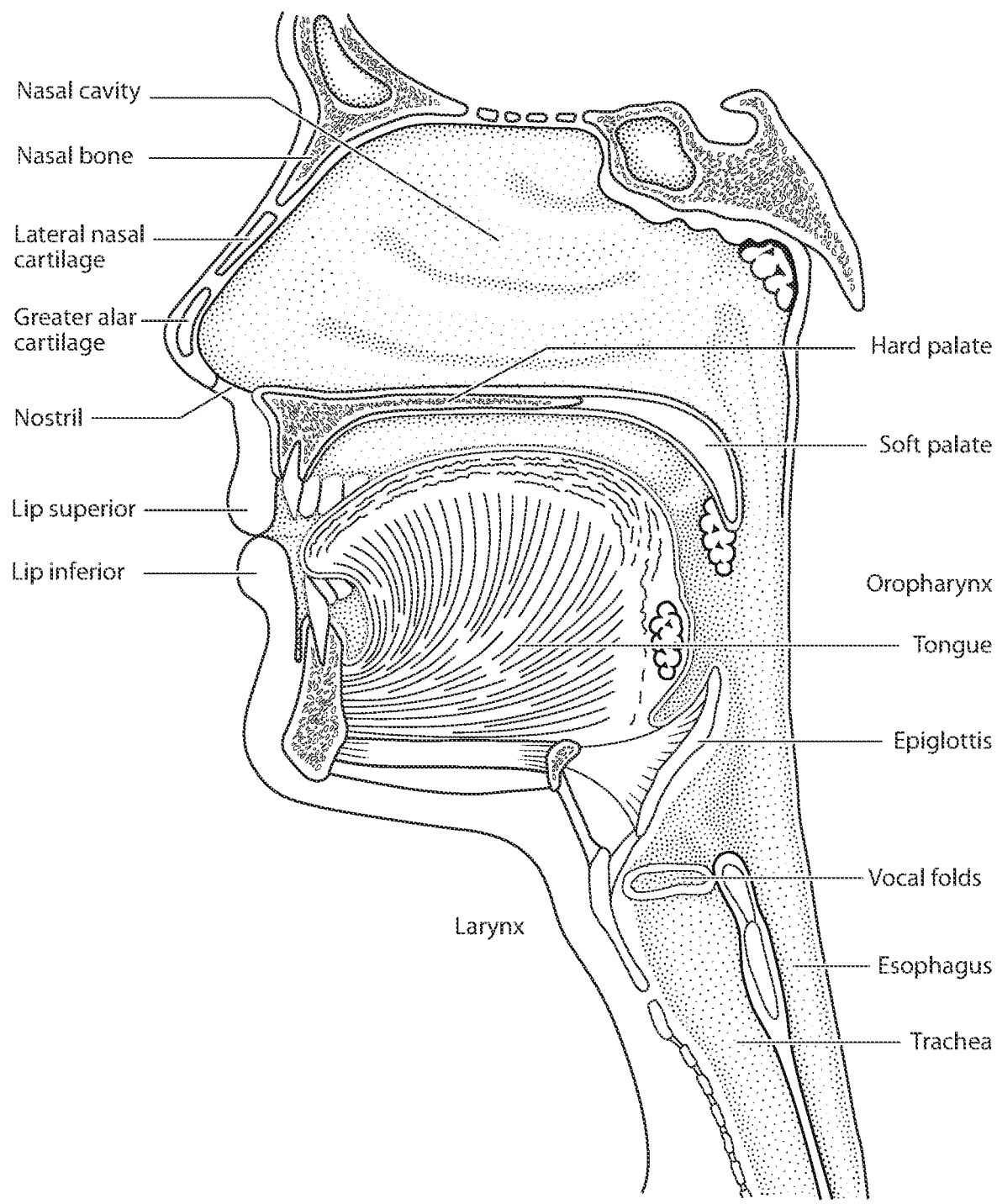
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
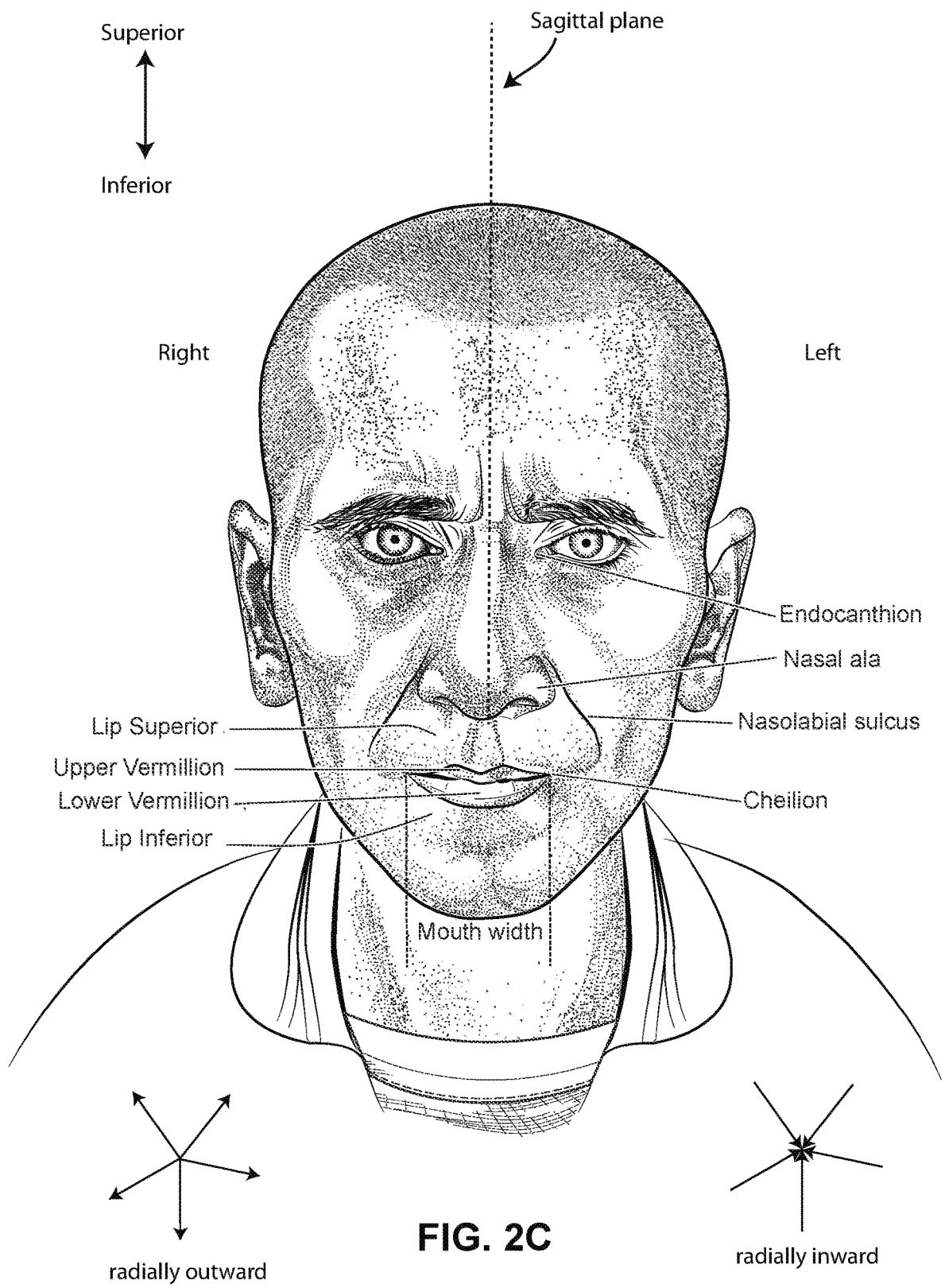
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
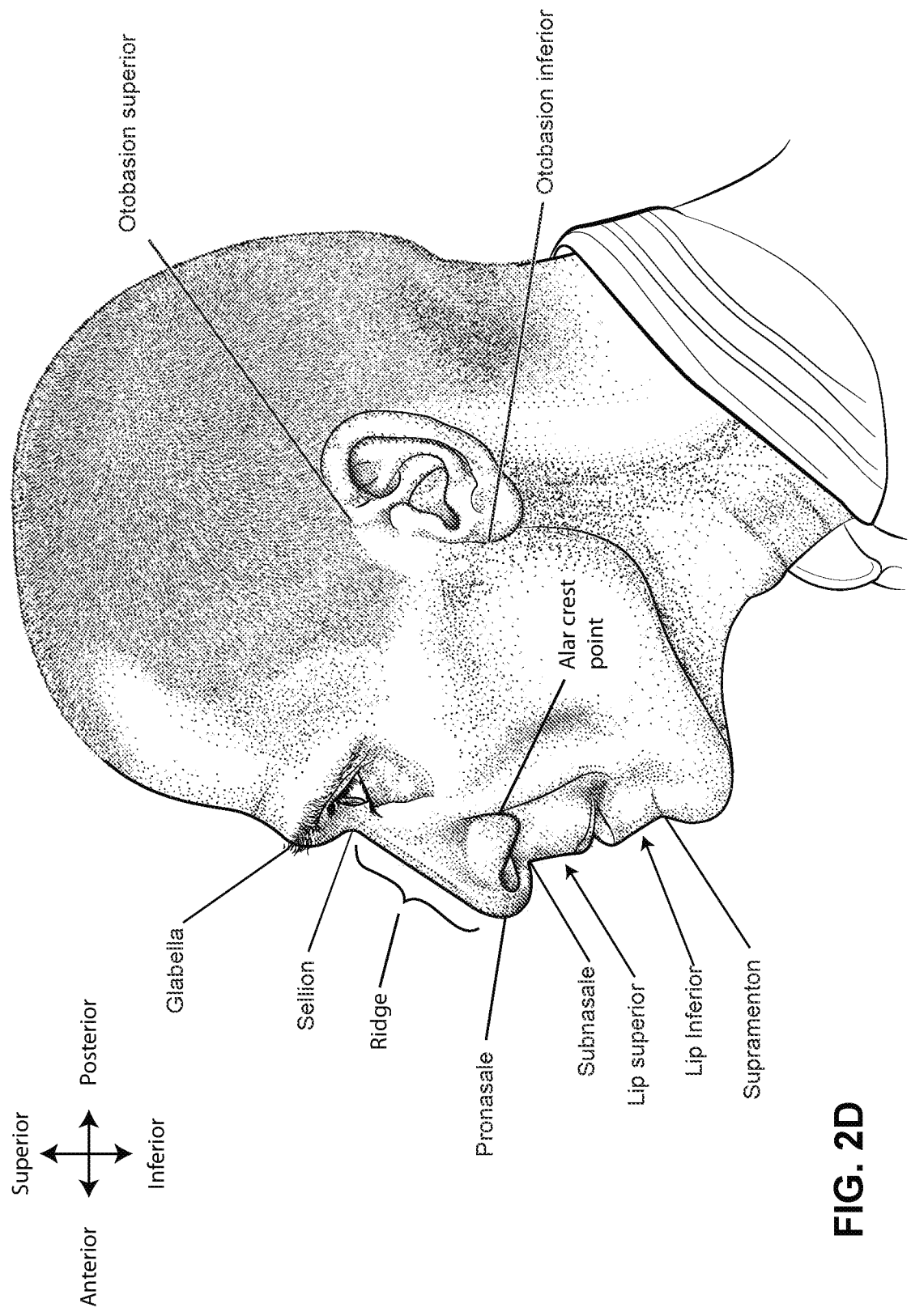
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
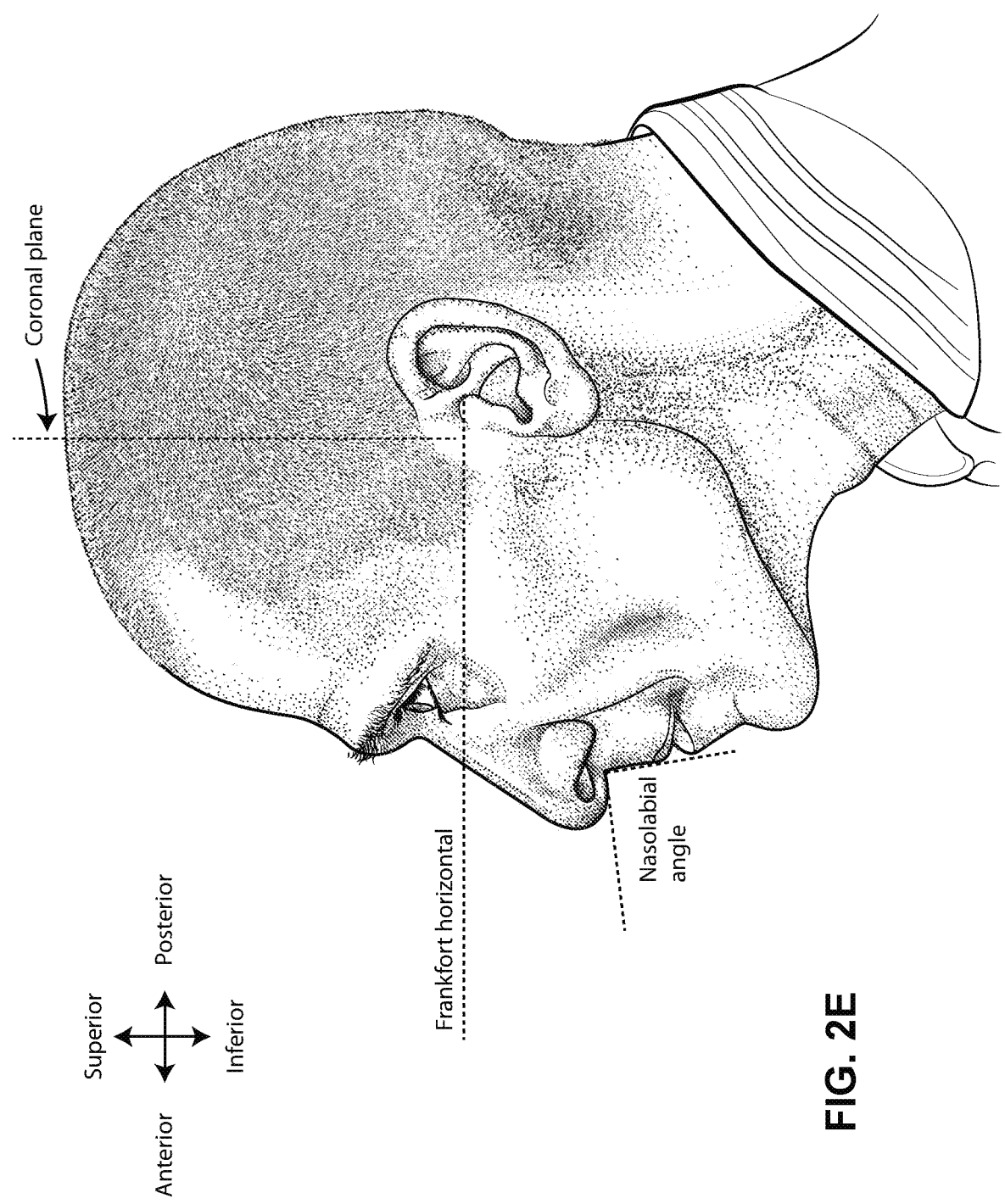

FIG. 2E is a further side view of a head. The approximate locations of the Frankfort horizontal and nasolabial angle are indicated. The coronal plane is also indicated.

Figure 2F:
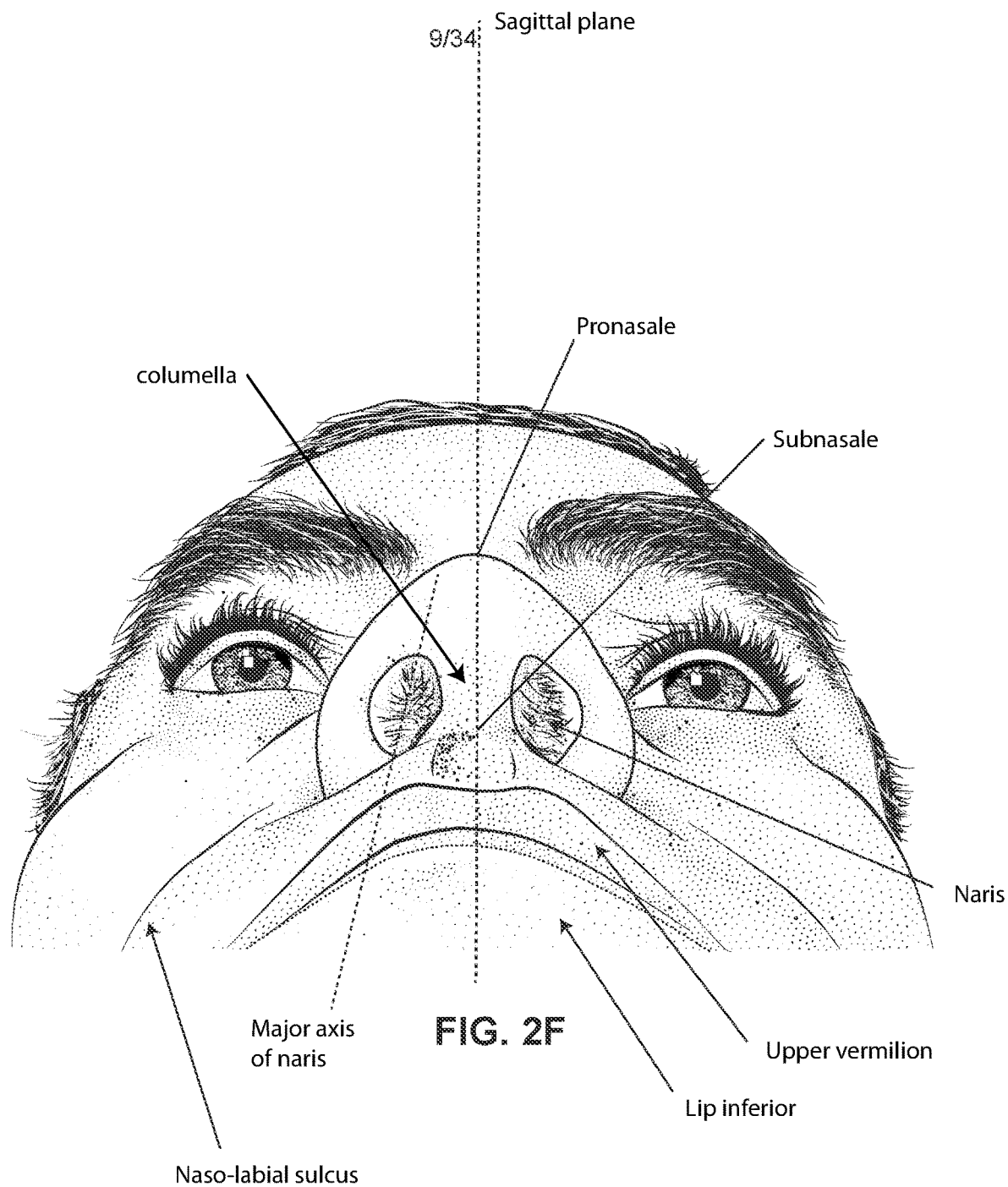

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
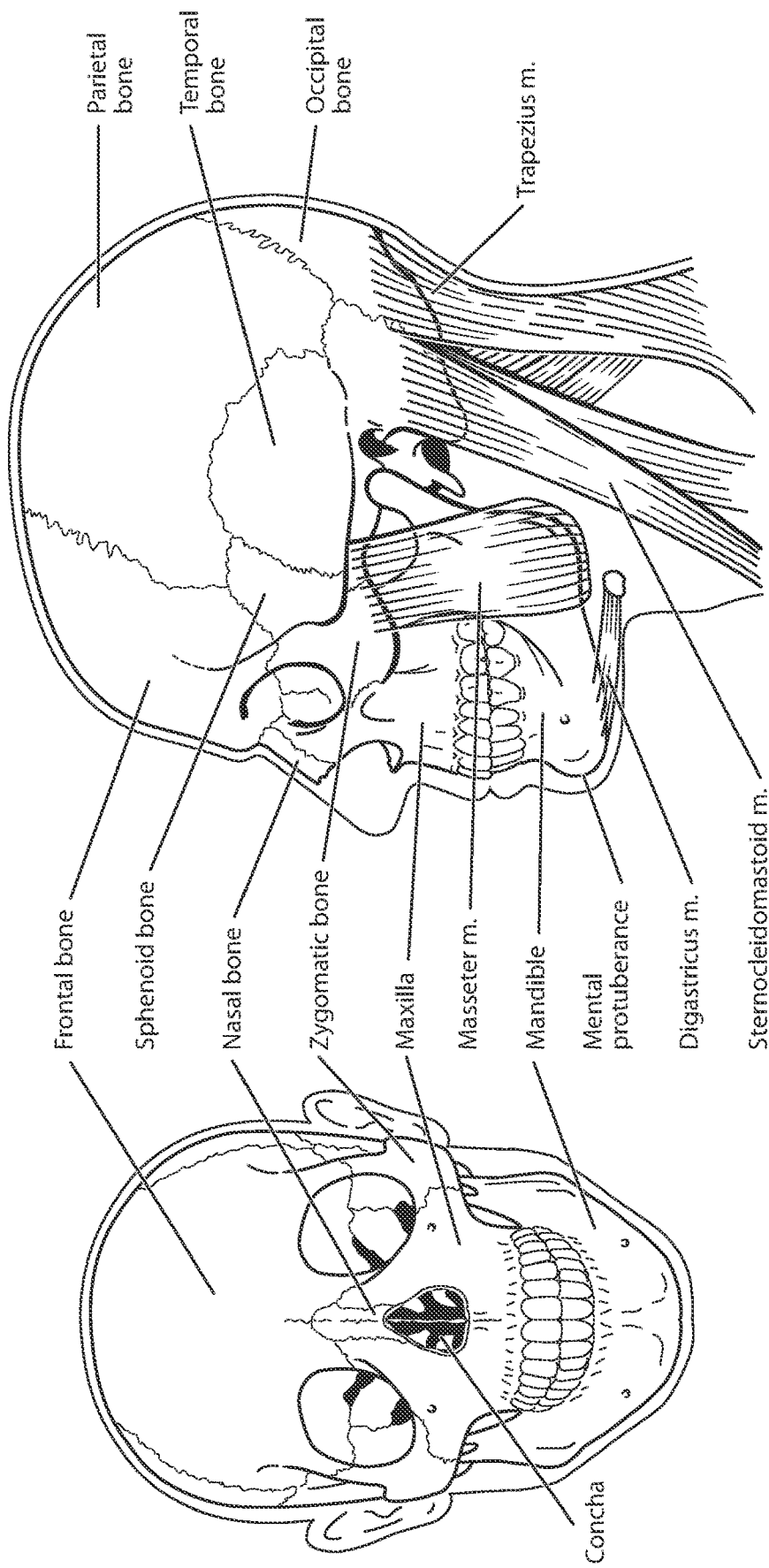

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
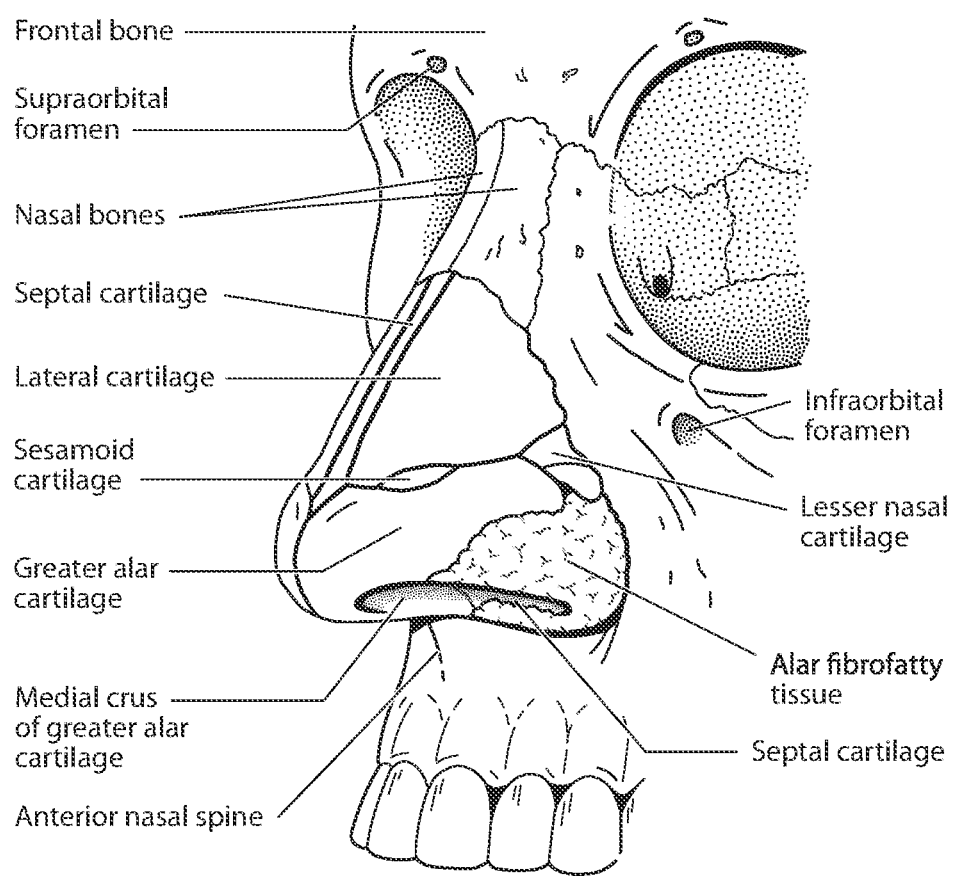

FIG. 2L shows an anterolateral view of a nose.

7.3 Patient Interface

Figure 3A:
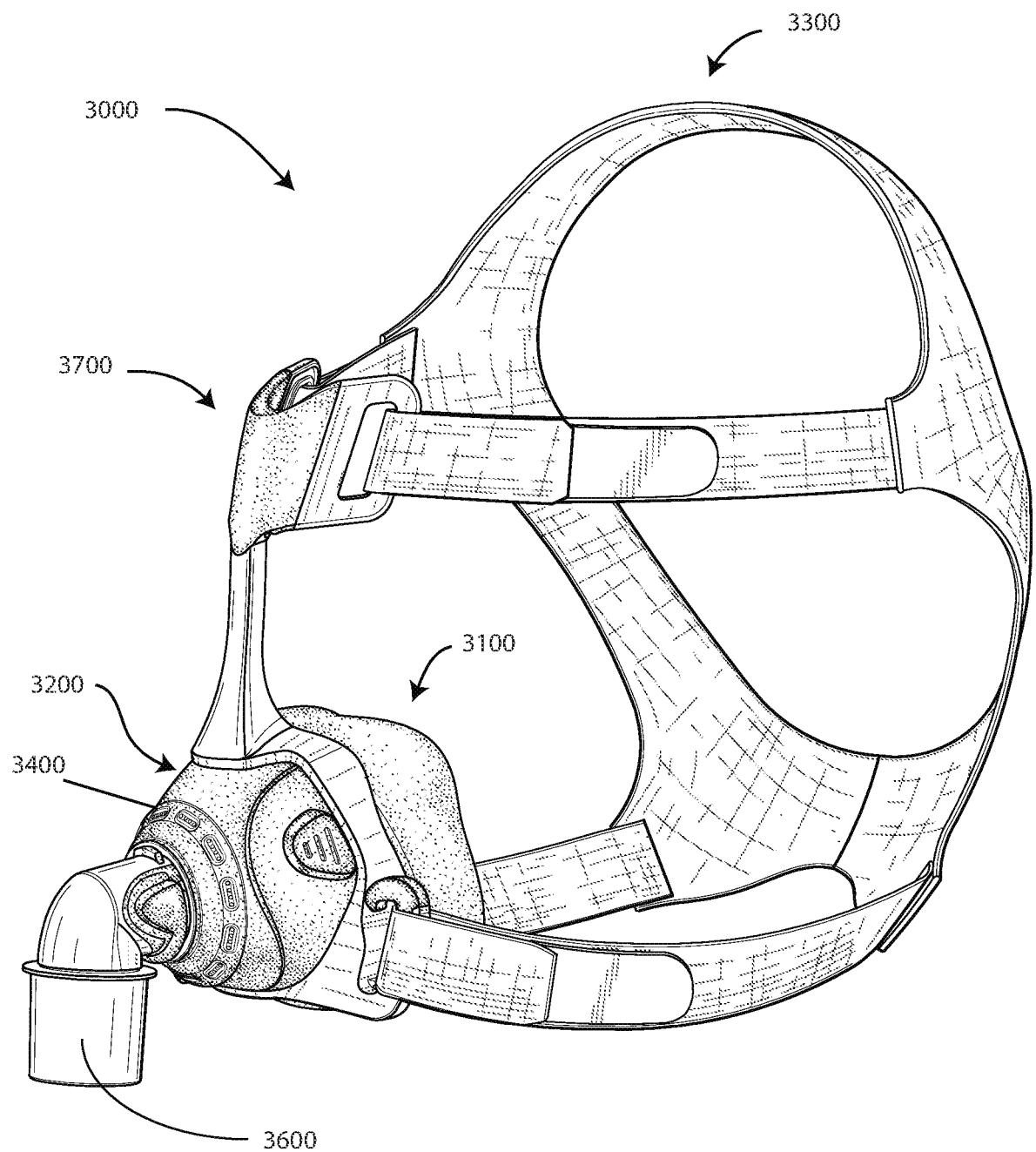

FIG. 3A shows a patient interface in the form of a nasal mask in accordance with one form of the present technology.

Figure 3B:
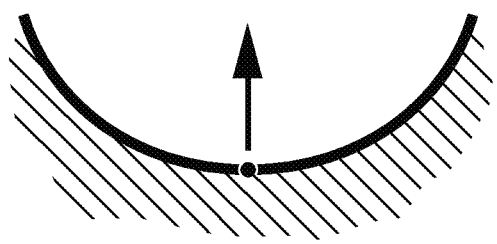

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
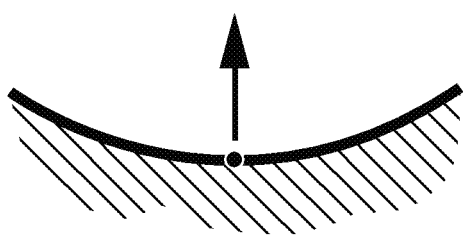

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
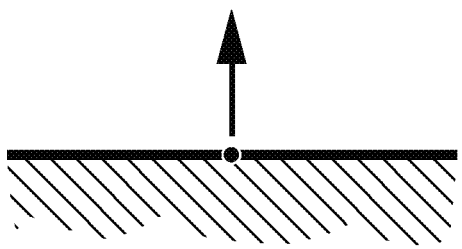

FIG. 3D shows a schematic of a cross-section through a structure at a point. An outward normal at the point is indicated. The curvature at the point has a value of zero.

Figure 3E:
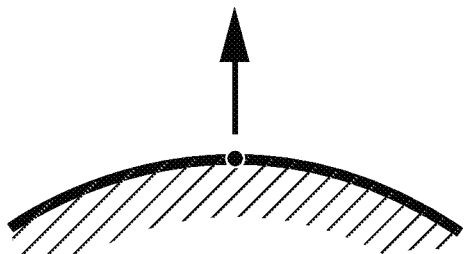

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
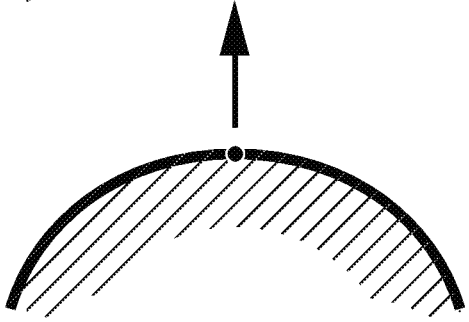

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
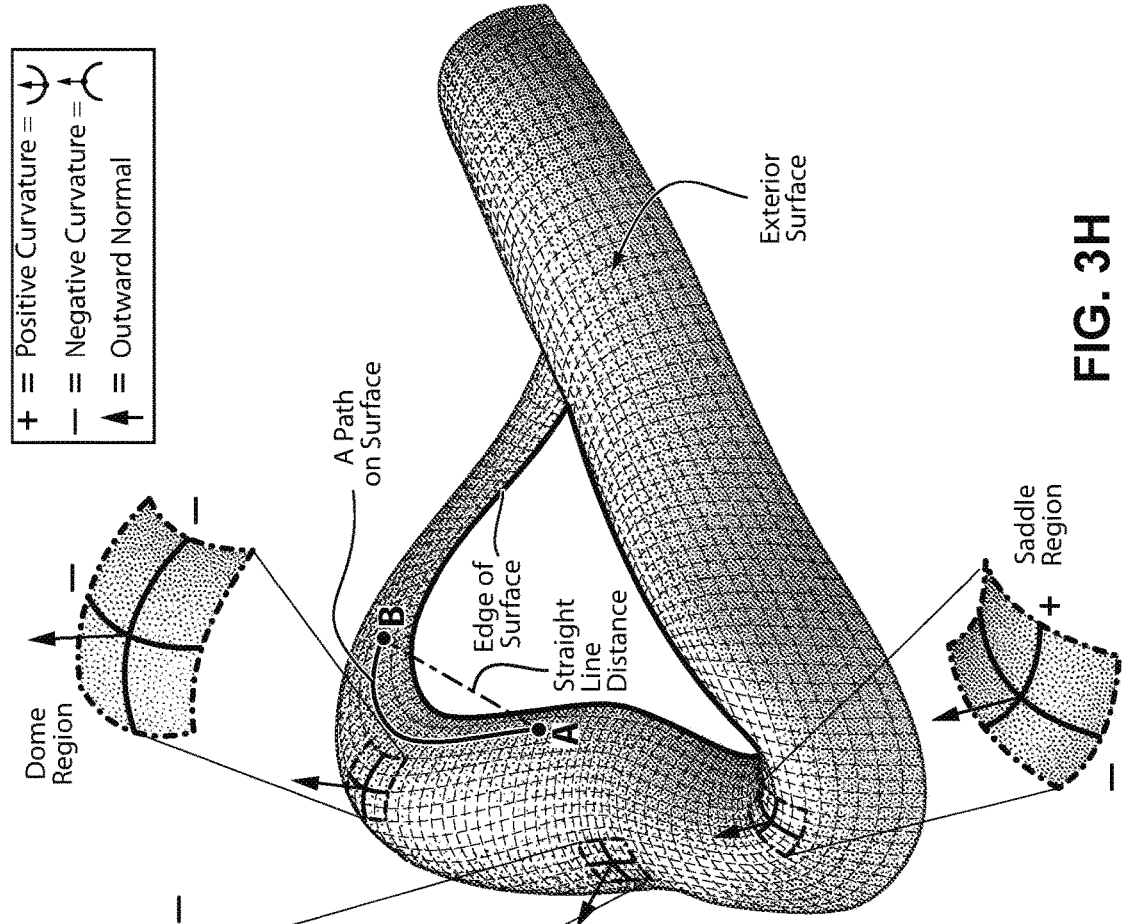
Figure 3G:
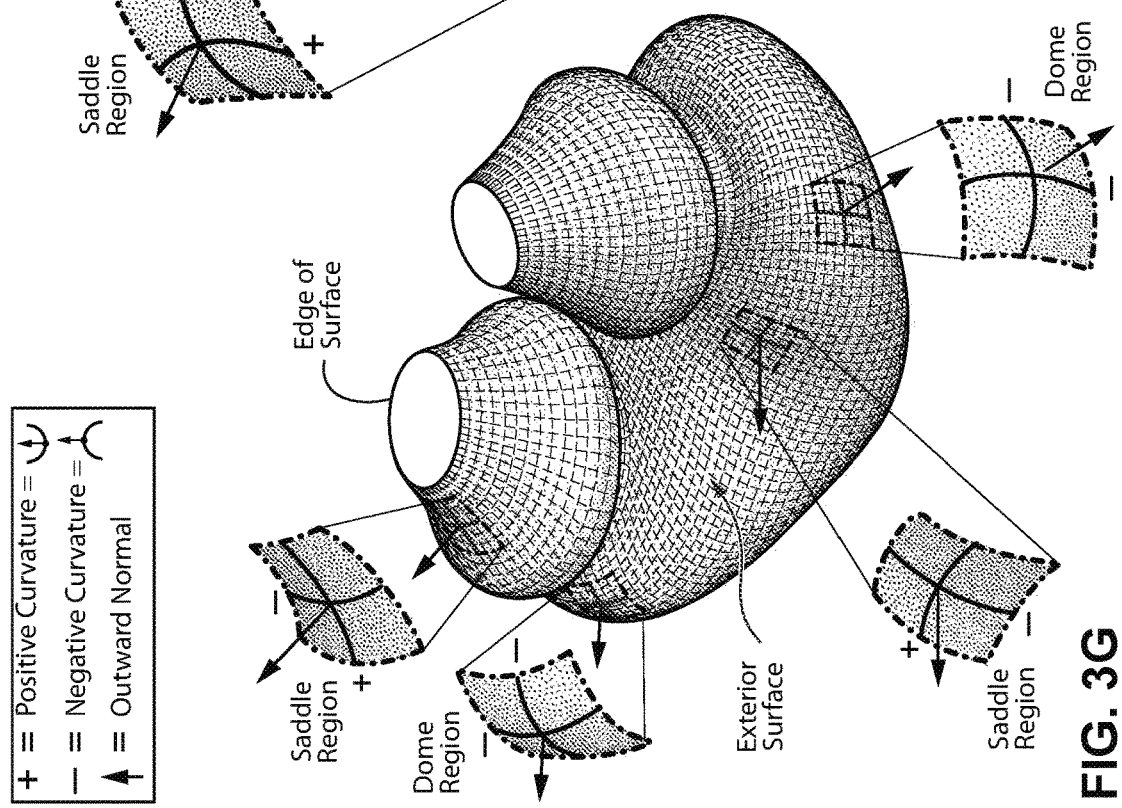

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
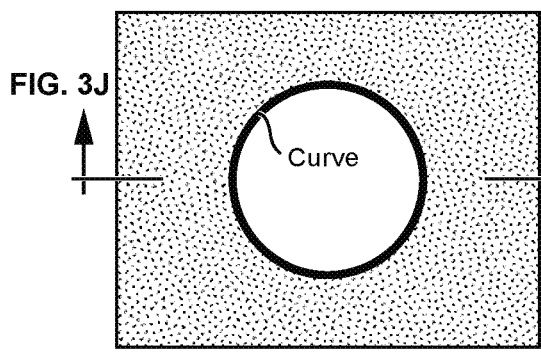

FIG. 3I shows the surface of a structure, with a one dimensional hole in the surface. The illustrated plane curve forms the boundary of a one dimensional hole.

Figure 3K:
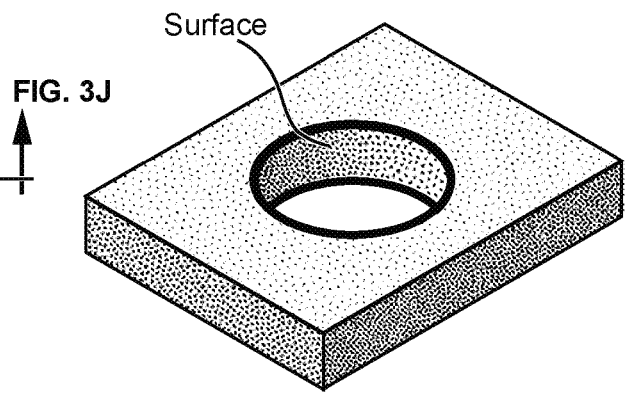
Figure 3J:
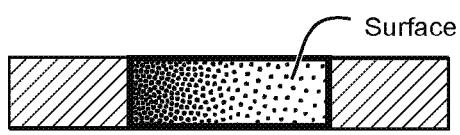

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
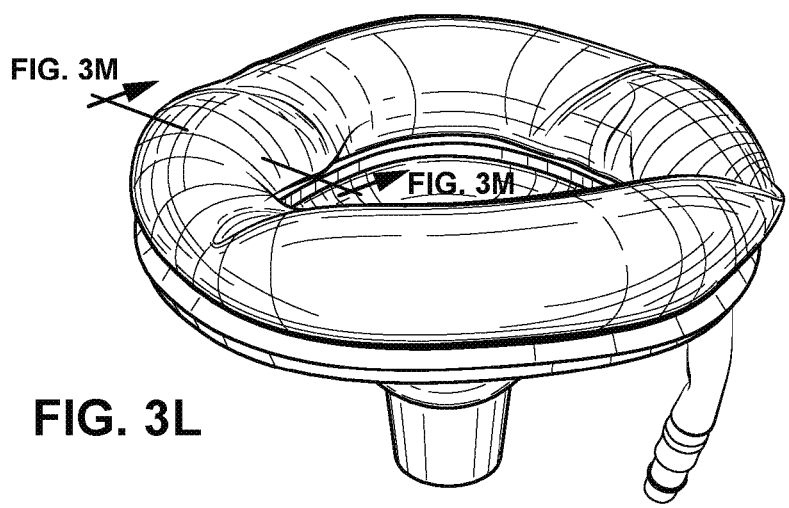

FIG. 3L shows a mask having an inflatable bladder as a cushion.

Figures 3M, 3N:
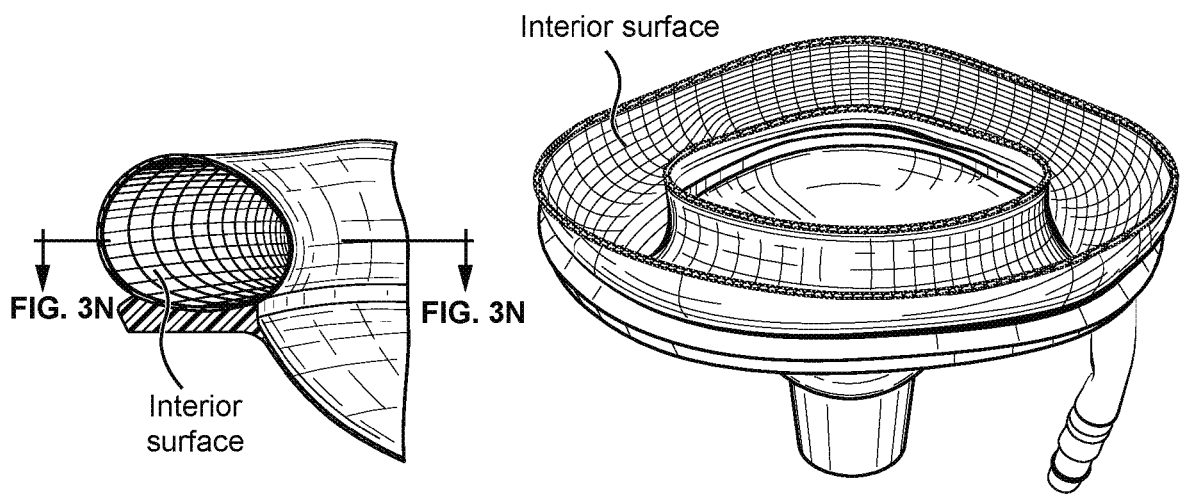

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
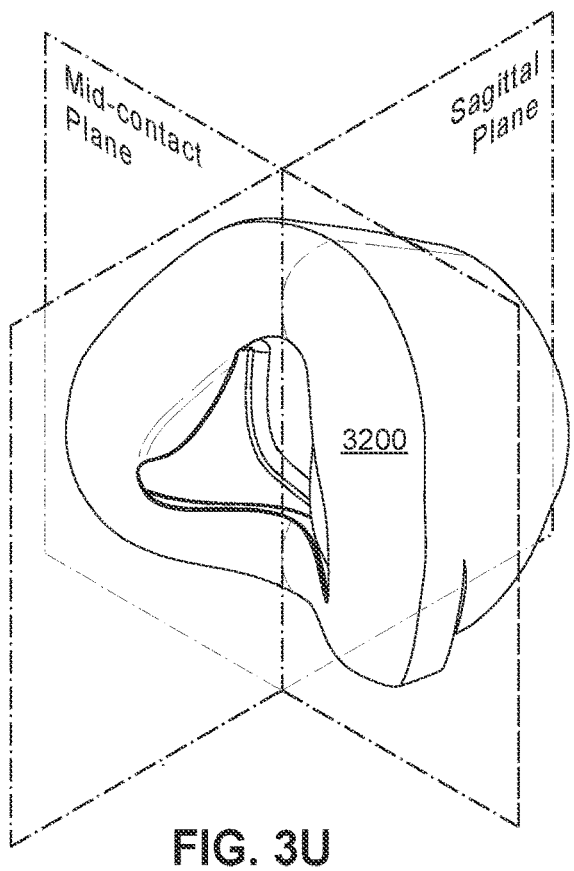

FIG. 3U shows a view of a plenum chamber 3200 showing a sagittal plane and a mid-contact plane.

Figure 3V:
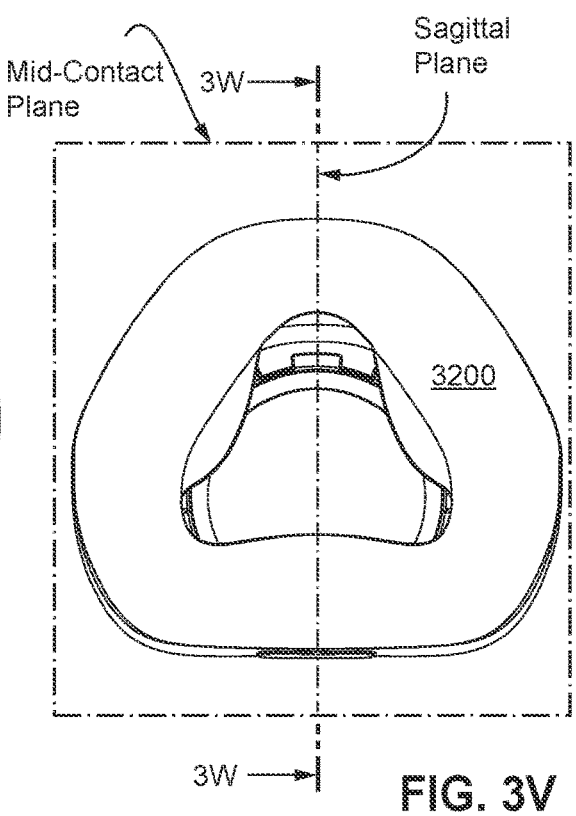

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
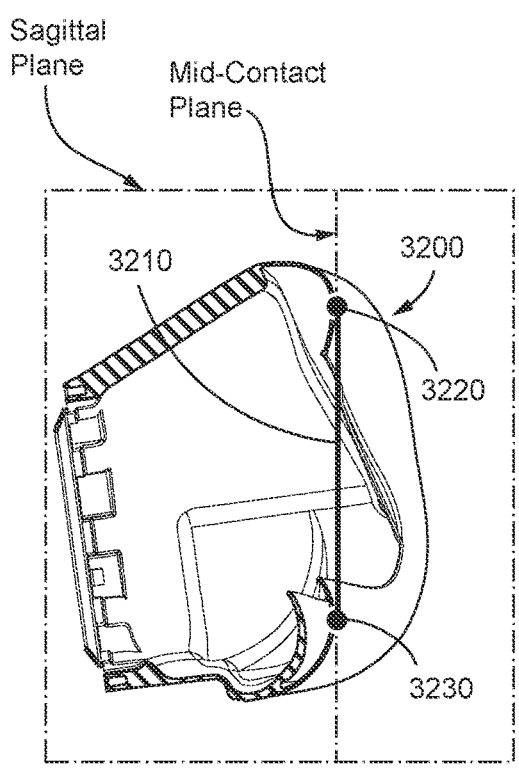

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
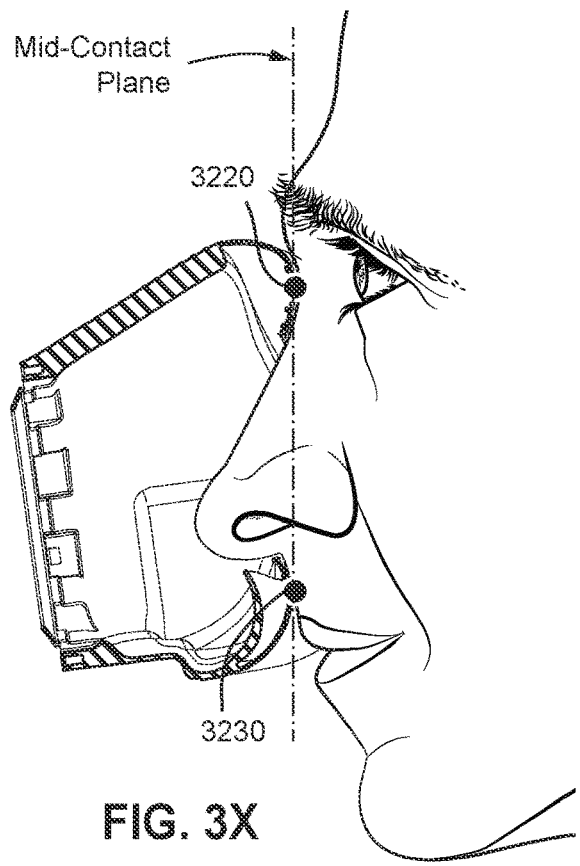

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

7.4 Rpt Device

Figure 4A:
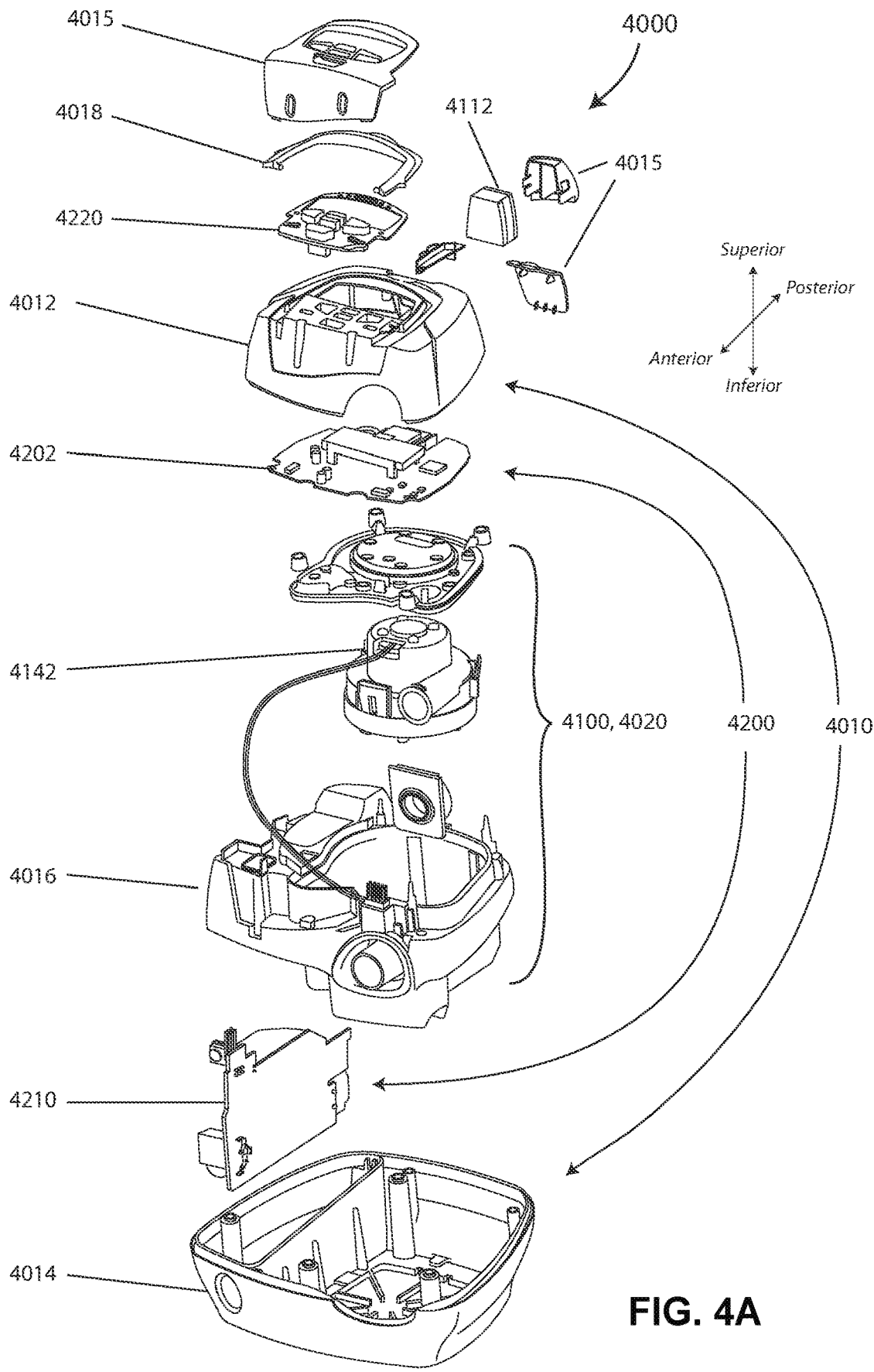

FIG. 4A shows an RPT device in accordance with one form of the present technology.

Figure 4B:
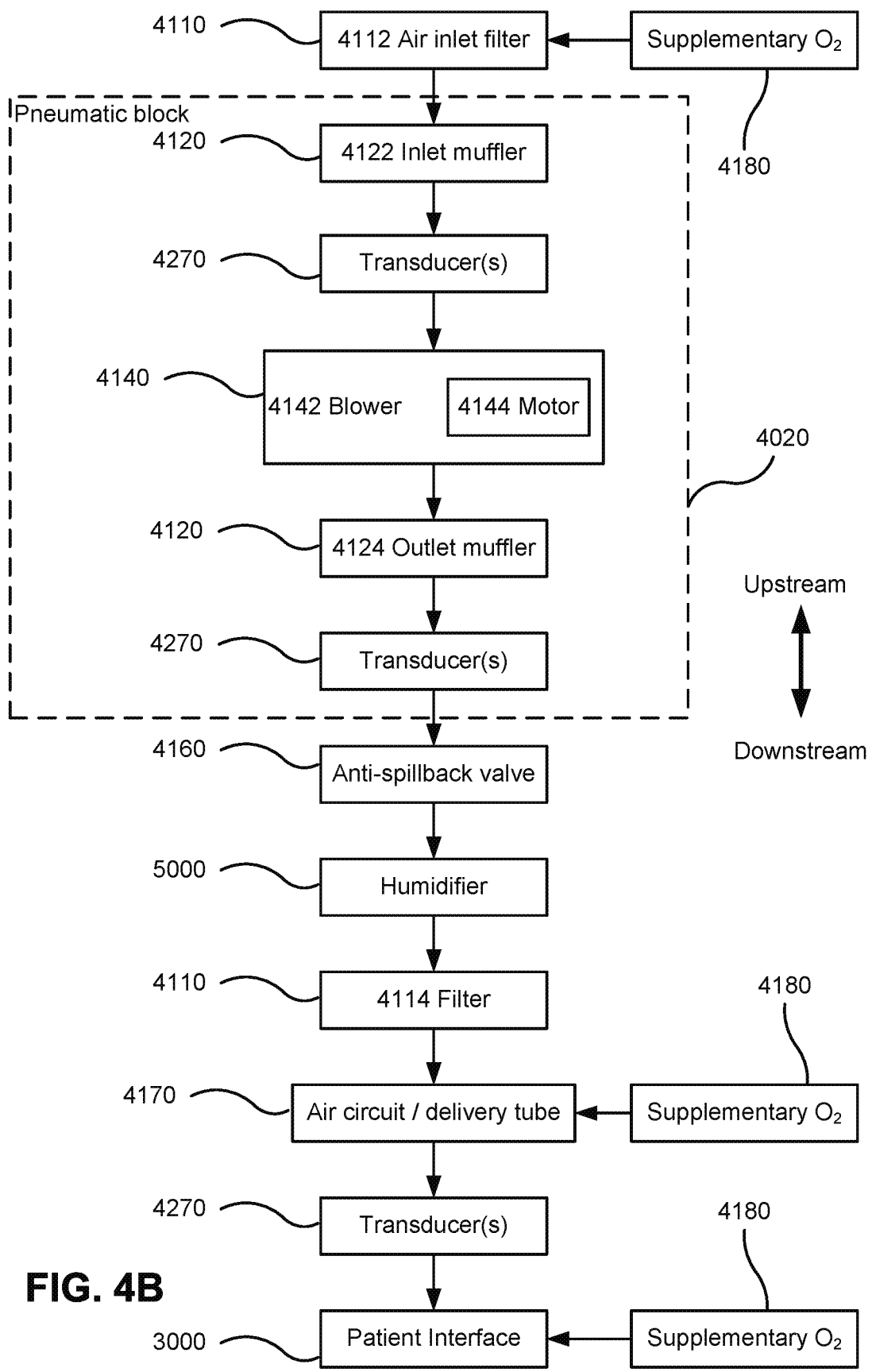

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
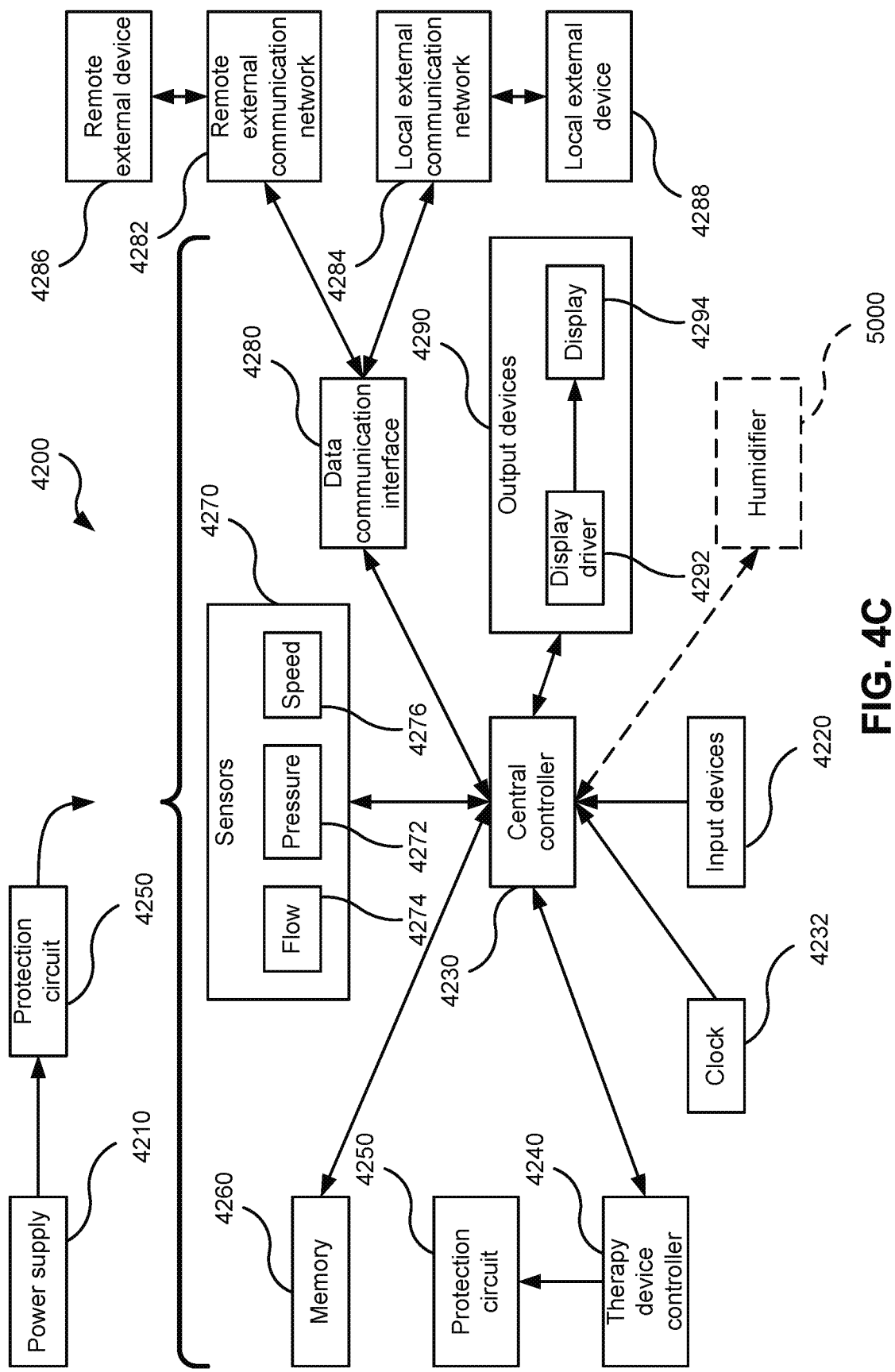

FIG. 4C is a schematic diagram of the electrical components of an RPT device in accordance with one form of the present technology.

7.5 Humidifier

Figure 5A:
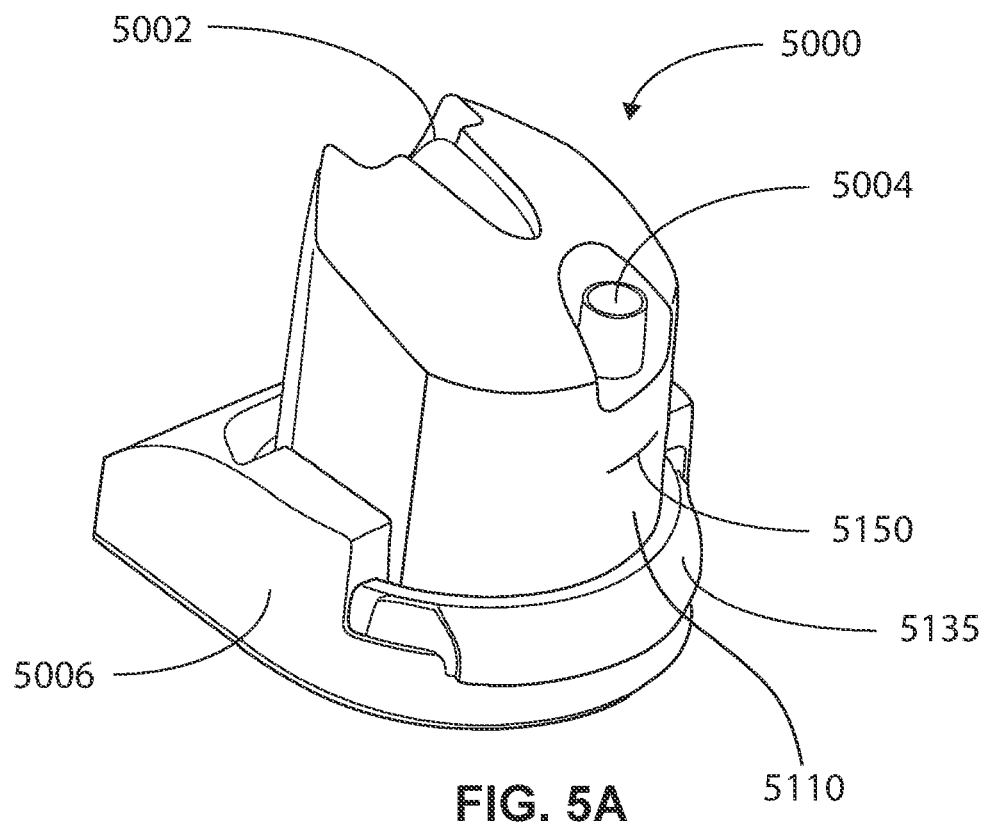

FIG. 5A shows an isometric view of a humidifier in accordance with one form of the present technology.

Figure 5B:
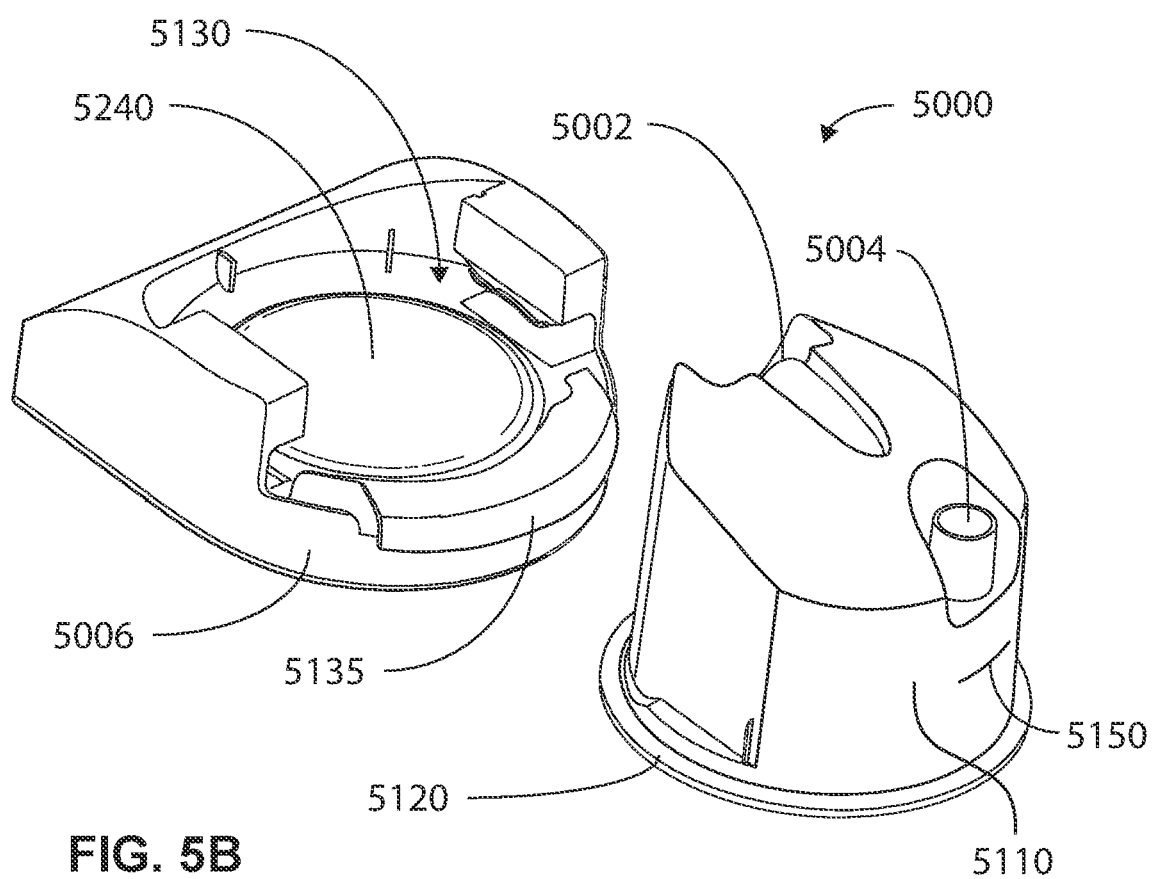

FIG. 5B shows an isometric view of a humidifier in accordance with one form of the present technology, showing a humidifier reservoir 5110 removed from the humidifier reservoir dock 5130.

Figure 6:
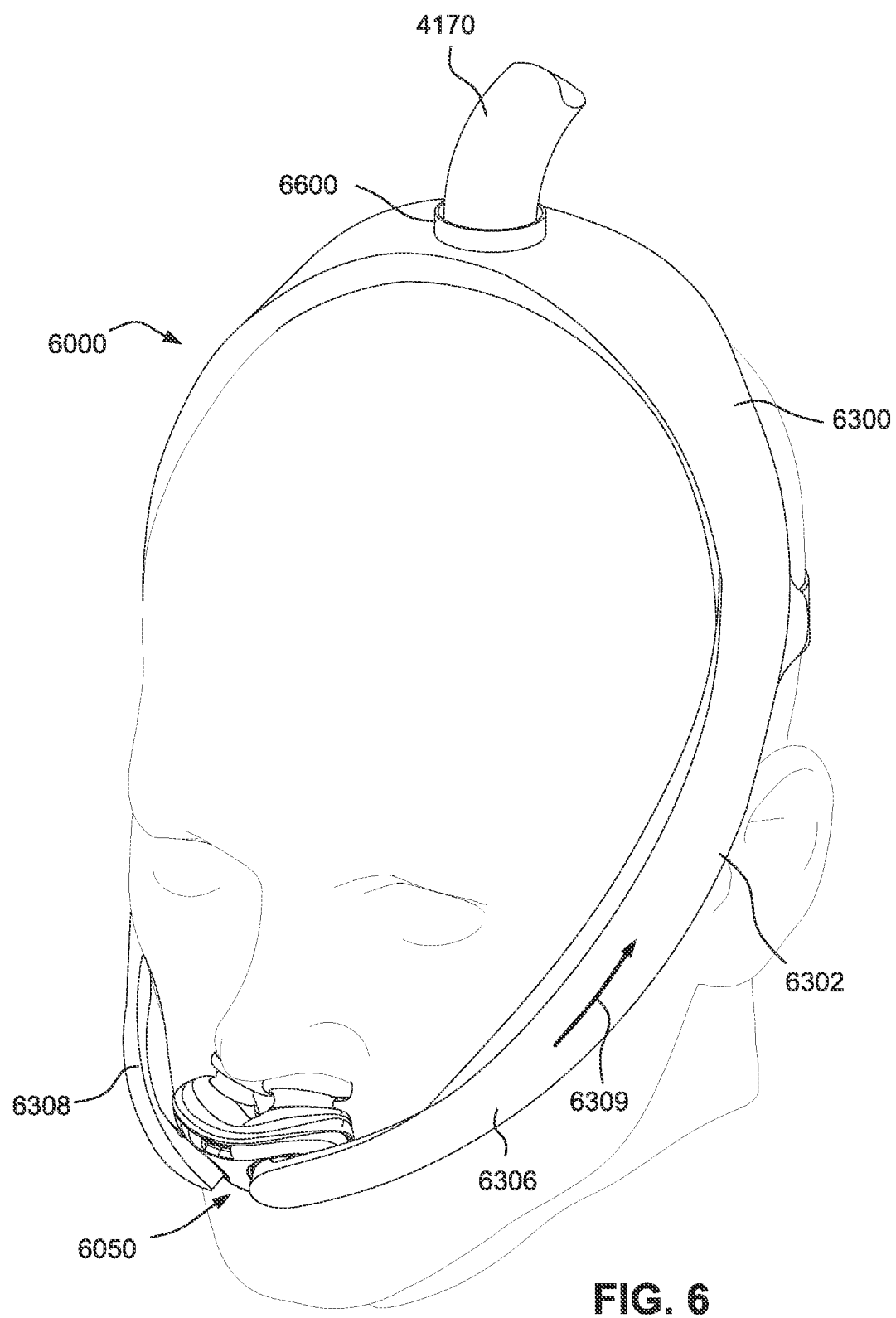

FIG. 6 is an alternate form of the present technology positioned on a patient's head.

Figure 7:
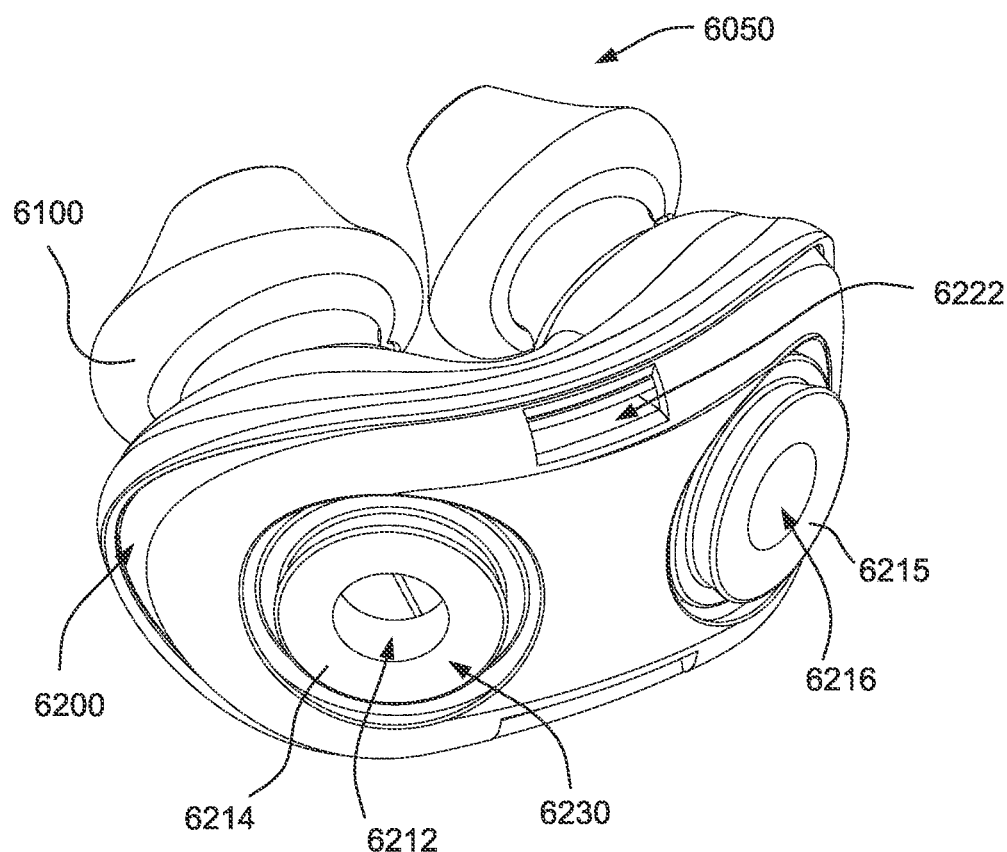

FIG. 7 is an isometric view of a mask assembly of the present technology.

Figure 8:
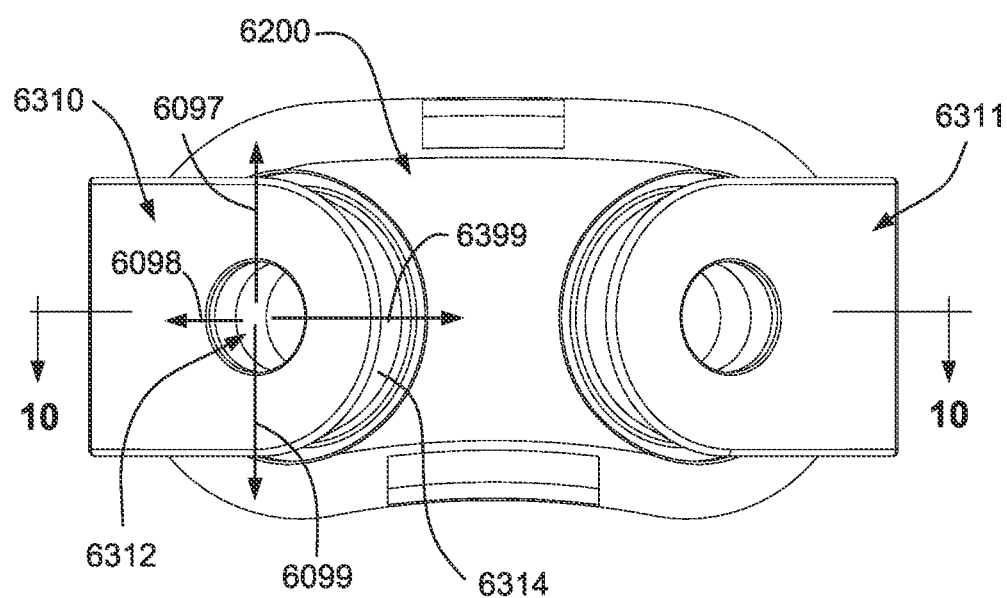

FIG. 8 is a view of a shell assembly along with conduit connector assemblies.

Figure 9:
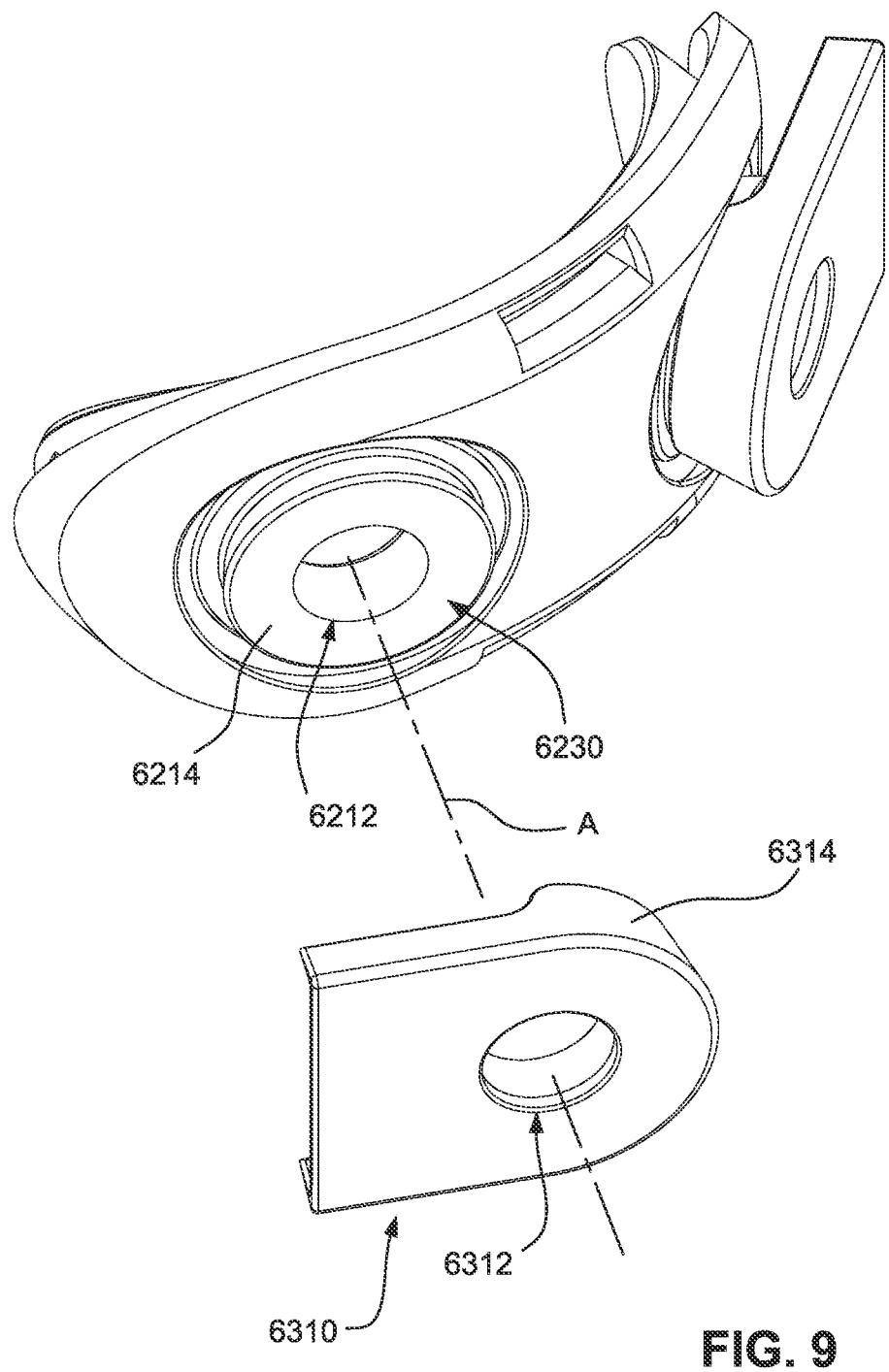

FIG. 9 is an isometric view of a conduit connector assembly spaced from the shell assembly.

Figure 10:
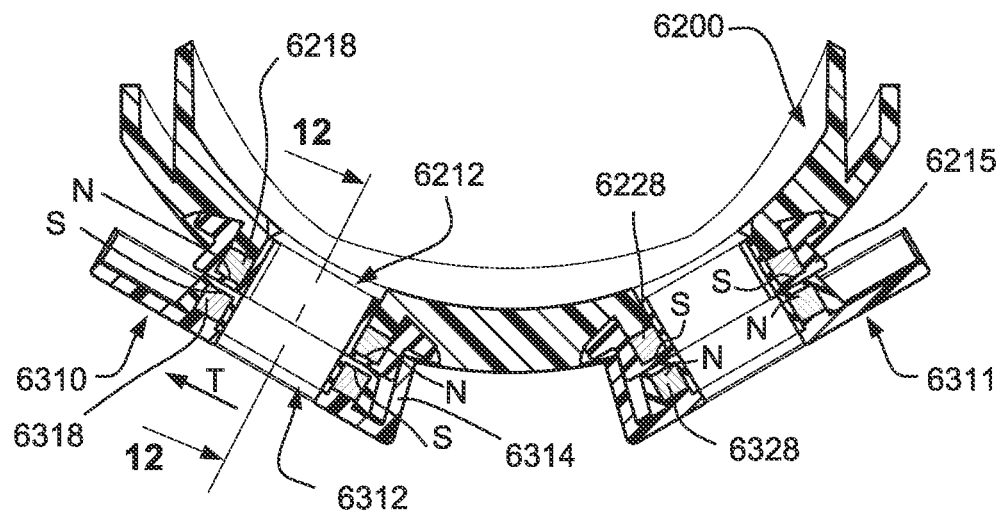

FIG. 10 is a cross-sectional view of the conduit connector assemblies and the shell assembly.

Figure 11:
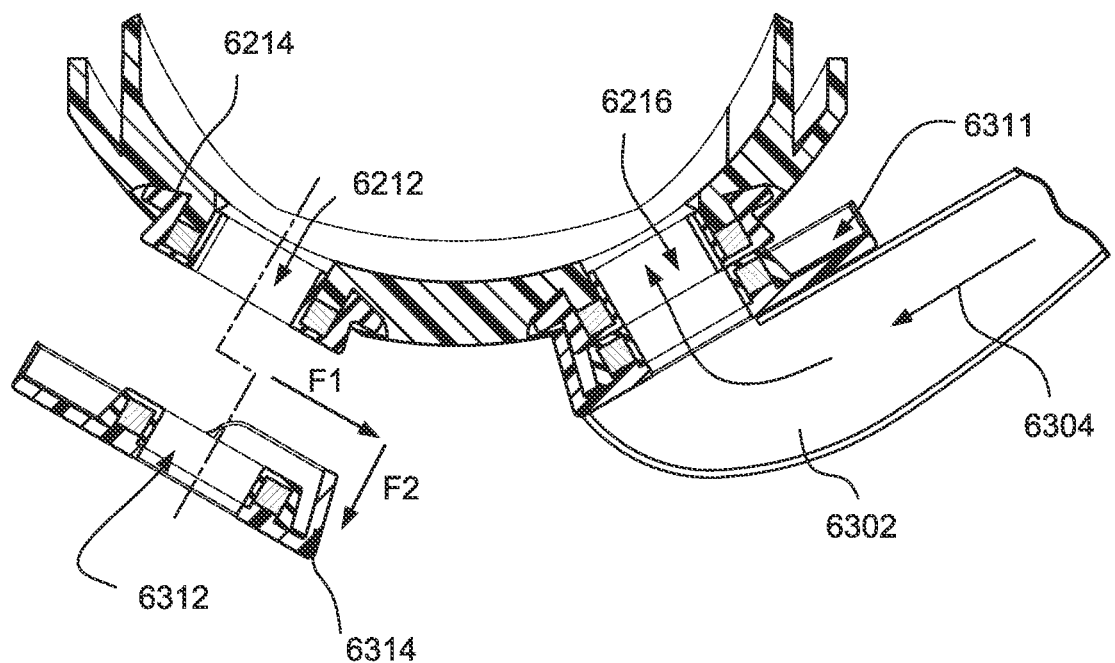

FIG. 11 is a cross-sectional view of the conduit connector assemblies and the shell assembly.

Figure 12:
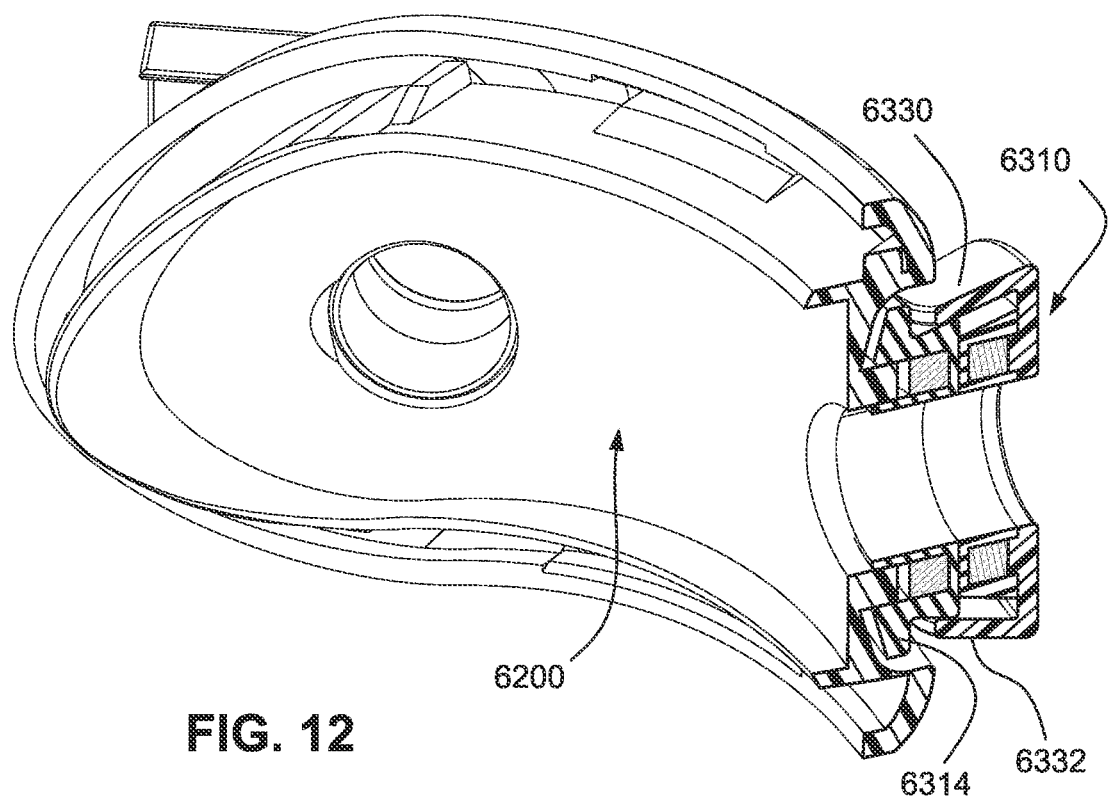

FIG. 12 is an isomeric cross-section view of the conduit connector assemblies and the shell assembly.

Figure 13:
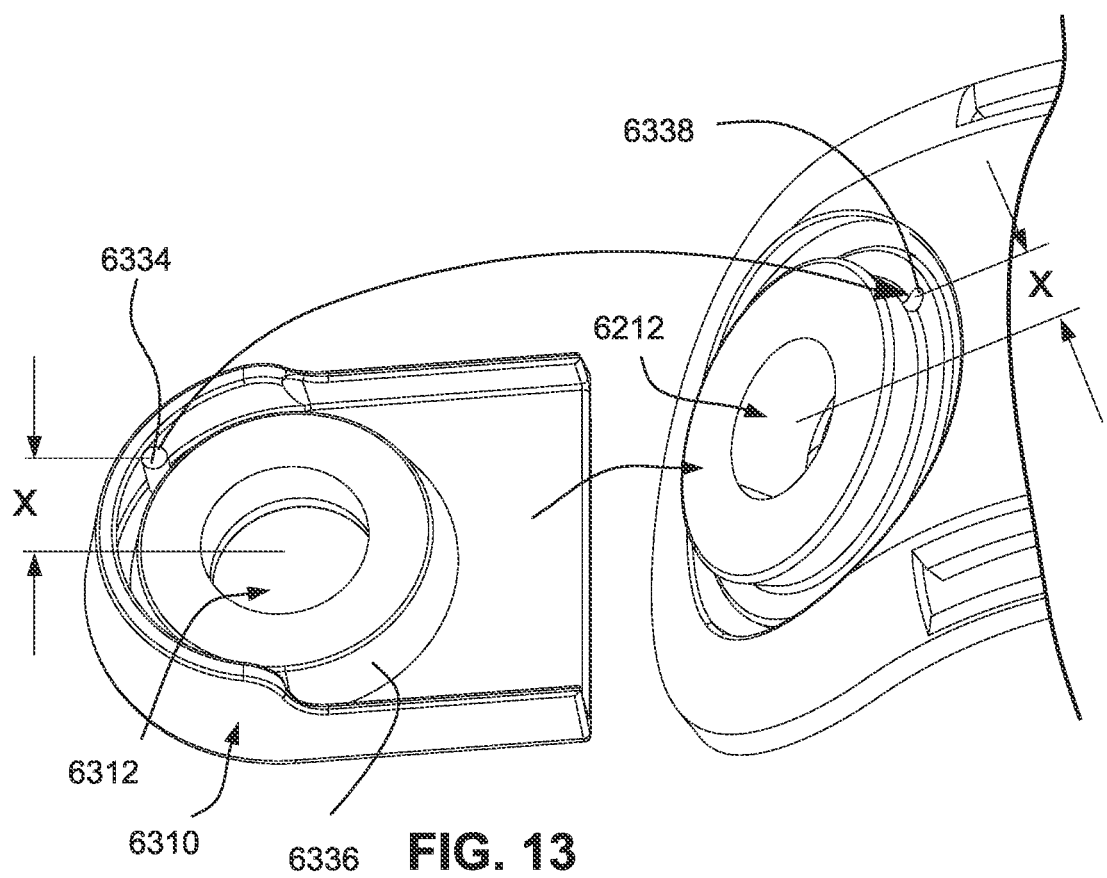

FIG. 13 is an alternate form of the present technology including an alignment and receptor feature.

Figure 14:
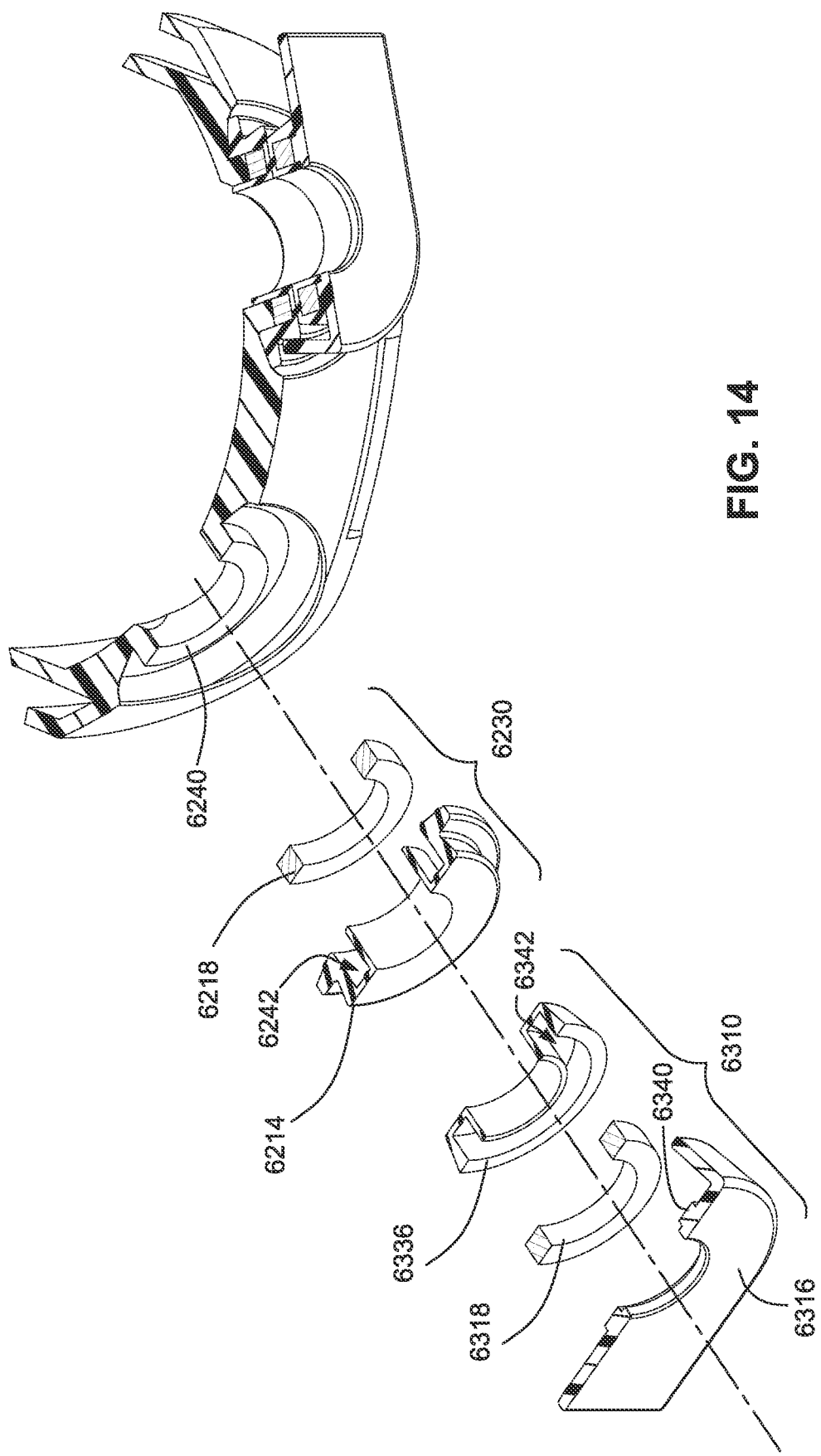

FIG. 14 is an isometric exploded view of the shell assembly and conduit connector assembly.

Figure 15:
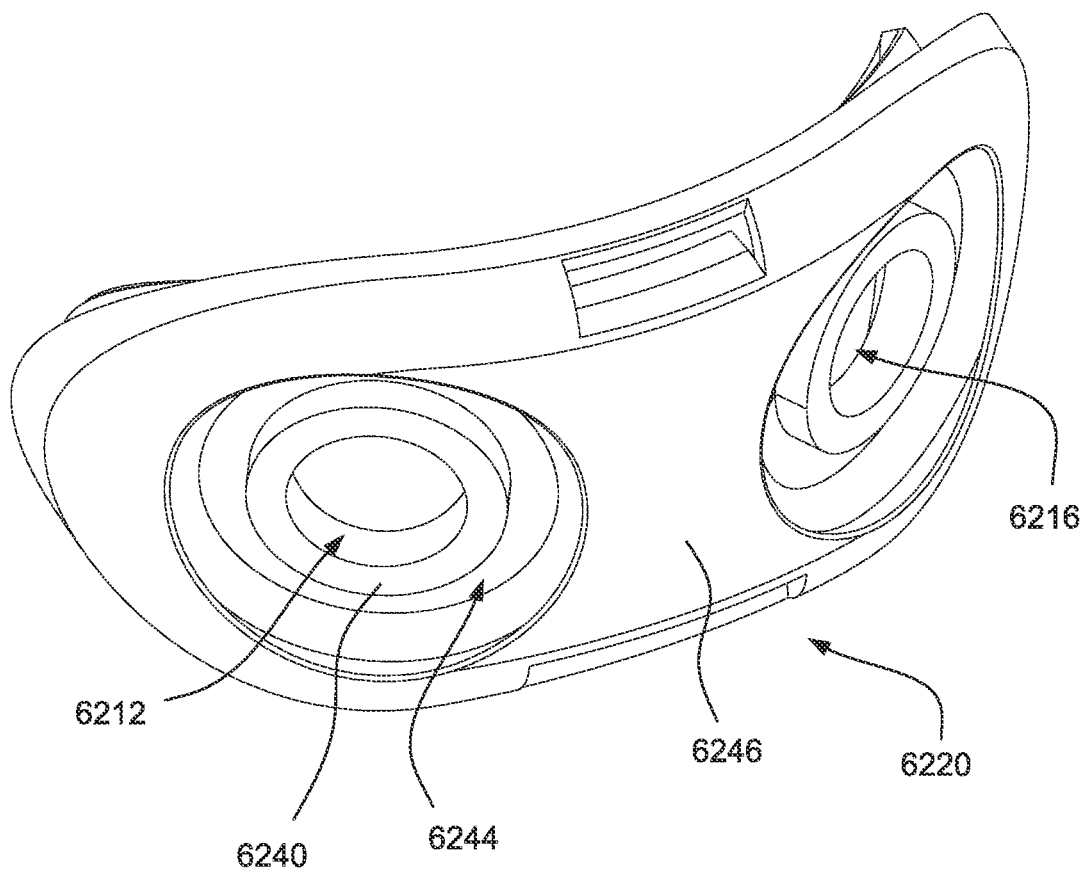

FIG. 15 is an isometric view of the shell.

Figure 16:
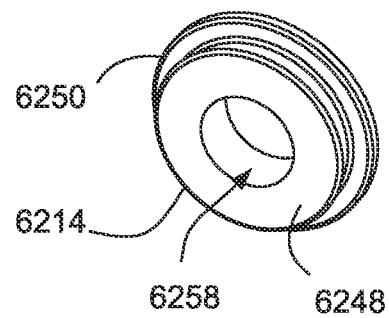

FIG. 16 is an isometric view of the shell magnet carrier.

Figure 17:
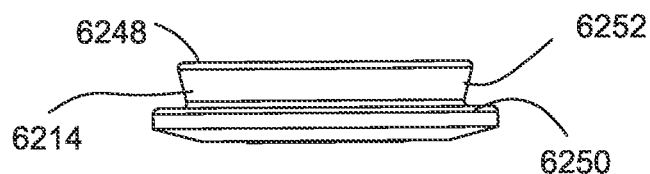

FIG. 17 is a side view of the shell magnet carrier.

Figure 18:
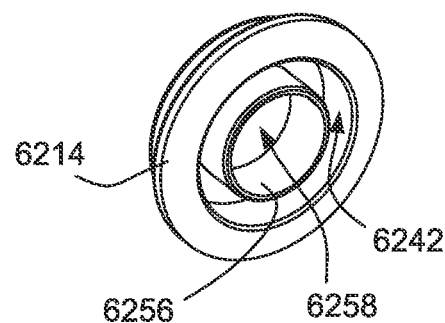

FIG. 18 is an isometric view of the shell magnet carrier.

Figure 19:
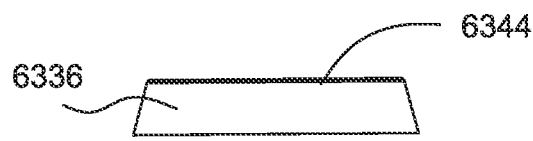

FIG. 19 is a side view of the conduit magnet carrier.

Figure 20:
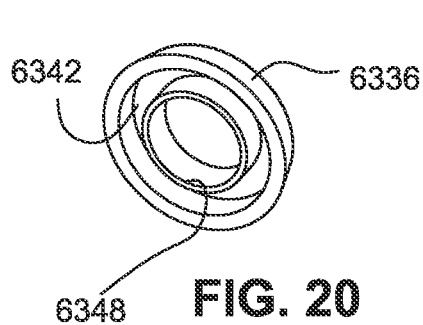

FIG. 20 is an isometric view of the conduit magnet carrier.

Figure 21:
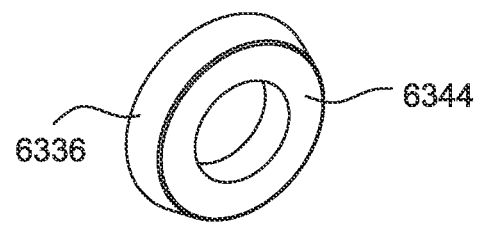

FIG. 21 is an isometric view of the conduit magnet carrier.

Figure 22:
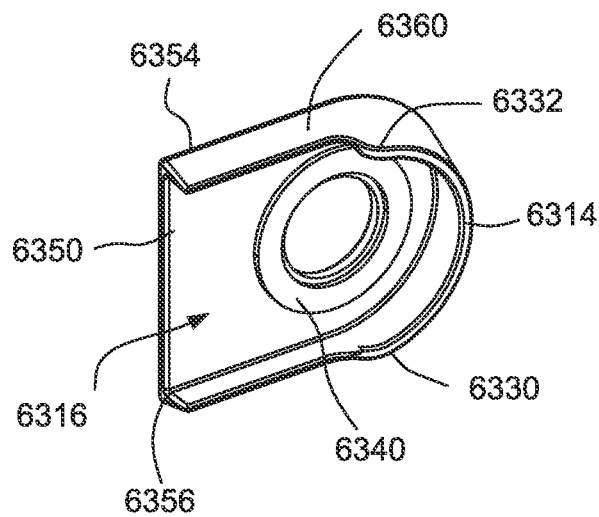

FIG. 22 is an isometric view of the connector.

Figure 23:
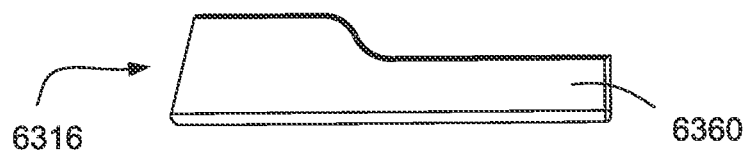

FIG. 23 is a side view of the connector.

Figure 24:
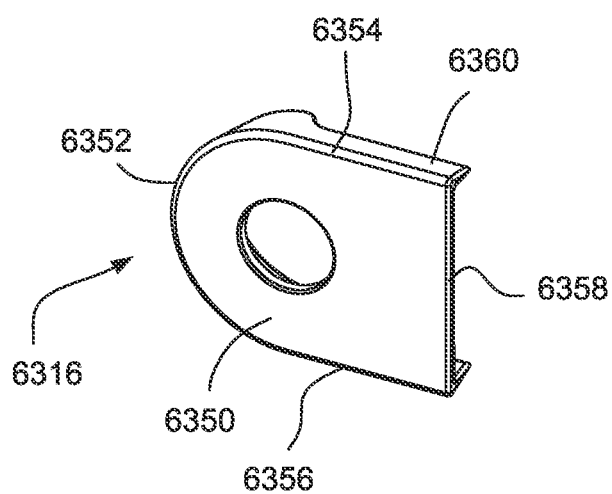

FIG. 24 is an isometric view of the connector.

Figure 25:
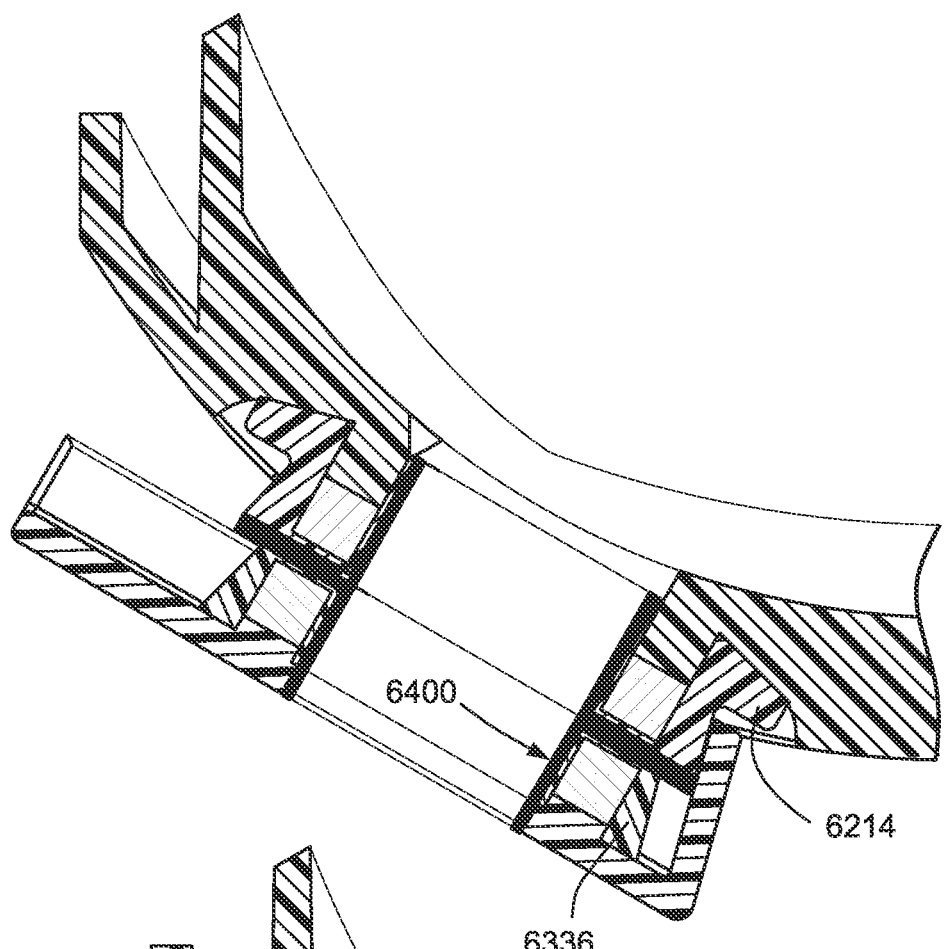

FIG. 25 is a cross-sectional view of a form of the present technology including add-on seals.

Figure 26:
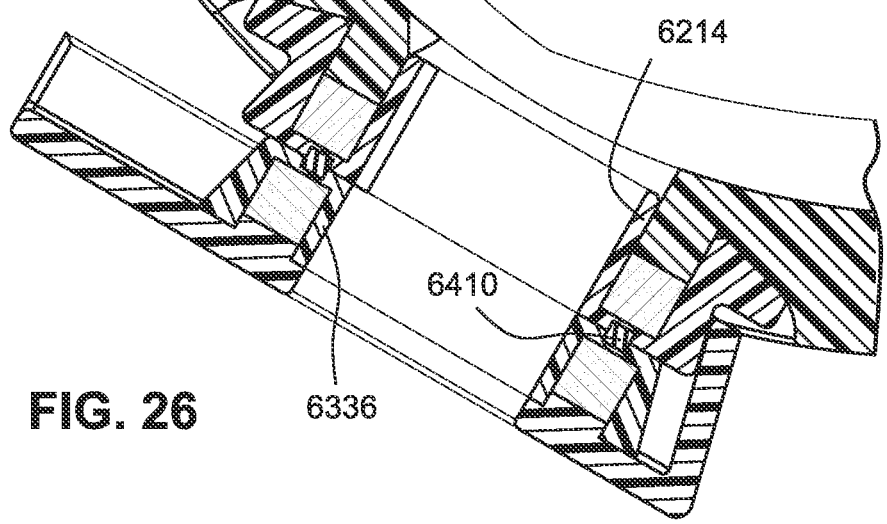

FIG. 26 is a cross-sectional view of a form of the present technology including overmold seals.

Figure 27:
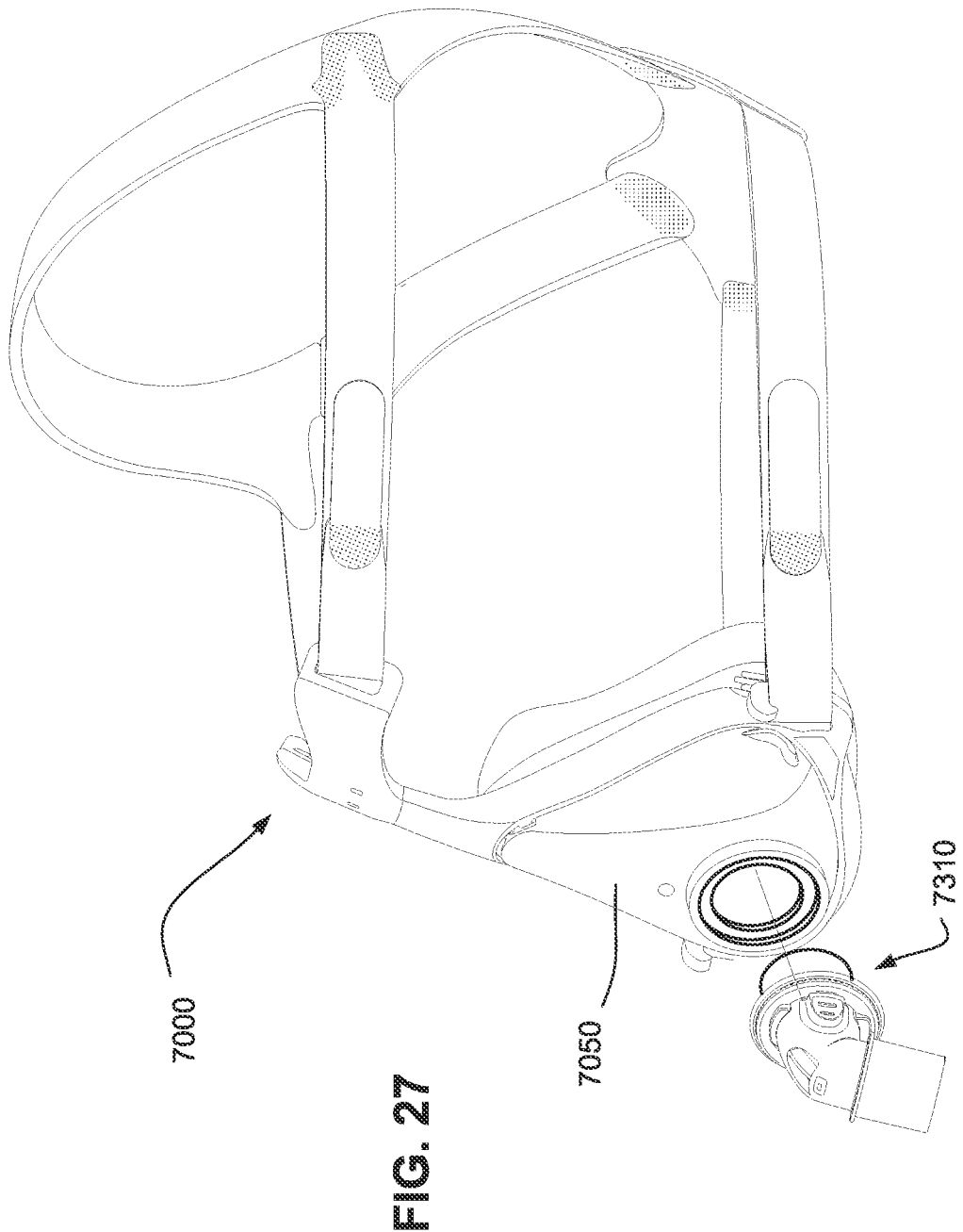

FIG. 27 is an isometric view of an alternate form of the present technology.

Figure 28:
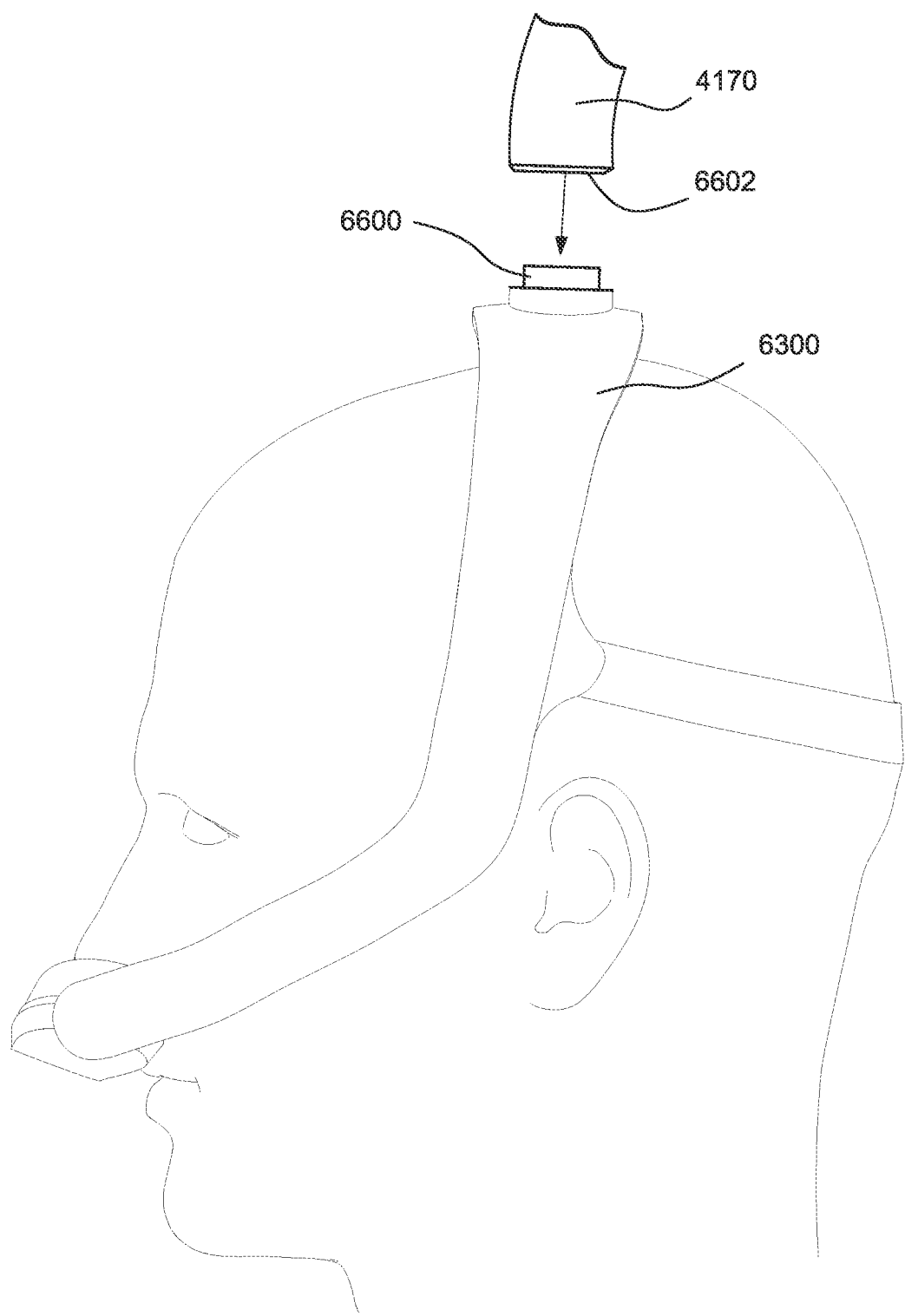

FIG. 28 is a side view of an alternative form of the present technology.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

8.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

8.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

8.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

8.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

8.3.2 Connection Between Air Delivery Conduit and Mask Assembly

In certain forms of the present technology a mask assembly and the air delivery conduit are removably attachable to each other. The mask assembly may include the seal forming structure. In some forms, the seal-forming structure is removable from the rest of the mask assembly in a non-destructive way. The mask assembly and the air delivery conduit may interact to form a passageway through which air is delivered to the patient. In some forms, the arrangement may also include a vent to allow the washout of exhaled carbon dioxide.

When wearing a patient interface a seal is formed between the seal forming structure and a region of the patient's face surrounding an entrance to the patient's airways. When air is pressurized through the patient interface, the seal forming structure tends to push away from the patients face and thus an opposite force is applied to the seal forming structure to assist in maintaining its position with respect the patient's face, surround the entrance to the patient's airways. In addition to providing sufficient and appropriate force to the sealing forming structure, patients may also desire a patient interface that is easily removable. Further, a patient interface that integrates a structure configured to stabilise and maintain sufficient force with an air delivery conduit may reduce the complexity of securing the patient interface to a patient such patient compliance with therapy is increased. A patient interface with such an arrangement is discussed below.

In FIG. 6 a patient interface is depicted. Patient interface 6000 includes a positioning and stabilizing structure that includes headgear 6300 and a mask assembly 6050, also referred to as a cushion assembly. Mask assembly 6050 may include various components including seal forming structure 6100 (sometimes referred to as a cushion), shell assembly 6200 and other components such as attachment components or ventilation components (see FIG. 3A). A chamber may be formed when combining seal forming structure 6100 with shell 6220. Therefore, each of shell 6220 and seal forming structure 6100 may form a portion of the plenum chamber. This plenum chamber is configured to be pressurisable to a therapeutic pressure of at least 6 cmH$_2$O above ambient air pressure. In other forms, the plenum chamber and seal forming structure 6100 may be a unitary member. In other forms the plenum chamber and seal forming structure 6100 may be formed of the same material. In still further forms, mask assembly 6050 may not include a separate shell 6220, rather components may be secured to the plenum chamber. For example, in some forms the plenum chamber may comprise shell 6220 or shell assembly 6200. Further, in this detailed description a separate shell and shell assembly are described, however, in other forms the plenum chamber may not include a separate distinguishable shell assembly. The components that are described as being attached to the shell may be co-formed with the plenum chamber or may also be attached to the plenum chamber. Further, the plenum chamber may include a seal forming structure or may be co-formed with the seal forming structure.

Headgear 6300 may be positioned to pass over a crown of a patient's head along the parietal bones from a left side to a right side of the patient's head. Headgear 6300 may include a headgear conduit 6302 that receives air that passes from RPT device 4000 through air circuit 4170 and through connection port 6600. Headgear 6300 includes a first conduit extension 6306 and second conduit extension 6308. These extensions extend toward and connect with mask assembly 6050 and terminate at respective ends. First conduit extension 6306 and second conduit extension 6308 may be configured to transfer a force from headgear 6300, for example force 6309, to maintain mask assembly 6050 in position. The force applied to mask assembly 6050 may be a force vector in the appropriate direction and magnitude to provide an adequate seal between seal forming structure 6100 and the patient's face. In this manner first conduit extension 6306 and second conduit extension 6308 may form ties that transfer tension forces to the mask assembly. First conduit extension 6306 and second conduit extension 6308 may be utilized draw seal-forming structure 6100 into sealing contact with a portion of the patient's face.

Additionally, first conduit extension 6306 and second conduit extension 6308 may be conduits such that each is configured to deliver air to the patient 1000. Therefore, first conduit extension 6306 and second conduit extension 6308 of headgear conduit 6302 may be configured to provide a supporting force to mask assembly 6050, deliver air to patient 1000, and draw seal-forming structure 6100 into sealing contact with a portion of the patient's face. In some forms, no additional portions of headgear 6300 are configured to interact with mask assembly 6050. That is, only first conduit extension 6306 and second conduit extension 6308 connect to mask assembly 6050.

Additionally, other portions of positioning and stabilising structure or headgear 6300 may also form a tie. For example, conduit connector assembly 6310 may be configured in use to be in tension and to direct a force to draw seal forming structure 6100 into contact with a portion of the patient's face. Other portions of headgear 6300 may also be in tension and form ties to assist in drawing seal forming structure 6100 into contact with a portion of the patient's face.

In other forms, headgear 6300 may comprise additional straps configured to position the patient interface 6000 about the patient's head to provide an adequate seal between seal forming structure 6100 and the patient while also permitting a comfortable fit of patient interface 6000. For example, a strap may be utilized that passes along the occipital bone of the patient and attaches to headgear conduit 6302. In still further forms, mask assembly 6050 may include retainer features that secure mask assembly 6050 to headgear 6300. For example, mask assembly 6050 may include hooks or openings through which additional straps of headgear 6300 may pass to secure headgear 6300 to mask assembly 6050.

Figure 1A:
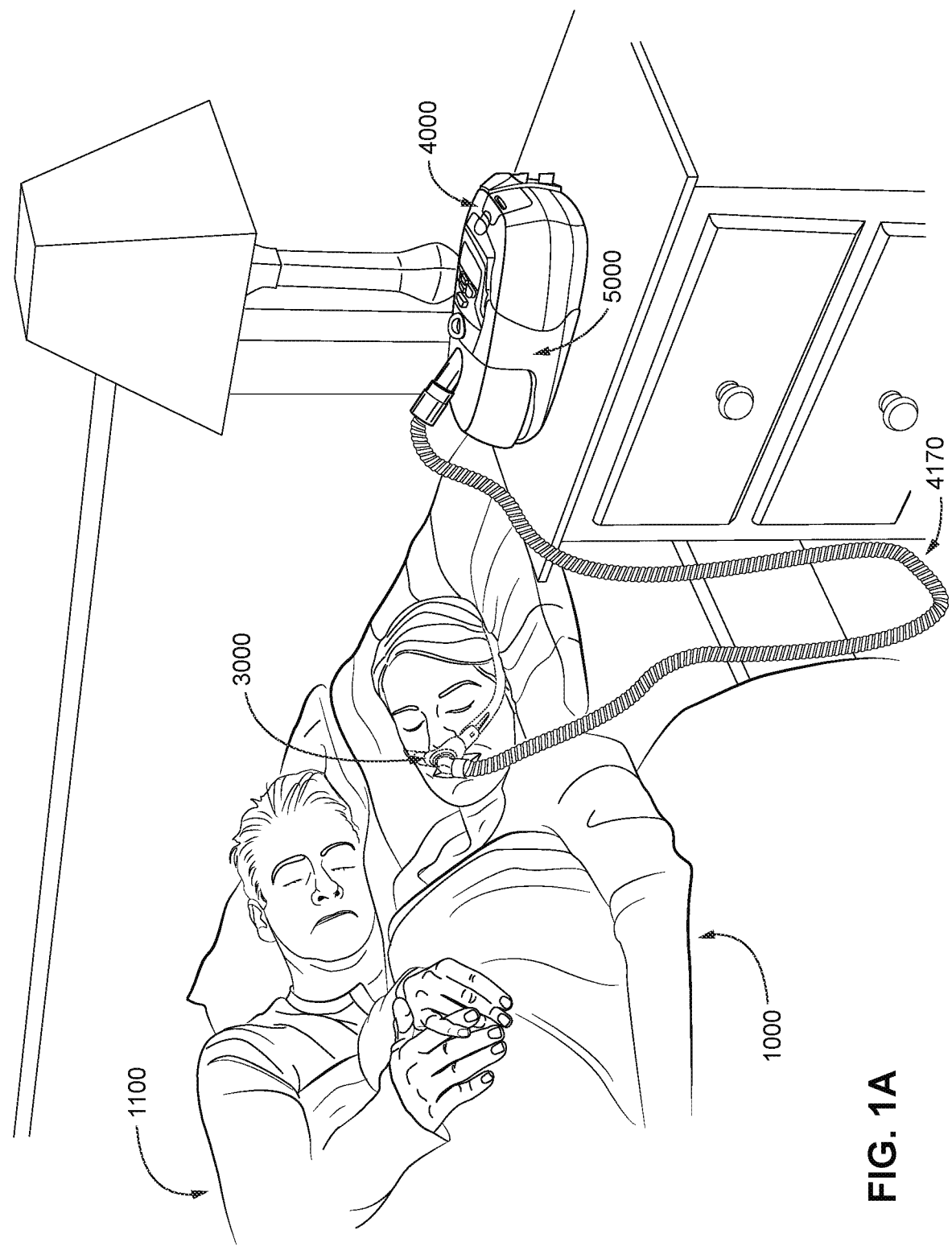
Figure 1B:
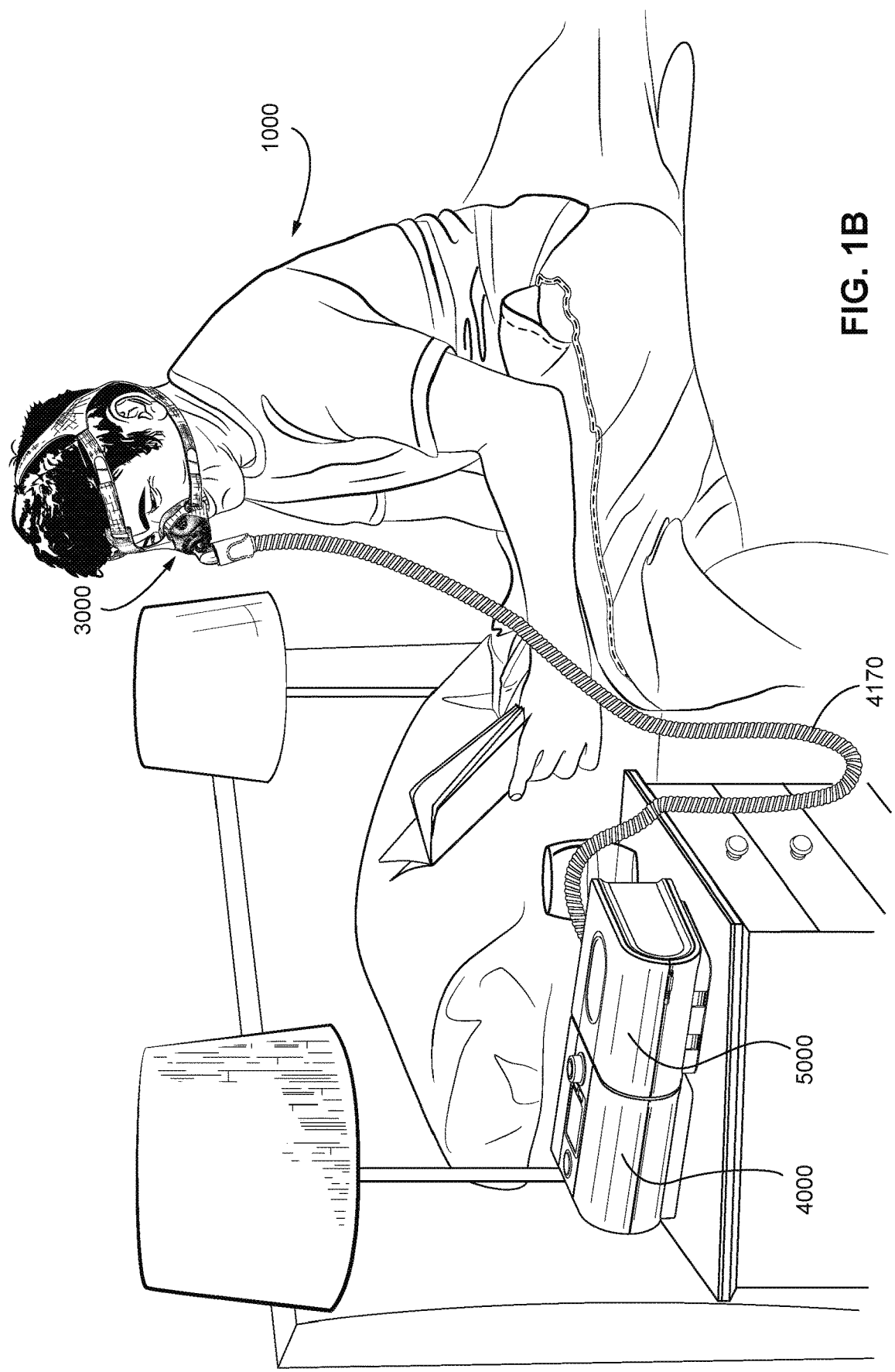
Figure 1C:

Although depicted as including a nasal pillow it should be recognized that in other forms of the present technology patient interface 6000 may include other mask assemblies or cushion assemblies such as the nasal mask depicted in FIG. 1B or the full face mask depicted in FIG. 1C.

Additionally, reference throughout the detailed description may refer to a single side (for example, left side or right side) of the mask assembly 6050 and headgear 6300, however, the same or similar descriptions are applicable to the other side of mask assembly 6050 and headgear 6300.

Referring to FIG. 7, mask assembly 6050 is shown in isolation from the rest of patient interface 6000. As shown, shell assembly 6200 interacts with and secures seal forming structure 6100. As previously discussed, in some forms mask assembly 6050 may not include a separate shell assembly but rather may include a plenum chamber. The shell assembly may form a portion of plenum chamber, or a shell may not be included in the plenum chamber. In some forms the plenum chamber may be integrally formed with the sealing forming structure. As depicted a tab from seal forming structure 6100 corresponds with a slot 6222 in shell assembly 6200 such that the tab is configured to maintain a friction fit with shell assembly 6200. Further, an annular extension from seal forming structure 6100 is configured to protrude into a corresponding circumferential channel or groove 6224 (See FIG. 5) of shell assembly 6200 such that seal forming structure 6100 is secured with shell assembly 6200. In some forms, seal forming structure 6100 may be permanently secured with shell assembly 6200 such as by adhesive or co-molding or co-forming. In other forms, seal forming structure 6100 may be friction or snap fit with shell assembly 6200 such that seal forming structure 6100 is non-destructively removable from shell assembly 6200. For example, seal forming structure 6100 may be removable such that the patient is able to clean seal forming structure 6100 or replace seal forming structure 6100 when required.

In some forms mask assembly 6050 is a separate component from the rest of patient interface 6000. That is, mask assembly 6050 may be non-destructively removable from the other components of patient interface 6000. Also, mask assembly 6050 may be secured to headgear 6300 only via a connection pathway as discussed later in this detailed description. That is, no additional straps may be required to secure mask assembly 6050 beyond the air conduit connection between mask assembly 6050 and headgear conduit 6302. In other forms, however, additional straps may be utilized to secure mask assembly 6050 in place during use.

As shown, shell assembly 6200 includes shell opening 6212, also referred to as a plenum inlet port, and second shell opening 6216. Shell opening 6212 is bounded by a shell magnet carrier 6214 and shell opening 6216 is similarly bounded by second shell magnet carrier 6215. In other forms, a plenum magnet carrier may be utilized and secured to the plenum chamber or co-formed with the plenum chamber. In some forms the plenum magnet carrier may also be utilized as a retention member. In still further forms, a separate retention member may be utilized that does not house a magnet. In still further forms, the retention member may be integrally formed with the plenum chamber. In other forms the retention member may be separately formed.

The shell magnet carriers may be substantially cylindrical in shape and the shape of the shell magnet carriers are shown in detail in FIGS. 16-18. These magnet carriers are utilized to secure magnets in place while also protecting the magnets from damage. For example, shell magnet carrier 6214 secures shell magnet 6218. Further, the magnet carriers also are utilized to assist in securing headgear 6300 to mask assembly 6050 by providing an engagement feature, retention member receptor, lip, edge, prong, pin, or anchor receptor to which portions of a conduit connector assembly 6310 may interact. The combination of shell magnet carrier 6214 and shell magnet 6218 is referred to as shell receptor assembly 6230 or in other forms a plenum chamber receptor. In other forms the inlet port may be magnetized without the use of a shell magnet carrier or other carrier. In still other forms, a receptor assembly may be spaced from the inlet port. In still further forms the inlet port and the receptor may be formed as a unitary piece or a single component.

In other forms, a separate component may be utilized to interact with the conduit connector assembly 6310. For example, a magnet may be enclosed in shell magnet carrier 6214 however a separate anchor receptor may be utilized to interact with a corresponding anchor of conduit connector assembly 6310. The anchor receptor may be spaced from the shell openings and/or the shell magnet carriers. In some forms, the anchor may also be utilized to restrict or reduce rotational movement of the conduit connector assembly 6310.

Referring to FIG. 8, shell assembly 6200 is depicted along with conduit connector assembly 6310 and another conduit connector assembly 6311. For ease of description, conduit connector assembly 6310 is described, however the structures recited with respect to conduit connector assembly 6310 may also apply to the other conduit connector assembly 6311. Conduit connector assembly 6310 is utilized to secure the ends of headgear 6300 to shell assembly 6200 such that the interiors of mask assembly 6050 and headgear conduit 6302 (see FIGS. 6 and 11) are in fluid communication with each other thereby forming a pneumatic connection. As shown, connector opening 6312 aligns with shell opening 6212. This connection permits air to flow through connector opening 6312 and shell opening 6212 to the patient such that the patient is able to receive therapy. Conduit connector assembly 6310 may assist in providing an air tight seal between mask assembly 6050 and headgear conduit 6302 to minimize the quantity of air leakage through the junction between the components. As shown in FIG. 8 as well as FIGS. 9-14, conduit connector assembly 6310 is depicted without the rest of headgear 6300 for ease of viewing. Further, shell assembly 6200 is depicted without seal forming structure 6100 for ease of viewing and description. It should be recognized that in use conduit connector assembly 6310 is secured to headgear 6300 and/or headgear conduit 6302 and seal forming structure 6100 is secured to shell assembly 6200.

As shown in FIGS. 8-11, conduit connector assembly 6310 includes a connector opening 6312. This connector opening 6312 corresponds with a shell opening 6212. The openings are aligned with each other and form a channel through which air is directed from headgear conduit 6302 to mask assembly 6050 (see for example FIG. 10 and FIG. 11). As shown for example in FIG. 10, the shell assembly 6200 includes two openings (shell opening 6212 and second shell opening 6216) on opposite sides of shell assembly 6200. Each of these openings may be utilized to direct air toward a naris of the patient.

Referring particularly to FIGS. 10 and 11, shell assembly 6200 and conduit connector assembly 6310 are depicted in cross-section. In FIG. 10, conduit connector assembly 6310 is removably secured to shell assembly 6200. A magnetic attraction between the conduit connector assembly 6310 and the shell assembly 6200 allows the connectors to easily self-locate towards one another for magnetic engagement. This self-location or self-alignment may assist in locating other portions of headgear 6300 in a position to assist in maintaining seal forming structure 6100 contact with the patient's face. In addition to self-locating, the magnetic attraction also allows the conduit connector assembly 6310 to self-connect to the shell assembly 6200 or self-align with the shell assembly 6200.

In addition, rather than requiring a friction fit, pressure fit, snap fit or connection fit, conduit connector assembly 6310 may be removed from shell assembly 6200 simply by pulling conduit connector assembly 6310 in a particular direction away from shell assembly 6200. No pinching of tabs or twisting to disengage is required. This easily removable and attachable feature may be attractive to patients that have difficulty removing and donning a patient interface.

Further, by utilizing a magnetic field, the components may be able to rotate with respect to one another. As shown in FIG. 9, conduit connector assembly 6310 may be permitted to freely rotate about the axis A that extends through the center of shell opening 6212 as well as connector opening 6312. Permitting conduit connector assembly 6310 to rotate may permit patient interface 6000 to be usable with a multitude of differently shaped heads and face of patients. Additionally, the ability to rotate the conduit connector assembly 6310 provides the ability to adjust the orientation of the extensions 6306 and 6308 with respect to the mask assembly 6050 such that the force vectors provided by said extensions 6306 and 6308 may be adjusted. The term freely rotate is used to relate to forms in which protrusions, snaps, or locks between shell assembly 6200 and conduit connector assembly 6310 do not restrain the rotation of conduit connector assembly 6310 about an axis. As shown in FIG. 8, when conduit connector assembly 6310 is positioned against or engaged with shell receptor assembly 6230 conduit connector assembly 6310 is still permitted to rotate about the axis A.

Although described with the use of magnets, in some forms of the present embodiment, magnets may not be utilized. In other forms, magnets may be used in on area while a ferrous material may be used in another to form a magnetic attraction such that each portion need not include a magnet to form a magnetic attraction. For example, in some forms conduit connector assembly 6310 may include a magnet while shell assembly 6200 include a ferrous material. In still further forms, conduit connector assembly 6310 includes a magnet with north polarity and shell receptor assembly 6230 includes a ferrous material. Conduit connector assembly 6311 may include a ferrous material while second shell magnet 6228 is north in polarity. Therefore the conduit connector assembly 6310 and conduit connector assembly 6311 may be restricted from connecting to the incorrect opening within the plenum chamber or shell assembly 6200.

Additionally, in some forms the magnetic force causes conduit connector assembly 6310 and the shell receptor assembly 6230 to be attracted to each other such that a seal is formed between conduit connector assembly 6310 and shell receptor assembly 6230. This may form a pneumatic seal between the mask assembly 6050 and the headgear conduit 6302. This may be a separate function from the self-locating feature. For example, conduit connector assembly 6310 and shell receptor assembly 6230 may be particularly oriented by the user or a clip or other mechanism and the magnetic form may be utilized to provide the seal between the components.

In other forms, the magnetic force may self-align the conduit connector assembly 6310 to the shell assembly 6200, thereby positioning the conduit connector assembly 6310 and shell assembly 6200 in a particular orientation to assist in donning patient interface 6000.

In some forms a separate action or structure may provide a seal between the conduit connector assembly and the shell assembly 6200. For example, a separate snap, clip, slide, pressure fit connection, or other suitable connection may be formed separately from the magnetic force. In such a configuration the magnetic force may still be utilized to located the various components of patient interface 6000 in a suitable position to permit adequate use of patient interface 6000.

When worn by a patient, mask assembly 6050 may be disposed to fall away from the face. That is, in the anterior and/or inferior direction (see e.g., FIG. 2D). Headgear 6300 meanwhile may be configured to support mask assembly 6050 by providing an opposite posterior and/or superior force to mask assembly 6050. The configuration of conduit connector assembly 6310, conduit connector assembly 6311, and mask assembly 6050 utilizes these forces so that each of the mask assembly 6050, conduit connector assembly 6310, and conduit connector assembly 6311 position and stabilise mask assembly 6050 in place. As shown at least in FIGS. 9 and 11, connector 6316 of conduit connector assembly 6310 includes a front lip 6314. This front lip 6314 extends around and abuts against the shell magnet carrier 6214 such that the front lip 6314 is anchored to shell magnet carrier 6214. In some forms, front lip 6314 or a portion of conduit connector assembly 6310 that restrictively engages with a portion of shell assembly 6200 may be referred to as an anchor or anchor member. This anchor member may be structured and positioned to at least partially counteract tension forces tending to separate the shell assembly 6200 from the conduit connector assembly 6310. The outer surface of the shell magnet carrier 6214 has a tapered surface and the front lip 6314 of the connector 6316 has an oppositely angled interior surface such that the interior surface of front lip 6314 lies flush against the outer surface of shell magnet carrier 6214. The interior surface of front lip 6314 may be substantially linear along the height of front lip 6314. The tapered configuration of shell magnet carrier 6214 permits front lip 6314 to "hook" or grab against shell magnet carrier 6214 when the front lip 6314 is placed in tension against shell magnet carrier 6214 while also permitting rotation about Axis A. This tension assists in pressing the seal forming structure 6100 to the face of the patient to form a seal. Because connector 6316 is in tension T (see FIG. 10) generally toward the face of the patient (or posterior direction), and mask assembly 6050 is disposed to fall away from the face (or anterior direction) the front lip 6314 and shell magnet carrier 6214 work to maintain mask assembly 6050 in a stable location. As previously described, an anchor receptor may be utilized that is spaced from shell magnet carrier 6214. In such configurations the front lip 6314 or anchor of conduit connector assembly 6310 may interact with the anchor receptor.

In other forms, the shell magnet carrier 6214 or other retention member receptor may have variously shaped outer walls. For example, in some forms the retention member receptor may have a flat outer wall that does not taper but rather stays consistent along the height of the retention member receptor such that the retention member receptor is cylindrical rather than conical. In other forms, the retention member receptor may have a rounded outer surface or may include a concave inward or concave outward surface. In some forms a retention member may have an oppositely shaped surface, or surface with the opposite curvature from the retention member receptor such that the surfaces of the retention member receptor and the retention member lie flush against one another when positioned adjacent to each other during use.

Various shapes and spatial locations of an anchor and anchor receptor are possible. For example, an anchor or anchor receptor may have a male or female configuration. Additionally, the anchor need not be at an end of conduit connector assembly 6310. For example, conduit connector assembly 6310 may have a separate opening spaced from connector opening 6312 that is configured to receive a corresponding anchor receptor located on shell assembly 6200. In such a manner the anchor and anchor receptors may be spaced from the pneumatic seals as well as the magnets of patient interface 6000.

Because connector 6316 is in tension toward the face of the patient during use of patient interface 6000, there is no need to secure connector 6316 to maintain force away from the face of the patient. For example, because mask assembly 6050 is generally not able to move toward the face of the patient, there is no reason for conduit connector assembly 6310 to restrict such a motion. Therefore, the front lip 6314 does not extend all around the perimeter of connector 6316. Further, this design permits connector 6316 to move away from the face (or the anterior direction). By moving the connector 6316 in the anterior direction, the front lip is moved away from the shell magnet carrier 6214 and the conduit connector assembly 6310 is able to be removed from mask assembly 6050. In this manner, the conduit connection may act as both a support for mask assembly 6050 as well as an easily removable air passage conduit.

In other forms, a front lip may not be utilized. For example, conduit connector assembly 6310 may include an annular extension that extends into shell opening 6212. The extension may abut against the interior surfaces that bound shell opening 6212 such that conduit connector assembly 6310 is restrained from lateral translation, but would permit movement of the conduit connector assembly 6310 into and out of the shell opening 6212.

As shown in FIG. 8, front lip 6314 (see FIGS. 10 and 22) along with upper and lower lips 6330, 6332 (see FIGS. 12 and 22), assist in restraining conduit connector assembly 6310 from moving outward from the sagittal plane along directions 6097, 6098, and 6099. In contrast, the lips do not resist movement in laterally inward toward the sagittal plane along direction 6399. This permits removal of conduit connector assembly 6310 by moving conduit connector assembly in direction 6399. As depicted in FIG. 8, conduit connector assembly 6310 is restricted from moving laterally in the plane that includes direction 6097, 6098, and 6099. However, conduit connector assembly 6310 is able to move in direction 6399 which is in the same plane direction 6098, but in an opposite direction. Therefore conduit connector assembly 6310 is restricted from moving in various directions of a single plane, however conduit connector assembly 6310 may move in a particular direction within the plane. As depicted, conduit connector assembly 6310 is able to be moved in a direction opposite of the direction of force applied upon connector assembly 6310 by headgear 6300.

Based on the design of conduit connector assembly 6310 and in particular the interaction between connector 6316 and shell magnet carrier 6214, removal of conduit connector assembly 6310 from shell assembly 6200 may be more particular than just an anterior movement by conduit connector assembly 6310. Due to the angled nature of both shell magnet carrier 6214 and front lip 6314, conduit connector assembly 6310 is moved away from shell magnet carrier 6214 in a lateral direction toward the sagittal plane or the center of shell assembly 6200. This forms a space between shell magnet carrier 6214 and front lip 6314 such that the conduit connector assembly 6310 is permitted to move in the anterior direction away from mask assembly 6050. For example, a possible removal motion is depicted in FIG. 11. As shown, conduit connector assembly may first be moved laterally toward the centre of shell assembly 6200 along the direction of F1. After movement in the direction of $F_1$ conduit connector assembly 6310 may then be moved along the direction of F2, allowing conduit connector assembly 6310 to be moved away from mask assembly 6050. It should be recognized that a combination of forces may be utilized. For example, rather than pulling conduit connector assembly 6310 along direction F2, mask assembly 6050 may be pressed in an opposite direction toward the face of the patient, thus causing sufficient space to permit conduit connector assembly 6310 to be removed from mask assembly 6050. Further, in some forms, sufficient force along direction $F_2$ may press front lip 6314 against the outer surface of shell magnet carrier 6214, moving conduit connector assembly 6310 in a direction parallel to direction F1 such that conduit connector assembly 6310 is removable from shell magnet carrier 6214.

In some forms, the magnets of the shell assembly 6200 and the magnets in the conduit connector assembly 6310 may be particularly arranged to prevent, resist, or reduce the chance of attaching the conduit connector assembly 6310 to the incorrect shell opening 6212.

As depicted through the figures, shell assembly 6200 includes shell opening 6212 and second shell opening 6216. Each of the openings in shell assembly 6200 may be associated with an air passage for directing air toward an individual naris of the patient. In some forms, mask assembly 6050 may be formed so as to fit on the face of the patient in a particular orientation. For example, mask assembly 6050 may not be completely symmetrical along all axes. Therefore, there may be a "wrong" way and a "right" way to wear the patient interface 6000. For example, there may be a "left" shell opening and a "right" shell opening as well as a "left" conduit connector assembly and a "right" conduit connector assembly. To reduce the chance of a patient accidentally assembling the patient interface incorrectly (for example, attaching the "left" conduit connector to the "right" shell opening), the magnets within each of the conduit connector assembly and the shell assembly may have particular polarities. As shown in FIG. 10, for example, shell magnet 6218 has an outer portion (facing away from shell 6220) with a first polarity (for example, associated with the magnetic North) and an inner portion with an opposite second polarity (for example, associated with magnetic South). Conduit magnet 6318 has an outer portion (facing away from connector 6316) that has a South polarity and an opposite inner portion with a North polarity. In this orientation, the North polarity outer portion of shell magnet 6218 is attracted to the South polarity outer portion of conduit magnet 6318. In contrast, second shell magnet carrier 6215 includes second shell magnet 6228. Second shell magnet 6228 has an outer portion (facing away from shell 6220) with South polarity and an opposite inner portion with North polarity. Second conduit magnet 6328 has an outer portion with North polarity and an inner portion with South polarity. Thus, the polarity of shell magnet 6218 is in an opposite orientation from second shell magnet 6228. Further, the polarity of conduit magnet 6318 also has an opposite orientation from second conduit magnet 6328. If conduit connector assembly 6310 was oriented adjacent second shell magnet carrier 6215 magnetic forces between second shell magnet 6228 and conduit magnet 6318 would repel one another. That is because the South polarity portions of second shell magnet 6228 and conduit magnet 6318 would be facing one another. Therefore the arrangement of magnets within shell assembly 6200 and the conduit connector assemblies may reduce the possibility of incorrect assembly between patient interface 6000 and mask assembly 6050.

The configuration of as shown in FIG. 10 includes shell magnet 6218 with a consistent North polarity on the outer portion and conduit magnet 6318 with a consistent South polarity of the outer portion such that shell magnet 6218 and conduit magnet 6318 are attracted to each other. By forming the magnets to include a single polarity on either surface (rather than switching the poles), the magnets are able to connect to each other at various angles. For example, conduit connector assembly 6310 may be able to rotate about Axis A and connect to shell receptor assembly 6230 at various angles. By arranging the magnetic forces in such a manner, conduit connector assembly 6310 and shell receptor assembly 6230 may be simply and easily connected to each other without the need to have a particular angular arrangement with respect to Axis A prior to attachment.

Utilizing magnets to connect shell receptor assembly 6230 and conduit connector assembly 6310 may permit self-locating between conduit connector assembly 6310 and shell receptor assembly 6230. Because the components utilize magnets, shell receptor assembly 6230 and conduit connector assembly 6310 need not be perfectly aligned. When arranged sufficiently close to each other, the magnetic forces may orient the shell receptor assembly 6230 with the conduit connector assembly 6310 without the need for the patient to particularly align the components. By increasing the ease at which the components can be connected a patient may be more inclined to where the patient interface 6000 to maintain therapy treatment.

Referring to FIG. 11, conduit connector assembly 6311 is depicted in conjunction with a portion of headgear conduit 6302. Headgear conduit 6302 is formed of a textile material such as a woven, non-woven, knit, braided, or any other network of fibres. Additionally, headgear conduit 6302 may be formed of a silicone, hard plastic or soft plastic, or plastic overmolded with textile or any combinations of materials. In other forms, headgear conduit 6302 may include rigid portions and floppy portions along the length of headgear conduit 6302. As depicted, headgear conduit 6302 is formed at least partially from a textile material.

Headgear conduit 6302 may be attached to conduit connector assembly 6311 such that air that is located within headgear conduit 6302 may pass through conduit connector assembly 6311 and to mask assembly 6050 with minimal leakage. In some forms, conduit connector assembly 6311 may be located substantially within headgear conduit 6302. In other forms, such as depicted in FIG. 11, conduit connector assembly 6311 may be secured along an outer surface of headgear conduit 6302. Conduit connector assembly 6311 (as well as conduit connector assembly 6310), may be secured to headgear conduit 6302 through thermoplastic, thermobonding (such as through the use of thermoset materials), as well as glue adhesive, other mechanical configurations, as well as any combination of the various securement mechanisms described above.

As shown in FIG. 11, air 6304 is directed along headgear conduit 6302 and through both conduit connector assembly 6311 and shell assembly 6200. The channel between mask assembly 6050 and headgear conduit 6302 may be substantially air tight to minimize the quantity of leakage of air through patient interface 6000.

Referring now to FIG. 12, a cross-sectional view of conduit connector assembly 6310 and shell assembly 6200 is depicted. As shown, connector 6316 includes an upper and lower lips 6330, 6332. In some forms, upper and lower lips 6330, 6332 may be continuous with front lip 6314. In other forms upper and lower lips 6330, 6332 may be spaced from front lip 6314 such that the line on which the lips are located is discontinuous. As shown, upper and lower lips 6330, 6332 engage with the outer face of shell magnet carrier 6214. In this manner, conduit connector assembly 6310 may be restricted from pulling off or moving in various direction. For example, upper and lower lips 6330, 6332 may restrict conduit connector assembly 6310 from moving upward and downward with respect to shell assembly 6200. By including upper and lower lips 6330, 6332 the possibility of accidental removal of conduit connector assembly 6310 from shell assembly 6200 may be reduced. Although described as upper and lower lips 6330, 6332 it should be recognized that the "upper" and "lower" lip may be flipped depending on the orientation of the connector 6316 with respect to the patient. Such terms are utilized in this specification for ease of description.

As can be clearly seen in FIG. 13, the lip formed by upper and lower lip 6330, 6332 along with front lip 6314 does not extend completely around connector opening 6312. This permits conduit connector assembly 6310 to be able to be removed from mask assembly 6050 without being restrained by further features from connector 6316.

The configuration of front lip 6314 along with upper and lower lips 6330, 6332 may permit various patients to use similarly shaped patient interfaces. A mask assembly such as mask assembly 6050 may conform to different patients along different planes such that the conduit connector assemblies do not always provide tension in the same direction. For example, some headgear 6300 may provide tension in a substantially anterior direction, whereas on other patients the headgear 6300 may provide tension in a more superior direction. Depending on the shape of the face, different tensions may occur. When oriented in different manners the conduit connector assemblies may rotate with respect to various patient faces. As described above, the junction between mask assembly 6050 and headgear 6300 is formed utilizing magnets. The magnetic field attachment may permit the conduit connector assemblies to rotate (for example, about Axis A shown in FIG. 9) with respect to mask assembly 6050. This rotation may permit different sized and shaped faces to use the same patient interface and may also be used to adjust the orientation of first and second extensions 6306, 6308 direct the force vectors therefrom. Further, by including front lip 6314, along with upper and lower lips 6330, 6332, headgear 6300 may be able to rotate and still provide adequate and appropriate tension along different planes to mask assembly 6050.

Referring now to FIG. 13, in some forms the conduit connector assemblies may include alignment features to secure the conduit connector assemblies in place with respect to the mask assembly. As shown, conduit connector assembly 6310 includes a male alignment feature 6334. Alignment feature 6334 may be various shapes including rectangular, square, trapezoidal, circular, and pyramidal or other shapes. As depicted, alignment feature 6334 is substantially cylindrical in shape. Alignment feature 6334 may be a separate component or may be integrated or formed with other components of conduit connector assembly 6310. For example, alignment feature 6334 may be integrally formed with conduit magnet carrier 6336. Shell assembly 6200 may include a corresponding female receptor feature 6238. Receptor feature 6238 may be formed in the negative of alignment feature 6334 so as to accept alignment feature 6334. When aligned with each other the alignment feature 6334 and receptor feature 6238 restrict the rotation of conduit connector assembly 6310 with respect to shell assembly 6200.

In some forms, the alignment and receptor features may be offset from the center of the shell opening 6212 and the connector opening 6312. By offsetting the alignment and receptor features, accidental alignment of the incorrect conduit connector assembly may be reduced. As shown, alignment feature 6334 is offset from the center of connector opening 6312 by a distance X. Receptor feature 6338 is similarly offset from the center of shell opening 6212 by a distance X. The opposite conduit connector assembly 6311 and second shell opening 6216 may have an oppositely arranged alignment and receptor feature such that the alignment feature 6334 would not be able to be aligned with the receptor feature around shell opening 6212. Additionally, the alignment and receptor features may be differently shaped such that a connection between incorrect receptor and alignment features would be reduced.

Referring now to FIG. 14, an exploded cross sectional view of conduit connector assembly 6310 and components of shell assembly 6200 associated with shell opening 6212. As shown, conduit connector assembly 6310 includes connector 6316, conduit magnet 6318 and conduit magnet carrier 6336. Connector 6316 includes a raised platform 6340 (see FIG. 22) for receiving conduit magnet 6318. The outer surface of raised platform 6340 may substantially correspond to the surface of conduit magnet 6318 that rests upon raised platform 6340. In some forms, conduit magnet 6318 may be glued or otherwise secured to raised platform 6340. In other forms, a raised platform may not be utilized and/or the conduit magnet may be unattached to the raised platform. Conduit magnet carrier 6336 is configured to extend around and three sides of conduit magnet 6318 and form a barrier between any pass through conduit connector assembly 6310 and conduit magnet 6318.

As shown, conduit magnet carrier 6336 includes a channel or groove 6342 (see FIG. 20) that extends around the opening of conduit magnet carrier 6336. Groove 6342 may be shaped and sized to accept conduit magnet 6318 such that conduit magnet 6318 is sandwiched between conduit magnet carrier 6336 and connector 6316. Further, when assembled with connector 6316 and conduit magnet 6318 groove 6342 may also be sufficiently deep to accommodate raised platform 6340. That is, when assembled the ends of conduit magnet carrier 6336 contact the surface of connector 6316 such that the interior surfaces of conduit magnet carrier 6336 abut against surfaces of raised platform 6340 as well as conduit magnet 6318. In other forms, the inner surfaces of groove 6342 may be spaced from the outer surfaces of conduit magnet 6318 and raised platform 6340 however conduit magnet carrier 6336 may seal conduit magnet 6318 and/or raised platform 6340 from air that may pass through conduit connector assembly 6310.

Conduit magnet carrier 6336 may be secured to connector 6316 through adhesive or other mechanism. Further, in some forms, conduit magnet 6318 may be secured to conduit magnet carrier 6336 and in other forms conduit magnet 6318 may be secured to raised platform 6340. In either form, however, conduit magnet may be located within groove 6342 of conduit magnet carrier 6336 when fully assembled.

Conduit magnet 6318 may be substantially ring-shaped or cylindrical shaped. As shown throughout the Figures, conduit magnet 6318 is a continuous ring. In other forms, conduit magnet 6318 may comprise multiple magnets that are oriented to attract an oppositely polarized magnet of shell assembly 6200. By utilizing a continuous cylindrical magnet, a secure or consistent connection between conduit magnet 6318 and shell magnet 6218 may be formed. That is, rather than multiple magnets that may be spaced from one another, both conduit magnet 6318 and shell magnet 6218 are formed as single components with a constant and consistent area of polarity that permits a constant and consistent connection between shell assembly 6200 and conduit connector assembly 6310.

Shell assembly 6200 includes shell receptor assembly 6230. Shell receptor assembly 6230 includes shell magnet carrier 6214 and shell magnet 6218. Shell receptor assembly 6230 may be positioned to circumscribe shell opening 6212. The upper surface of raised platform 6240 may be spaced from the surrounding areas of shell assembly 6200. In a similar manner as raised platform 6340 of conduit connector assembly 6310, raised platform 6240 may be formed to circumscribe shell opening 6212. Further, raised platform 6240 may be shaped to abut an inner surface of shell magnet 6218.

Shell magnet carrier 6214 may include a groove 6242 to accept and accommodate shell magnet 6218. Further, shell magnet carrier 6214 may also be shaped to extend around the exposed surfaces of shell magnet 6218 so as to limit the amount of air that may leak between shell magnet carrier 6214 and shell magnet 6218. As depicted for example in FIG. 10, shell magnet carrier 6214 abuts an outer surface of shell 6220. Further, the inner wall of shell magnet carrier 6214 is also configured to extend along the inner surface of raised platform 6240. As shown, raised platform 6240 bounds shell opening 6212 such that there is no shoulder beyond raised platform 6240 (in contrast to the inner shoulder of raised platform 6340). In other forms, raised platform 6240 may be similarly shaped and formed as raised platform 6340 associated with conduit connector assembly 6310.

Referring to FIGS. 15-24, various components of shell assembly 6200 and conduit connector assembly 6310 are depicted in isolation. Referring to FIG. 15, shell 6220 is depicted. In some forms, shell 6220 may also include a vent for venting waste air away from the patient. Shell 6220 includes shell opening 6212 and second shell opening 6216. Shell opening 6212 is surrounded by raised platform 6240. Raised platform 6240 may be integrally formed with the rest of shell 6220 or may be separately attached. Surrounding raised platform 6240 in shell channel 6244. Shell channel 6244 is a depression within shell 6220 that completely surrounds raised platform 6240. Shell channel 6244 may be shaped to accept a portion of shell magnet carrier 6214. Additionally, raised platform 6240 may restrict the lateral motion of shell magnet carrier 6214. Between shell opening 6212 and second shell opening 6216 is central portion 6246. Central portion 6246 may be a partially curved section such that shell opening 6212 and second shell opening 6216 are oriented in different planes. Shell 6220 may be formed in various configuration and shapes. For example, in other forms a nasal mask, or full face mask shell may be utilized.

Various types of materials may be utilized for shell 6220. In some forms, a hard plastic material such as a polycarbonate may be utilized. Forming shell 6220 of a polycarbonate material may provide sufficient rigidity for use with a corresponding seal forming structure 6100. That is, shell 6220 may be able to maintain the shape of seal forming structure 6100 in the areas that shell 6220 interacts with seal forming structure 6100 so that a consistent seal is formed between sealing forming structure 6100 and the patient. In other forms, thermoplastic materials, thermoset materials, metal materials, woven and non-woven materials, in addition to rubber or elastomeric materials may be utilized to form shell 6220.

In some forms, shell 6220 may be formed of a metal material or contain ferrite or carbon material. In such forms, shell 6220 may permit attraction from with conduit connector assembly 6310 or conduit connector assembly 6311. In some forms, rather than including a separate magnet component such as shell magnet 6218 and shell magnet carrier 6214, shell 6220 may be formed of a magnetic or metal material. Further, the shell 6220 may be overlaid with a seal or o-ring or other sealing mechanism to provide an air flow path between conduit connector assembly 6310 and shell 6220. Additionally, the other components such as conduit connector assembly 6310 may be formed of a metallic material or magnetic material such that a separate carrier or magnet need not be necessary.

Referring now to FIGS. 16-18, various views of shell magnet carrier 6214 are shown. Shell magnet carrier 6214 includes an upper surface 6248 and an upper flange surface 6250. Upper surface 6248 and upper flange surface 6250 are spaced from each other by outer wall 6252. As seen in particular in FIG. 17, outer wall 6252 tapers inward toward the center of shell magnet carrier 6214 from upper surface 6248 to upper flange surface 6250. As described previously, this angled outer wall 6252 may cooperate with the front lip 6314 of connector 6316 to assist in retaining conduit connector assembly 6310 in place during use of patient interface 6000. Outer wall 6252 may be substantially linear along the height of shell magnet carrier 6214. That is, outer wall 6252 may have a substantially flat line orientation in a height direction. Flange 6254 extends outwardly from outer wall 6252. Flange 6254 may be situated within shell channel 6244 of shell 6220 By forming flange 6254 to fit within shell channel 6244 the likelihood of shell magnet carrier 6214 translating during use is minimized. Flange 6254 may be pressed between raised platform 6240 and the outer wall of shell channel 6244. This may prevent or reduce the movement of shell magnet carrier 6214 with respect to shell 6220.

As shown at least in FIG. 18, shell magnet carrier 6214 includes a central wall 6256. Central wall 6256 defines shell magnet carrier opening 6258 which forms a portion of shell opening 6212. As shown in FIGS. 10 and 12, central wall 6256 extends along the inner wall of raised platform 6240, and defines a portion of shell opening 6212. Further, central wall 6256 also defines a boundary of groove 6242 within shell magnet carrier 6214. The length and shape of central wall 6256 may be modified depending on the shape of raised platform 6240 as well as the desired shape of shell opening 6212. Central wall 6256 may extend beyond the lower boundaries of shell magnet 6218 so as to limit air leakage through shell magnet carrier opening 6258 to shell magnet 6218.

In some forms shell magnet carrier 6214 is formed of a conformable material such as a rubber, liquid silicone, or elastomeric material. As depicted in FIGS. 6-15 and 16-18, shell magnet carrier 6214 is formed of an elastomeric or rubber material. This material construction permits shell magnet carrier 6214 to reduce the quantity of air leakage through shell assembly 6200. In other forms, shell magnet carrier 6214 may be formed of other materials such as polycarbonate materials, metal, hard plastic, silicone or other materials. As depicted in FIGS. 25 and 26, alternative forms of shell magnet carrier 6214 are utilized with seals or O-rings.

Referring now to FIGS. 19-21, various views of conduit magnet carrier 6336 are depicted. Conduit magnet carrier 6336 includes an upper surface 6344. This surface is configured to be oriented toward upper surface 6248 when patient interface 6000 is worn. An outer wall 6346 tapers outward from upper surface 6248 such that the outer wall 6346 has a greater circumference farther away from upper surface 6248. Outer wall 6346 may be arranged in such a manner so as to not interfere with the front lip 6314 as well as the upper and lower lips 6330, 6332 of connector 6316. In a similar manner as describe above with reference to shell magnet carrier 6214, conduit magnet carrier 6336 includes a central wall 6348. Central wall 6348 defines a portion of the flow path of air 6304 that flows through conduit connector assembly 6310 and to shell assembly 6200. Further, the outer wall 6346 and central wall 6348 may form the boundaries of groove 6342 in which conduit magnet 6318 is positioned. The shape, size, and orientation of conduit magnet carrier 6336 may be changed or altered depending on the particular design criteria of conduit connector assembly 6310.

Various materials may be used to form conduit magnet carrier 6336. As shown in FIGS. 5-14, and 19-21, conduit magnet carrier 6336 is formed of an elastomeric or rubber material. Such material may be utilized to form a seal between shell magnet carrier 6214 and conduit magnet carrier 6336 thereby limiting the quantity of air that may leak between conduit connector assembly 6310 and shell assembly 6200. Further, the material may also assist in limiting the quantity of air that is able to pass between connector 6316 and conduit magnet carrier 6336 or conduit magnet 6318. Other material configurations may be utilized. For example, conduit magnet carrier 6336 may be formed of polycarbonate, hard plastic, soft plastic, silicone, metal or other material.

Referring now to FIGS. 22-24, various views of connector 6316 are depicted. As shown, connector 6316 includes a planar layer 6350. Planar layer 6350 includes a curved edge 6352 that extends between and connects first and second edges 6354, 6356. Opposite of curved edge is third edge 6358 that extends between first and second edges 6354, 6356. Further, connector 6316 also includes a projecting wall 6360 that projects away from layer 6350. In some forms, projecting wall 6360 may angle inward, however in other forms projecting wall 6360 may be substantially orthogonal to layer 6350. Projecting wall 6360 is oriented along the edges of layer 6350. As depicted, projecting wall 6360 extends along curved edge 6352, first edge 6354 and second edge 6356. Additionally, projecting wall 6360 is not shown extending along third edge 6358. By not including a projecting wall along third edge 6358 conduit connector assembly 6310 may be permitted to be removed by pushing or pressing connector 6316 such that third edge 6358 moves toward shell magnet carrier 6214.

Projecting wall 6360 may have different widths or depths depending on the location along connector 6316. As described previously, connector 6316 may include front lip 6314, as well as upper and lower lips 6330, 6332. These lip portions have greater depths than adjacent portions of projecting wall 6360. This lip portions may be utilized to grab or engage with shell magnet carrier 6214 during use of patient interface 6000. Other portions of projecting wall 6360 may assist in providing a rigidity to connector 6316 so as to reduce the likelihood of occlusion of headgear conduit 6302 during use.

Further, as described previously, connector 6316 includes raised platform 6340. Raised platform 6340 may be provided to allow for simple manufacturing such that the location of conduit magnet 6318 and conduit magnet carrier 6336 is readily obvious. Further, raised platform 6340 may also assist in restricting or restraining lateral movement of conduit magnet carrier 6336 with respect to connector 6316.

As depicted in FIGS. 1-14, and 17-26 connector 6316 is formed of a plastic material such as polycarbonate. The hard plastic material of connector 6316 may assist in providing a stable and sturdy structure to which to secure conduit magnet 6318 and conduit magnet carrier 6336. In other forms connector 6316 may be formed of a different hard plastic, a soft plastic, silicone, rubber or an elastomeric material.

Referring now to FIGS. 25 and 26 a portion of shell assembly 6200 and conduit connector assembly 6310 are depicted with different materials. Referring particularly to FIG. 25, both shell magnet carrier 6214 and conduit magnet carrier 6336 are formed of plastic. In such a configuration a plurality of add-on seals 6400 are placed over both shell magnet carrier 6214 and conduit magnet carrier 6336. Add-on seals 6400 may be formed of a rubber, elastomeric, or other seal providing material. Add-on seals 6400 may be secured to either or both of shell magnet carrier 6214 and conduit magnet carrier 6336 after each component has been formed. As shown add-on seals 6400 extend along the interior faces of conduit magnet carrier 6336 and shell magnet carrier 6214. In other forms, add-on seals 6400 may only extend partially along the carriers. As shown, the add-on seals 6400 abut one another at the junction between shell assembly 6200 and conduit connector assembly 6310. This may reduce the quantity of air leakage at the junction. Additionally, in some forms, one or the other of conduit magnet carrier 6336 and shell magnet carrier 6214 may be formed of rubber or elastomeric material such as described with reference to FIGS. 5-14. In such forms, if the carrier is formed of a seal-type material, it may not be necessary to include an add-on seal on the carrier. For example, conduit magnet carrier 6336 may be formed of a seal-type material. Shell magnet carrier 6214 may be formed of a hard plastic material with poor sealing properties. Shell magnet carrier 6214 therefore may include an add-on seal 6400 while conduit magnet carrier 6336 may not include an add-on seal 6400.

As shown in FIG. 26, another form of sealing between shell magnet carrier 6214 and conduit magnet carrier 6336 is depicted. As shown both shell magnet carrier 6214 and conduit magnet carrier 6336 include overmold seals 6410. Overmold seals 6410 may be over molded onto one or both of shell magnet carrier 6214 and conduit magnet carrier 6336. As describe with reference to FIG. 25, however, the material of shell magnet carrier 6214 or conduit magnet carrier 6336 may be changed such that only one of the carrier includes overmold seals 6410. In some forms, additional seals such as O-ring seals may be utilized. In such forms the carriers may include a groove in the upper surfaces to accept the O-ring seals.

In other forms, a combination of the form of FIGS. 25 and 26 along with previous forms may be utilized. For example, shell magnet carrier 6214 may utilize overmold seal 6410 and conduit magnet carrier 6336 may be formed of rubber and not utilize a separate seal. In other forms, shell magnet carrier 6214 may utilize an add-on seal 6400 while conduit magnet carrier 6336 utilizes an overmold seal 6410. Any combination of seals and materials may be utilized to form an adequately sealed junction between shell assembly 6200 and conduit connector assembly 6310.

Referring to FIG. 27, an alternative form of the present technology is depicted. As shown, patient interface 7000, includes a mask assembly 7050 and an air delivery conduit connection assembly 7310. Mask assembly 7050 may include a magnet that is configured to attract a magnet associated with air conduit connection assembly 7310. In some forms mask assembly 7050 may include a magnet carrier similar to shell magnet carrier 6214. Further, air delivery conduit connection assembly 7310 may include a magnet carrier similar to conduit magnet carrier 6336. In such a manner an air delivery conduit may be connected to a full face mask that includes a magnetic connection.

Referring to FIG. 28, an alternate form of the present technology is depicted. As shown, headgear 6300 includes connection port 6600 and air circuit 4170. Connection port 6600 may be equipped with an inset magnet to associate connection port 6600 with end 6602 of air circuit 4170. End 6602 of air circuit 4170 may also include a magnet so that end 6602 may magnetically connect with connection port 6600. When configured in such a configuration air may be able to pass from air circuit 4170 and through connection port 6600. In this sense, the magnetic connections described in this specification may be utilized in other areas of a patient interface. Further, different configurations of patient interfaces may include similar features. For example patient interface 7000, although a full face mask with a different configuration than patient interface 6000 may still utilized a magnetic connection between various components.

8.3.2.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

8.3.2.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

8.3.2.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

8.3.2.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

8.3.2.5 Forehead Region

In one form, the seal-forming structure that forms a seal in use on a forehead region of the patient's face. In such a form, the plenum chamber may cover the eyes in use.

8.3.2.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

8.3.3 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

8.3.4 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

8.3.5 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200 or shell 6220. Alternatively, the vent 3400 is located in a decoupling structure, e.g., a swivel or within headgear conduit 6302 or adjacent conduit connector assembly 6310.

8.3.6 Decoupling Structure(s)

In one form the patient interface 3000 includes at least one decoupling structure, for example, a swivel or a ball and socket.

8.3.7 Connection Port

Connection port 3600 allows for connection to the air circuit 4170.

8.3.8 Forehead Support

In one form, the patient interface 3000 includes a forehead support 3700.

8.3.9 Anti-Asphyxia Valve

In one form, the patient interface 3000 includes an anti-asphyxia valve.

8.3.10 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

8.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

8.4.1 RPT Device Mechanical & Pneumatic Components

An RPT device may comprise one or more of the following components in an integral unit. In an alternative form, one or more of the following components may be located as respective separate units.

8.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

8.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

8.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a blower housing, such as in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

8.4.1.3.1 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

8.4.1.4 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

8.4.1.5 Clock

The RPT device 4000 may include a clock 4232 that is connected to the central controller 4230.

8.4.1.6 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

8.4.1.7 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

8.4.1.7.1 Display Driver

A display driver 4292 receives as an input the characters, symbols, or images intended for display on the display 4294, and converts them to commands that cause the display 4294 to display those characters, symbols, or images.

8.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

8.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

8.6 Humidifier

8.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

8.6.2 Humidifier Components

8.6.2.1 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

8.6.2.2 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

8.6.2.3 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

8.7 Glossary

For the purposes of the present technology disclosure, in certain forms of the present technology, one or more of the following definitions may apply. In other forms of the present technology, alternative definitions may apply.

8.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

8.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

8.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

8.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peakflow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

8.7.3 Anatomy
8.7.3.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 8.7.3.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

8.7.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

8.7.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

8.7.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

8.7.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

8.7.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

8.7.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

8.7.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

8.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8.9 Reference Signs List

1000 patient
1100 bed partner
3000 patient interface
3100 seal-forming structure
3200 plenum chamber
3210 chord
3220 superior point
3230 inferior point
3300 stabilizing structure
3400 vent
3600 connection port
3700 forehead support
4000 RPT device
4010 external housing
4012 upper portion
4014 portion
4015 panel
4016 chassis
4018 handle
4020 pneumatic block
4100 pneumatic components
4110 air filter
4112 inlet air filter
4114 outlet air filter
4120 muffler
4122 inlet muffler
4124 outlet muffler
4140 pressure generator
4142 controllable blower
4144 brushless DC motor
4160 anti-spillback valve
4170 air circuit
4180 supplemental oxygen
4200 electrical components
4202 printed circuit board assembly (PCBA)
4210 electrical power supply
4220 input devices
4230 central controller
4232 clock
4240 therapy device controller
4250 protection circuits
4260 memory
4270 transducers
4272 pressure sensors
4274 flow rate sensors
4276 Motor speed transducer
4280 data communication interface
4282 remote external communication network
4284 local external communication network
4286 remote external device
4288 local external device
4290 output devices
4292 display driver
4294 display
4300 algorithms
5000 humidifier
5002 humidifier inlet
5004 humidifier outlet
5006 humidifier base
5110 humidifier reservoir
5120 conductive portion
5130 humidifier reservoir dock
5135 locking lever
5150 water level indicator
5240 heating element
6000 patient interface
6050 mask assembly
6097 direction
6098 direction
6099 direction
6100 seal forming structure
6200 shell assembly
6212 shell opening
6214 shell magnet carrier
6215 second shell magnet carrier
6216 second shell opening
6218 shell magnet
6220 shell
6222 slot
6224 groove
6228 second shell magnet
6230 shell receptor assembly
6240 raised platform
6242 groove
6244 shell channel
6246 central portion
6248 upper surface
6250 upper flange surface
6252 outer wall
6254 flange
6256 central wall
6258 shell magnet carrier opening
6300 headgear
6302 headgear conduit
6304 air
6306 first arm
6308 second arm 6309 force
6310 conduit connector assembly
6311 conduit connector assembly
6312 connector opening
6314 front lip
6316 connector
6318 conduit magnet
6328 second conduit magnet
6330 upper lip
6332 lower lip
6334 alignment feature
6336 conduit magnet carrier
6338 receptor feature
6340 raised platform
6342 groove
6344 upper surface
6346 outer wall
6348 central wall
6350 layer
6352 curved edge
6354 first edge
6356 second edge
6358 third edge
6360 projecting wall
6399 direction
6400 add-on seals
6410 overmold seals
6600 connection port
6602 end
7000 patient interface
7050 mask assembly
7310 air delivery conduit connection assembly
$F_1$ direction
$F_2$ direction
A axis
T tension

9 CITATIONS 9.1 Patent Literature
9.2 Non-Patent Literature

The invention claimed is:

1. A system comprising:
an RPT device, a patient interface, and an air circuit configured to connect the RPT device to the patient interface;
the RPT device configured to supply air at positive pressure for respiratory therapy;
the air circuit configured to connect to the patient interface at a connection port;
the patient interface including a positioning and stabilising structure and a mask assembly including a plenum chamber and a seal forming structure, the positioning and stabilising structure including a headgear conduit configured to receive a therapeutic pressure of at least 6 cmH$_2$O above ambient air pressure from the air circuit, the headgear conduit configured to extend along a crown of a patient's head from a first parietal bone to a second parietal bone;
the plenum chamber including a first plenum chamber receptor assembly,
wherein the first plenum chamber receptor assembly includes a plenum chamber opening configured to receive a flow of air at the therapeutic pressure for breathing by a patient;
the seal forming structure configured to form a seal with a region of a patient's face surrounding an entrance to a patient's airways, said seal forming structure having a hole configured to allow the flow of air at said therapeutic pressure to be delivered to at least an entrance to a patient's nares, the seal forming structure configured to maintain said therapeutic pressure in the mask assembly throughout a patient's respiratory cycle in use;
the headgear conduit including a first end with a first conduit connector assembly,
wherein the first conduit connector assembly is configured to engage with the first plenum chamber receptor assembly,
wherein the first conduit connector assembly includes a connector opening, and
wherein, when the first conduit connector assembly is engaged with the first plenum chamber receptor assembly, the connector opening is configured to align with the plenum chamber opening and form a channel through which air is delivered from the headgear conduit, through the first conduit connector assembly, and through the first plenum chamber receptor assembly to the mask assembly;
wherein, when the first conduit connector assembly is engaged with the first plenum chamber receptor assembly, the first conduit connector assembly is configured to be rotatable relative to the first plenum chamber receptor assembly about an axis of the plenum chamber opening of the first plenum chamber receptor assembly;
wherein, when the first conduit connector assembly is engaged with the first plenum chamber receptor assembly, the first conduit connector assembly is restricted from translating in a first direction perpendicular to the axis of the plenum chamber opening; and
wherein, when the first conduit connector assembly is engaged with the first plenum chamber receptor assembly, the first conduit connector assembly is permitted to translate in a second direction that is perpendicular to the axis of the plenum chamber opening and opposite to the first direction.

2. The system according to claim 1, wherein the first conduit connector assembly includes a retention member, wherein the first plenum chamber receptor assembly includes a tapered outer wall, wherein the retention member is angled and configured to engage with the tapered outer wall of the first plenum chamber receptor assembly, and wherein an inner surface of the retention member is substantially linear and an outer surface of the tapered outer wall is substantially linear.

3. The system according to claim 2, wherein the first plenum chamber receptor assembly comprises a shell magnet carrier including an upper surface, the tapered outer wall, and an upper flange surface, wherein the upper surface and the upper flange surface are spaced from each other by the tapered outer wall, and wherein the tapered outer wall tapers inward toward a center of the shell magnet carrier from the upper surface to the upper flange surface.

4. The system according to claim 3, wherein the retention member of the first conduit connector assembly comprises a front lip that does not extend all around a perimeter of the first conduit connector assembly, and the front lip includes an angled interior surface configured to lie flush against the tapered outer wall.

5. The system according to claim 1, wherein, when the first conduit connector assembly is engaged with the first plenum chamber receptor assembly, the first conduit connector assembly is restricted to translate in various directions of a single plane including the first direction.

6. The system according to claim 5, wherein the various directions include directions outward from the sagittal plane.

7. The system according to claim 1, wherein the first plenum chamber receptor assembly and the first conduit connector assembly are attracted to each other through a magnetic force, and, when the first conduit connector assembly is engaged with the first plenum chamber receptor assembly, a seal is formed between the first plenum chamber receptor assembly and the first conduit connector assembly.

8. The system according to claim 7, wherein the magnetic force is configured to self-align the connector opening with the plenum chamber opening.

9. The system according to claim 1, wherein, when the patient interface is worn by the patient, the first conduit connector assembly is a tie configured to provide a posterior force to the mask assembly.

10. The system according to claim 1, wherein the first conduit connector assembly is configured to be rotatable relative to the first plenum chamber receptor assembly about the axis of the plenum chamber opening while maintaining a seal between the first conduit connector assembly and the first plenum chamber receptor assembly.

11. The system according to claim 1, wherein the headgear conduit further comprises a second end with a second conduit connector assembly, wherein the plenum chamber of the mask assembly further comprises a second plenum chamber receptor assembly, wherein the second conduit connector assembly is configured to engage with the second plenum chamber receptor assembly, and wherein, when the second conduit connector assembly is engaged with the second plenum chamber receptor assembly, air is configured to pass from the headgear conduit, through the second conduit connector assembly and through the second plenum chamber receptor assembly to the mask assembly.

12. The system according to claim 1, wherein the first direction is laterally inward toward the sagittal plane.

13. The system according to claim 1, wherein the second direction is a direction opposite of a direction of force applied upon the first conduit connector assembly by the positioning and stabilising structure.

14. The system according to claim 1, wherein the patient interface comprises a pair of nasal puffs or pillows.

15. A patient interface for delivering a flow of air at a positive pressure to a patient for respiratory therapy, the patient interface comprising:
a positioning and stabilising structure and a mask assembly including a plenum chamber and a seal forming structure, the positioning and stabilising structure including a headgear conduit configured to receive a therapeutic pressure of at least 6 cmH$_2$O above ambient air pressure from an air circuit, the headgear conduit configured to extend along a crown of a patient's head from a first parietal bone to a second parietal bone;
the plenum chamber including a first plenum chamber receptor assembly,
wherein the first plenum chamber receptor assembly includes a plenum chamber opening configured to receive a flow of air at the therapeutic pressure for breathing by a patient;
the seal forming structure configured to form a seal with a region of a patient's face surrounding an entrance to a patient's airways, said seal forming structure having a hole configured to allow the flow of air at said therapeutic pressure to be delivered to at least an entrance to a patient's nares, the seal forming structure configured to maintain said therapeutic pressure in the mask assembly throughout a patient's respiratory cycle in use;
the headgear conduit including a first end with a first conduit connector assembly,
wherein the first conduit connector assembly is configured to engage with the first plenum chamber receptor assembly,
wherein the first conduit connector assembly includes a connector opening, and
wherein, when the first conduit connector assembly is engaged with the first plenum chamber receptor assembly, the connector opening is configured to align with the plenum chamber opening and form a channel through which air is delivered from the headgear conduit, through the first conduit connector assembly, and through the first plenum chamber receptor assembly to the mask assembly;
wherein, when the first conduit connector assembly is engaged with the first plenum chamber receptor assembly, the first conduit connector assembly is configured to be rotatable relative to the first plenum chamber receptor assembly about an axis of the plenum chamber opening of the first plenum chamber receptor assembly;
wherein, when the first conduit connector assembly is engaged with the first plenum chamber receptor assembly, the first conduit connector assembly is restricted from translating in a first direction perpendicular to the axis of the plenum chamber opening; and
wherein, when the first conduit connector assembly is engaged with the first plenum chamber receptor assembly, the first conduit connector assembly is permitted to translate in a second direction that is perpendicular to the axis of the plenum chamber opening and opposite to the first direction.

16. The patient interface according to claim 15, wherein the first plenum chamber receptor assembly and the first conduit connector assembly are attracted to each other through a magnetic force, and, when the first conduit connector assembly is engaged with the first plenum chamber receptor assembly, a seal is formed between the first plenum chamber receptor assembly and the first conduit connector assembly.

17. The patient interface according to claim 16, wherein the magnetic force is configured to self-align the connector opening with the plenum chamber opening.

18. The patient interface according to claim 15, wherein, when the patient interface is worn by the patient, the first conduit connector assembly is a tie configured to provide a posterior force to the mask assembly.

19. The patient interface according to claim 15, wherein the first conduit connector assembly is configured to be rotatable relative to the first plenum chamber receptor assembly about the axis of the plenum chamber opening while maintaining a seal between the first conduit connector assembly and the first plenum chamber receptor assembly.

20. The patient interface according to claim 15, wherein the headgear conduit further comprises a second end with a second conduit connector assembly, wherein the plenum chamber of the mask assembly further comprises a second plenum chamber receptor assembly, wherein the second conduit connector assembly is configured to engage with the second plenum chamber receptor assembly, and wherein, when the second conduit connector assembly is engaged with the second plenum chamber receptor assembly, air is configured to pass from the headgear conduit, through the second conduit connector assembly and through the second plenum chamber receptor assembly to the mask assembly.

* * * * *